US010473647B1

(12) United States Patent
Anderson

(10) Patent No.: US 10,473,647 B1
(45) Date of Patent: Nov. 12, 2019

(54) PEPTIDES FOR USE IN TREATMENT AND DIAGNOSIS OF TYPE 1 DIABETES

(71) Applicant: ImmusanT, Inc., Cambridge, MA (US)

(72) Inventor: Robert P. Anderson, Shrewsbury, MA (US)

(73) Assignee: ImmusanT, Inc., Cambridge, MA (US)

( * ) Notice: Subject to any disclaimer, the term of this patent is extended or adjusted under 35 U.S.C. 154(b) by 79 days.

(21) Appl. No.: 15/528,172

(22) PCT Filed: Nov. 20, 2015

(86) PCT No.: PCT/US2015/061931
§ 371 (c)(1),
(2) Date: May 19, 2017

(87) PCT Pub. No.: WO2016/081869
PCT Pub. Date: May 26, 2016

Related U.S. Application Data

(60) Provisional application No. 62/082,823, filed on Nov. 21, 2014.

(51) Int. Cl.
| C07K 16/24 | (2006.01) |
| G01N 33/50 | (2006.01) |
| C07K 14/62 | (2006.01) |
| G01N 33/68 | (2006.01) |
| A61K 39/00 | (2006.01) |

(52) U.S. Cl.
CPC ......... *G01N 33/5091* (2013.01); *C07K 14/62* (2013.01); *C07K 16/24* (2013.01); *C07K 16/246* (2013.01); *C07K 16/249* (2013.01); *G01N 33/5088* (2013.01); *G01N 33/6863* (2013.01); *G01N 33/6866* (2013.01); *G01N 33/6869* (2013.01); *A61K 39/00* (2013.01); *G01N 2333/522* (2013.01); *G01N 2333/54* (2013.01); *G01N 2333/57* (2013.01); *G01N 2800/042* (2013.01); *G01N 2800/52* (2013.01)

(58) Field of Classification Search
CPC .................................................... A61K 38/00
See application file for complete search history.

(56) References Cited

U.S. PATENT DOCUMENTS

| 5,846,740 A | 12/1998 | Tobin et al. |
| 5,939,281 A | 8/1999 | Lehmann et al. |
| 5,981,700 A * | 11/1999 | Rabin .................. C07K 14/705 530/300 |
| 5,998,366 A | 12/1999 | Tobin et al. |
| 6,410,252 B1 | 6/2002 | Lehmann et al. |
| 6,455,267 B1 | 9/2002 | Tobin et al. |
| 6,514,295 B1 | 2/2003 | Chandler et al. |
| 6,599,331 B2 | 7/2003 | Chandler et al. |
| 6,632,526 B1 | 10/2003 | Chandler et al. |
| 6,929,859 B2 | 8/2005 | Chandler et al. |
| 6,929,924 B2 | 8/2005 | Bouanani et al. |
| 6,939,720 B2 | 9/2005 | Chandler et al. |
| 7,049,292 B2 | 5/2006 | Peakman |
| 7,445,844 B2 | 11/2008 | Chandler et al. |
| 7,575,870 B1 | 8/2009 | Lalvani et al. |
| 7,718,262 B2 | 5/2010 | Chandler et al. |
| 8,026,076 B2 | 9/2011 | Ruhwald et al. |
| 8,031,918 B2 | 10/2011 | Roth |
| 8,075,899 B1 | 12/2011 | Mannering et al. |
| 8,088,389 B1 | 1/2012 | Ben-Nun et al. |
| 8,148,171 B2 | 4/2012 | Chandler et al. |
| 8,274,656 B2 | 9/2012 | Roth et al. |
| 8,283,037 B2 | 10/2012 | Chandler et al. |
| 8,296,088 B2 | 10/2012 | Roth et al. |
| 8,378,072 B2 | 2/2013 | Bonnin |
| 8,481,485 B2 | 7/2013 | DiMarchi et al. |
| 8,501,189 B2 | 8/2013 | Ben-Nun et al. |
| 8,532,351 B2 | 9/2013 | Roth |
| 8,542,897 B2 | 9/2013 | Roth |
| 8,568,881 B2 | 10/2013 | Chandler et al. |
| 8,835,603 B2 | 9/2014 | Anderson et al. |
| 9,464,120 B2 | 10/2016 | Anderson et al. |
| 2008/0255766 A1 | 10/2008 | Spain et al. |
| 2009/0088329 A1 | 4/2009 | Brennan et al. |
| 2012/0214963 A1 | 8/2012 | Zimmerman et al. |
| 2014/0342936 A1 | 11/2014 | Rubbo et al. |
| 2016/0041148 A1 | 2/2016 | Anderson et al. |
| 2016/0238590 A1 | 3/2016 | Anderson et al. |
| 2016/0220629 A1 | 8/2016 | Anderson et al. |
| 2017/0042991 A1 | 2/2017 | Anderson et al. |
| 2017/0045513 A1 | 2/2017 | Anderson et al. |

(Continued)

FOREIGN PATENT DOCUMENTS

| EP | 2128612 A2 | 12/2009 |
| WO | WO 2001/025793 A2 | 4/2001 |

(Continued)

OTHER PUBLICATIONS

Thomas Arnesen, PLOS, Biology, vol. 9, published on May 31, 2011.*
Invitation to Pay Additional Fees dated Mar. 16, 2016 in connection with PCT/US2015/061931.
International Search Report and Written Opinion dated May 27, 2016 in connection with PCT/US2015/061931.
International Preliminary Report on Patentability dated May 23, 2017 in connection with PCT/US2015/061931.
[No Author Listed] Immune Epitope Database and Analysis Resource. Epitope ID 174773; MHC Ligand ID 1954190. Abreu et al. Oct. 26, 2014. Last accessed via http://www.iedb.org/epId/174773.
Abreu et al., CD8 T cell autoreactivity to preproinsulin epitopes with very low human leucocyte antigen class I binding affinity. Clin Exp Immunol. Oct. 2012;170(1):57-65. doi: 10.1111/j.1365-2249.2012.04635.x.

(Continued)

*Primary Examiner* — Gyan Chandra
(74) *Attorney, Agent, or Firm* — Wolf, Greenfield & Sacks, P.C.

(57) ABSTRACT

Provided herein are compositions and methods for treating autoimmune diabetes such as type 1 diabetes (T1D), diagnosing autoimmune diabetes such as T1D, assessing treatment efficacy, and selecting subjects for treatment, e.g., using a peptide or epitope disclosed.

12 Claims, 3 Drawing Sheets
Specification includes a Sequence Listing.

(56) References Cited

U.S. PATENT DOCUMENTS

| | | | |
|---|---|---|---|
| 2017/0045529 | A1 | 2/2017 | Anderson et al. |
| 2017/0059582 | A1 | 3/2017 | Anderson et al. |
| 2017/0097346 | A1 | 4/2017 | Anderson et al. |
| 2017/0158743 | A1 | 6/2017 | Anderson et al. |
| 2017/0218453 | A1 | 8/2017 | Anderson et al. |
| 2017/0232083 | A1 | 8/2017 | Anderson et al. |
| 2019/0048047 | A1 | 2/2019 | Anderson et al. |

FOREIGN PATENT DOCUMENTS

| | | | |
|---|---|---|---|
| WO | WO 2002/098346 | A2 | 12/2002 |
| WO | WO 2003/104273 | A2 | 12/2003 |
| WO | WO 2005/105129 | A2 | 11/2005 |
| WO | WO 2008/028489 | A2 | 3/2008 |
| WO | WO 1999/055849 | A1 | 1/2009 |
| WO | WO 2009/004315 | A1 | 1/2009 |
| WO | WO 2010/060155 | A1 | 6/2010 |
| WO | WO 2012/007950 | A2 | 1/2012 |
| WO | WO 2012/149320 | A1 | 11/2012 |
| WO | WO 2015/164727 | A1 | 10/2015 |

OTHER PUBLICATIONS

Ahmadzadeh et al., IL-2 administration increases CD4+ CD25(hi) Foxp3+ regulatory T cells in cancer patients. Blood. Mar. 15, 2006;107(6):2409-14.

Aly et al., . Extreme genetic risk for type 1A diabetes. Proc Natl Acad Sci U S A. Sep. 19, 2006;103(38):14074-9.

Anderson et al., Antagonists and non-toxic variants of the dominant wheat gliadin T cell epitope in coeliac disease. Gut. Apr. 2006;55(4):485-91. Epub Nov. 18, 2005.

Anderson et al., In vivo antigen challenge in celiac disease identifies a single transglutaminase-modified peptide as the dominant A-gliadin T-cell epitope. Nat Med. Mar. 2000;6(3):337-42.

Anderson et al., T cells in peripheral blood after gluten challenge in coeliac disease. Gut. Sep. 2005;54(9):1217-23.

Antvorskov et al., Dietary gluten alters the balance of pro-inflammatory and anti-inflammatory cytokines in T cells of BALB/c mice. Immunology. Jan. 2013;138(1):23-33.

Avalos et al., Monovalent engagement of the BCR activates ovalbumin-specific transnuclear B cells. J Exp Med. Feb. 10, 2014;211(2):365-79. doi: 10.1084/jem.20131603.

Barker et al., Two single nucleotide polymorphisms identify the highest-risk diabetes HLA genotype: potential for rapid screening. Diabetes. Nov. 2008;57(11):3152-5. doi: 10.2337/db08-0605.

Beissbarth et al., A systematic approach for comprehensive T-cell epitope discovery using peptide libraries.Bioinformatics. Jun. 2005;21 Suppl 1:i29-37.

Brottveit et al., Assessing possible celiac disease by an HLA-DQ2-gliadin Tetramer Test. Am J Gastroenterol. Jul. 2011;106(7):1318-24. doi: 10.1038/ajg.2011.23. Epub Mar. 1, 2011. Erratum in: Am J Gastroenterol. Apr. 2012;107(4):638.

Camarca et al., Short wheat challenge is a reproducible in-vivo assay to detect immune response to gluten. Clin Exp Immunol. Aug. 2012;169(2):129-36. doi: 10.1111/j.1365-2249.2012.04597.x.

Christophersen et al., Tetramer-visualized gluten-specific CD4+ T cells in blood as a potential diagnostic marker for coeliac disease without oral gluten challenge. United European Gastroenterol J. Aug. 2014;2(4):268-78. doi: 10.1177/2050640614540154.

Congia et al., T cell epitopes of insulin defined in HLA-DR4 transgenic mice are derived from preproinsulin and proinsulin. Proc Natl Acad Sci U S A. Mar. 31, 1998;95(7):3833-8.

Di Lorenzo et al., Translational Mini-Review Series on Type 1 Diabetes: Systematic analysis of T cell epitopes in autoimmune diabetes. Clin Exp Immunol. Jan. 22, 2007;148(1):1-16. DOI: 10.1111/j.1365-2249.2006.03244.xView.

Dilthey et al., HLA*IMP—an integrated framework for imputing classical HLA alleles from SNP genotypes. Bioinformatics. Apr. 1, 2011;27(7):968-72. doi: 10.1093/bioinformatics/btr061.

Doolan et al., Use of HLA typing in diagnosing celiac disease in patients with type 1 diabetes. Diabetes Care. Apr. 2005;28(4):806-9.

Durinovic-Bello et al., Predominantly recognized proinsulin T helper cell epitopes in individuals with and without islet cell autoimmunity. J Autoimmun. Feb. 2002;18(1):55-66.

Durinovic-Bello et al., Pro- and anti-inflammatory cytokine production by autoimmune T cells against preproinsulin in HLA-DRB1*04, DQ8 Type 1 diabetes. Diabetologia. Mar. 2004;47(3):439-50.

Ejsing-Duun et al., Dietary gluten reduces the number of intestinal regulatory T cells in mice. Scand J Immunol. Jun. 2008;67(6):553-9. doi: 10.1111/j.1365-3083.2008.02104.x.

Fasano et al., Prevalence of celiac disease in at-risk and not-at-risk groups in the United States: a large multicenter study. Arch Intern Med. Feb. 10, 2003;163(3):286-92.

Ferreira et al., High-density SNP mapping of the HLA region identifies multiple independent susceptibility loci associated with selective IgA deficiency. PLoS Genet. Jan. 2012;8(1):e1002476. doi: 10.1371/journal.pgen.1002476.

Galipeau et al., Sensitization to gliadin induces moderate enteropathy and insulitis in nonobese diabetic-DQ8 mice. J Immunol. Oct. 15, 2011;187(8):4338-46. doi: 10.4049/jimmunol.1100854.

Genbank Submission; NIH/NCBI, Accession No. CAA44688.2; Shapiro; Oct. 7, 2008. 2 pages.

Giuliani et al., Detection of GAD65 autoreactive T-cells by HLA class I tetramers in type 1 diabetic patients. J Biomed Biotechnol. 2009;2009:576219. doi:10.1155/2009/576219.

Han et al., Dietary gluten triggers concomitant activation of CD4+ and CD8+ αβ T cells and γδ T cells in celiac disease. Proc Natl Acad Sci U S A. Aug. 6, 2013;110(32):13073-8.

Henderson et al., A structural and immunological basis for the role of human leukocyte antigen DQ8 in celiac disease. Immunity. Jul. 2007;27(1):23-34.

Herold et al., Type 1 diabetes: translating mechanistic observations into effective clinical outcomes. Nat Rev Immunol. Apr. 2013;13(4):243-56. doi: 10.1038/nri3422.

Hummel et al., Primary dietary intervention study to reduce the risk of islet autoimmunity in children at increased risk for type 1 diabetes: the Babydiet study. Diabetes Care. Jun. 2011;34(6):1301-5. doi: 10.2337/dc10-2456.

Husby et al., European Society for Pediatric Gastroenterology, Hepatology, and Nutrition guidelines for the diagnosis of coeliac disease. J Pediatr Gastroenterol Nutr. Jan. 2012;54(1):136-60. doi: 10.1097/MPG.0b013e31821a23d0.

Kasprowicz et al., A Molecular Assay for Sensitive Detection of Pathogen-Specific T-Cells. PLoS One. 2011; 6(8): e20606.

Katz et al., Screening for celiac disease in a North American population: sequential serology and gastrointestinal symptoms. Am J Gastroenterol. Jul. 2011;106(7):1333-9. doi: 10.1038/ajg.2011.21.

Kern et al., Analysis of CD8 T cell reactivity to cytomegalovirus using protein-spanning pools of overlapping pentadecapeptides. Eur J Immunol. Jun. 2000;30(6):1676-82.

Klemetti et al., T-cell reactivity to wheat gluten in patients with insulin-dependent diabetes mellitus. Scand J Immunol. Jan. 1998;47(1):48-53.

Kumar et al., Reintroduction of gluten in adults and children with treated coeliac disease. Gut. Sep. 1979;20(9):743-9.

Leffler et al., Kinetics of the histological, serological and symptomatic responses to gluten challenge in adults with coeliac disease. Gut. Jul. 2013;62(7):996-1004. doi: 10.1136/gutjnl-2012-302196.

Lequin, Enzyme immunoassay (EIA)/enzyme-linked immunosorbent assay (ELISA). Clin. Chem. Dec. 2005;51(12):2415-8.

Leslie et al., A statistical method for predicting classical HLA alleles from SNP data. Am J Hum Genet. Jan. 2008;82(1):48-56. doi: 10.1016/j.ajhg.2007.09.001.

Luster et al., Biochemical characterization of a gamma interferon-inducible cytokine (IP-10). J Exp Med. Oct. 1, 1987;166(4):1084-97.

Mallone et al., T cell recognition of autoantigens in human type 1 diabetes: clinical perspectives. Clin Dev Immunol. 2011;2011:513210. doi: 10.1155/2011/513210.

(56) References Cited

OTHER PUBLICATIONS

Molberg et al., T cells from celiac disease lesions recognize gliadin epitopes deamidated in situ by endogenous tissue transglutaminase. Eur J Immunol. May 2001;31(5):1317-23.

Monsuur et al., Effective detection of human leukocyte antigen risk alleles in celiac disease using tag single nucleotide polymorphisms. PLoS One. May 28, 2008;3(5):e2270. doi: 10.1371/journal.pone.0002270.

Nguyen et al., Definition of high-risk type 1 diabetes HLA-DR and HLA-DQ types using only three single nucleotide polymorphisms. Diabetes. Jun. 2013;62(6):2135-40. doi: 10.2337/db12-1398.

Ontiveros et al., Ex-vivo whole blood secretion of interferon (IFN)-γ and IFN-γ-inducible protein-10 measured by enzyme-linked immunosorbent assay are as sensitive as IFN-γ enzyme-linked immunospot for the detection of gluten-reactive T cells in human leucocyte antigen (HLA)-DQ2·5(+)-associated coeliac disease. Clin Exp Immunol. Feb. 2014;175(2):305-15. doi: 10.1111/cei.12232.

Pathiraja et al., Proinsulin-specific, HLA-DQ8, and HLA-DQ8-transdimer-restricted CD4+ T cells infiltrate islets in type 1 diabetes. Diabetes. Jan. 2015;64(1):172-82. doi: 10.2337/db14-0858.

Raju et al., T cell recognition of human pre-proinsulin peptides depends on the polymorphism at HLA DQ locus: a study using HLA DQ8 and DQ6 transgenic mice. Hum Immunol. Nov. 1997;58(1):21-9.

Raki et al., Tetramer visualization of gut-homing gluten-specific T cells in the peripheral blood of celiac disease patients. Proc Natl Acad Sci U S A. Feb. 20, 2007;104(8):2831-6.

Rostom et al., Institute technical review on the diagnosis and management of celiac disease. Gastroenterology. Dec. 2006;131(6):1981-2002.

Sarugeri et al., T cell responses to type 1 diabetes related peptides sharing homologous regions. J Mol Med (Berl). May 2001;79(4):213-20.

Simell et al., Age at development of type 1 diabetes- and celiac disease-associated antibodies and clinical disease in genetically susceptible children observed from birth. Diabetes Care. Apr. 2010;33(4):774-9. doi: 10.2337/dc09-1217.

Smyth et al., Shared and distinct genetic variants in type 1 diabetes and celiac disease. N Engl J Med. Dec. 25, 2008;359(26):2767-77. doi: 10.1056/NEJMoa0807917.

Sollid et al., Nomenclature and listing of celiac disease relevant gluten T-cell epitopes restricted by HLA-DQ molecules. Immunogenetics. Jun. 2012;64(6):455-60. doi: 10.1007/s00251-012-0599-z. Epub Feb. 10, 2012.

Sollid et al., Novel therapies for coeliac disease. J Intern Med. Jun. 2011;269(6):604-13. doi: 10.1111/j.1365-2796.2011.02376.x.

Triolo et al., Additional autoimmune disease found in 33% of patients at type 1 diabetes onset. Diabetes Care. May 2011;34(5):1211-3. doi: 10.2337/dc10-1756.

Tye-Din et al., Comprehensive, quantitative mapping of T cell epitopes in gluten in celiac disease. Sci Transl Med. Jul. 21, 2010;2(41):1-14.

Tye-Din et al., Supplementary Materials for Comprehensive, quantitative mapping of T cell epitopes in gluten in celiac disease. Sci Transl Med. Jul. 21, 2010;2(41):41ra51.

Vader et al., Specificity of tissue transglutaminase explains cereal toxicity in celiac disease. J Exp Med. Mar. 4, 2002;195(5):643-9.

White et al., Effects of in vivo administration of interleukin-2 (IL-2) and IL-4, alone and in combination, on ex vivo human basophil histamine release. Blood. Mar. 15, 1992;79(6):1491-5.

Yang et al., CD4+ T cells recognize diverse epitopes within GAD65: implications for repertoire development and diabetes monitoring. Immunology. Mar. 2013;138(3):269-79. for doi: 10.1111/imm.12034.

Atkinson et all., The pathogenesis and natural history of type 1 diabetes. Cold Spring Harbor perspectives in medicine 2012;2.

Bakker et al., Frequent delay of coeliac disease diagnosis in symptomatic patients with type 1 diabetes mellitus: clinical and genetic characteristics. Eur J Intern Med. Jul. 2013;24(5):456-60. doi: 10.1016/j.ejim.2013.01.016.

Baumgart et al., Transient cytokine-induced liver injury following administration of the humanized anti-CD3 antibody visilizumab (HuM291) in Crohn's disease. Am J Gastroenterol. Apr. 2009;104(4):868-76. doi: 10.1038/ajg.2008.138.

Bunce et al., Phototyping: comprehensive DNA typing for HLA-A, B, C, DRB1, DRB3, DRB4, DRB5 & DQB1 by PCR with 144 primer mixes utilizing sequence-specific primers (PCR-SSP). Tissue Antigens. Nov. 1995;46(5):355-67.

Cassatella et al., Regulated production of the interferon-gamma-inducible protein-10 (IP-10) chemokine by human neutrophils. Eur J Immunol. Jan. 1997;27(1):111-5.

Chakera et al., A whole blood monokine-based reporter assay provides a sensitive and robust measurement of the antigen-specific T cell response. J Transl Med. Aug. 26, 2011;9:143. doi: 10.1186/1479-5876-9-143.

Chatenoud et al., In vivo cell activation following OKT3 administration. Systemic cytokine release and modulation by corticosteroids. Transplantation. Apr. 1990;49(4):697-702.

Czerkinsky et al., A solid-phase enzyme-linked immunospot (ELISPOT) assay for enumeration of specific antibody-secreting cells. J Immunol Methods. Dec. 16, 1983;65(1-2):109-21.

Dicke et al., Coeliac disease. II. The presence in wheat of a factor having a deleterious effect in cases of coeliac disease. Acta Paediatr. Jan. 1953;42(1):34-42.

Genbank Submission; NIH/NCBI, Accession No. AAA58491.1; Karlsenet al.; Dec. 31, 1994. 2 pages.

Genbank Submission; NIH/NCBI, Accession No. AAA59172.1; Bell et al.; Jun. 10, 2016; 2 pages.

Genbank Submission; NIH/NCBI, Accession No. AAA59173.1;Cao et al.; Oct. 25, 1999. 2 pages.

Genbank Submission; NIH/NCBI, Accession No. AAA59179.1; Lucassen et al.; Jan. 6, 1995. 1 page.

Genbank Submission; NIH/NCBI, Accession No. AAA62367.1; Bu et al.; Feb. 23, 1995. 2 pages.

Genbank Submission; NIH/NCBI, Accession No. AAB28987.1; Kim et al.; Feb. 26, 1994. 1 page.

Genbank Submission; NIH/NCBI, Accession No. AAH05255.1; Strausberg et al.; Jun. 23, 2006. 2 pages.

Genbank Submission; NIH/NCBI, Accession No. AAI26328.1; Strausberg et al.; Mar. 19, 2007. 2 pages.

Genbank Submission; NIH/NCBI, Accession No. AAI26330.1; Strausberg et al.; Mar. 19, 2007. 2 pages.

Genbank Submission; NIH/NCBI, Accession No. AAN39451.1; Stead et al.; Jun. 10, 2016. 1 page.

Genbank Submission; NIH/NCBI, Accession No. AAP35454.1; Kalnine et al.; May 13, 2003. 2 pages.

Genbank Submission; NIH/NCBI, Accession No. AAP88040.1; Swarbrick et al.; Nov. 4, 2009. 2 pages.

Genbank Submission; NIH/NCBI, Accession No. AAW83741.1; Shalevet al.; Feb. 15, 2005. 2 pages.

Genbank Submission; NIH/NCBI, Accession No. ABI63346.1; Yuet al.; Jul. 7, 2007. 1 pages.

Genbank Submission; NIH/NCBI, Accession No. AEG19452.1; Piriet al.; May 29, 2011. 2 pages.

Genbank Submission; NIH/NCBI, Accession No. AFK93533.1; Piriet al.; Jun. 9, 2012. 2 pages.

Genbank Submission; NIH/NCBI, Accession No. CAA08766.1; Fajardy et al.; Jul. 26, 2018. 3 pages.

Genbank Submission; NIH/NCBI, Accession No. CAA23828.1; Bell; Mar. 30, 1995. 3 pages.

Genbank Submission; NIH/NCBI, Accession No. CAA49554.1; Mauchet al.; Mar. 16, 1993. 2 pages.

Genbank Submission; NIH/NCBI, Accession No. CAA49913.1; Chekhranovaet al.; Oct. 7, 2008. 2 pages.

Genbank Submission; NIH/NCBI, Accession No. CAB62572.1; Santos et al.; Jul. 26, 2016. 2 pages.

Genbank Submission; NIH/NCBI, Accession No. CAC09233.1; Clare-Salzler al.; Sep. 16, 2000. 1 page.

(56) References Cited

OTHER PUBLICATIONS

Genbank Submission; NIH/NCBI, Accession No. CAH73658.1; Collins; May 6, 2008. 2 pages.
Genbank Submission; NIH/NCBI, Accession No. CAH73659.1; Collins; May 6, 2008. 2 pages.
Genbank Submission; NIH/NCBI, Accession No. CAH73660.1; Collins; May 6, 2008. 2 pages.
Genbank Submission; NIH/NCBI, Accession No. EAW86101.1; Venter et al.; Mar. 23, 2015. 2 pages.
Genbank Submission; NIH/NCBI, Accession No. EAW86102.1; Venter et al.; Mar. 23, 2015. 3 pages.
Genbank Submission; NIH/NCBI, Accession No. EAW86103.1; Venter et al.; Mar. 23, 2015. 3 pages.
Genbank Submission; NIH/NCBI, Accession No. EAW86104.1; Venter et al.; Mar. 23, 2015. 3 pages.
Genbank Submission; NIH/NCBI, Accession No. NP_000198.1; Elliset al.; Apr. 19, 2014. 3 pages.
Genbank Submission; NIH/NCBI, Accession No. NP_000809.1; Schwabet al.; Feb. 26, 2014. 4 pages.
Genbank Submission; NIH/NCBI, Accession No. NP_001127838.1; Schwabet al.; Feb. 2, 2014. 4 pages.
Genbank Submission; NIH/NCBI, Accession No. NP_001172026.1; Elliset al.; Apr. 20, 2014. 3 pages.
Genbank Submission; NIH/NCBI, Accession No. NP_001172027.1; Elliset al.; Apr. 13, 2014. 3 pages.
Genbank Submission; NIH/NCBI, Accession No. NP_001186692.1; Longet al.; Mar. 16, 2014. 3 pages.
Genbank Submission; NIH/NCBI, Accession No. NP_001186693.1; Longet al.; Feb. 27, 2014. 3 pages.
Genbank Submission; NIH/NCBI, Accession No. P01308.1; Bellet al.; Apr. 16, 2014. 13 pages.
Genbank Submission; NIH/NCBI, Accession No. Q05329.1; Karlsenet al.; Apr. 16, 2014. 8 pages.
Genbank Submission; NIH/NCBI, Accession No. Q16849.1; Lanet al.; Apr. 16, 2014. 9 pages.
Genbank Submission; NIH/NCBI, Accession No. Q5VZ30; Chapman; Oct. 31, 2006. 2 pages.
Genbank Submission; NIH/NCBI, Prf No. 0601246A; Bell et al.; Jun. 19, 1996; 1 page.
Green et al., Celiac disease. N Engl J Med. Oct. 25, 2007;357(17):1731-43.
Karell et al., HLA types in celiac disease patients not carrying the DQA1*05-DQB1*02 (DQ2) heterodimer: results from the European Genetics Cluster on Celiac Disease. Hum Immunol. Apr. 2003;64(4):469-77.
Koskinen et al., Cost-effective HLA typing with tagging SNPs predicts celiac disease risk haplotypes in the Finnish, Hungarian, and Italian populations. Immunogenetics. Apr. 2009;61(4):247-56. doi: 10.1007/s00251-009-0361-3.
Maecker et al., Use of overlapping peptide mixtures as antigens for cytokine flow cytometry. J Immunol Methods. Sep. 1, 2001;255(1-2):27-40.
Morahan et al., The genetics of type 1 diabetes. In the HLA Complex in Biology and Medicine: A Resource Book. Mehra NK, Ed., New Delhi, JayPee Brothers Publishing, 2010, p. 205-218.
Mullighan et al., High-resolution HLA-DQB1 typing using the polymerase chain reaction and sequence-specific primers. Tissue Antigens. Dec. 1997;50(6):688-92.
Olerup et al., HLA-DQB1 and -DQA1 typing by PCR amplification with sequence-specific primers (PCR-SSP) in 2 hours. Tissue Antigens. Mar. 1993;41(3):119-34.
Qin et al., "Infectious" transplantation tolerance. Science. Feb. 12, 1993;259(5097):974-7.
Sanjeevi et al., DR4 subtypes and their molecular properties in a population-based study of Swedish childhood diabetes. Tissue Antigens. Apr. 1996;47(4):275-83.
Sildorf et al., Remission without insulin therapy on gluten-free diet in a 6-year old boy with type 1 diabetes mellitus. BMJ Case Rep. Jun. 21, 2012;2012. pii: bcr0220125878. doi: 10.1136/bcr.02.2012.5878.
Tye-Din. Gluten peptides recognized by T cells in coeliac disease. Doctoral Thesis. University of Melbourne 2008.
Van De Kamer et al., Coeliac disease. IV. An investigation into the injurious constituents of wheat in connection with their action on patients with coeliac disease. Acta Paediatr. May 1953;42(3):223-31.
Supplementary European Search Report dated Jan. 22, 2019 in connection with Application No. EP 15816558.9.

\* cited by examiner

PEPTIDES FOR USE IN TREATMENT AND DIAGNOSIS OF TYPE 1 DIABETES

RELATED APPLICATIONS

This application is a national stage filing under 35 U.S.C. § 371 of International Application No. PCT/US2015/061931, filed Nov. 20, 2015, entitled "PEPTIDES FOR USE IN TREATMENT AND DIAGNOSIS OF TYPE 1 DIABETES," which claims the benefit of 35 U.S.C. § 119 (e) of U.S. provisional application No. 62/082,823, filed Nov. 21, 2014, the contents of each of which are incorporated by reference in their entirety.

BACKGROUND OF THE INVENTION

Type 1 Diabetes (T1D) is a form of diabetes mellitus that results from the destruction of insulin-producing beta cells in the pancreas due to an autoimmune response to the beta cells. Approximately 350 million people worldwide have diabetes, about 5-10% of which have T1D. There is no cure for T1D currently, with T1D management requiring lifelong use of insulin.

SUMMARY OF THE INVENTION

The disclosure relates to compositions and methods for treating subjects having autoimmune diabetes, such as T1D, assessing efficacy of treatment, diagnosing autoimmune diabetes, such as T1D, and selecting subjects for treatment. As described herein, peptides were identified as inducing a T cell response as measured by IP-10 secretion when contacted with whole blood from subjects having T1D and Celiac disease. Without wishing to be bound by theory, the T cells are believed to be disease-causative CD4+ T cells specific for epitopes contained within the peptides. Accordingly, peptides containing such epitopes are useful, e.g., to diagnose autoimmune diabetes such as T1D, to treat autoimmune diabetes such as T1D (e.g., by tolerizing T cells specific for the epitopes in the peptides), to select subjects for treatment, and to assess efficacy of treatment.

Aspects of the disclosure relate to a composition, comprising at least one peptide, the at least one peptide comprising at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence. In some embodiments of any one of the compositions provided, the at least one T cell epitope contained within the at least one amino acid sequence comprises an amino acid sequence LLALLALWGPD (SEQ ID NO: 14).

In some embodiments of any one of the compositions provided, the composition comprises at least two peptides, wherein a first peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence; and a second peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence. In some embodiments of any one of the compositions provided, the at least one T cell epitope contained within the at least one amino acid sequence of the first or second peptide comprises an amino acid sequence LLALLALWGPD (SEQ ID NO: 14).

In some embodiments of any one of the compositions provided, the composition comprises at least three peptides, wherein a first peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence; a second peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence; and a third peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence. In some embodiments of any one of the compositions provided, the at least one T cell epitope contained within the at least one amino acid sequence of the first, second or third peptide comprises an amino acid sequence LLALLALWGPD (SEQ ID NO: 14).

In some embodiments of any one of the compositions provided, at least one of the peptides comprises a modification on the N-terminus and/or C-terminus. In some embodiments of any one of the compositions provided, at least one of the peptides comprises an N-terminal pyroglutamate or acetyl group and/or a C-terminal amide group. In some embodiments of any one of the compositions provided, each of the peptides comprises an N-terminal pyroglutamate or acetyl group and/or a C-terminal amide group.

In some embodiments of any one of the compositions provided, each of the peptides is independently between 8 to 50 amino acids in length. In some embodiments of any one of the compositions provided, each of the peptides is independently between 8 to 30 amino acids in length. In some embodiments of any one of the compositions provided, each of the peptides is independently between 8 to 20 amino acids in length. In some embodiments of any one of the compositions provided, each of the peptides is independently between 8 to 18 amino acids in length. In some embodiments of any one of the compositions provided, each of the peptides is independently no more than 20 amino acids in length. In some embodiments of any one of the compositions provided, each of the peptides is independently no more than 18 amino acids in length.

In some embodiments of any one of the compositions provided, the at least one, two or three peptide(s), or each of the at least one, two or three peptide(s), is not TPKTRREAEDLQVGQVEL (SEQ ID NO: 15), TPKTRREAEDLQVGQVELGGGP (SEQ ID NO: 16), MALWMRLLPLLALLALWGPDPAAA (SEQ ID NO: 17), MRLLPLLALLALWGPDPAAA (SEQ ID NO: 18), GERGFFYTPKTRREAEDLQV (SEQ ID NO: 19), TPKTRREAEDLQV (SEQ ID NO: 20), EDLQVGQVELGGGPGA (SEQ ID NO: 21), EAEDLQVGQVELGGGPGAGSLQPLALEGSLQ (SEQ ID NO: 22), RREAEDLQVGQVELGGGPGAGSLQPLALEGSLQKR (SEQ ID NO: 23), RREAEDLQVGQVELGGGPGAGSLQPLALEGSLQAR (SEQ ID NO: 24), HLCGSHLVEALYLVCGERGFF (SEQ ID NO: 25), FVNQHLCGSHLVEALYLVCGERGFFYTPKT (SEQ ID NO: 26), FVNQHLCGSHLVEALYLVCGERGFFYTPKPT (SEQ ID NO: 27), FVNQHLCGSHLVEALYLVC (SEQ ID NO: 28), FVNQHLCGSHLVEALYLVCGERG (SEQ ID NO: 29), FVNQHLCGSHLVEALYLVCGERGFFP (SEQ ID NO: 30), FVNQHLCGSHLVEALYLVCGERGFFYTPK (SEQ ID NO: 31), FVNQHLCGSHLVEALYLVCGERGFFYTPKT (SEQ ID NO: 26), TNMFTYEIAPVFVLLEYVTL (SEQ ID NO: 32) or GERGFFYTPKTRREAEDLQV (SEQ ID NO: 19).

In some embodiments of any one of the compositions provided, the composition further comprises a pharmaceutically acceptable carrier. In some embodiments of any one of the compositions provided, at least one of the peptides is bound to a) an HLA molecule, or b) a fragment of an HLA molecule, capable of binding the peptide.

In some embodiments of any one of the compositions, peptides, methods, kits, or antigen presenting cells provided=, the at least one T cell epitope is not a CD8+ T cell epitope. In some embodiments of any one of the compositions, peptides, methods, kits, or antigen presenting cells provided, the at least one T cell epitope does not comprise LPLLALLAL (SEQ ID NO: 76).

Other aspects of the disclosure relate to a composition comprising one or more polynucleotides encoding the peptides of any one of the compositions described herein.

Yet other aspects of the disclosure relate to an isolated antigen presenting cell comprising any one of the compositions described herein.

Other aspects of the disclosure relate to a kit comprising any one of the compositions described herein and at least one means to detect binding of one or more of the peptides in the composition to T cells. In some embodiments of any one of the kits, the at least one means to detect binding of one or more of the peptides in the composition to T cells is an antibody specific for a cytokine. In some embodiments of any one of the kits, the cytokine is selected from IFN-gamma, IL-2 or IP-10. In some embodiments of any one of the kits, the cytokine is IL-2 and IP-10. In some embodiments of any one of the kits, the cytokine is IFN-gamma, IL-2 and IP-10.

Another aspect of the disclosure relates to a method for treating type 1 diabetes (T1D) in a subject, the method comprising administering to a subject having or suspected of having T1D an effective amount of any one of the compositions described herein or any one of the antigen presenting cells described herein.

Other aspects of the disclosure relate to a method for identifying a subject as having or at risk of T1D, the method comprising determining a T cell response to any one of the compositions described herein or any one of the antigen presenting cells described herein in a sample comprising a T cell from the subject; and assessing whether or not the subject has or is at risk of having T1D.

In some embodiments of any one of the methods provided, the assessing comprises identifying the subject as (i) having or at risk of having T1D if the T cell response to the composition is elevated compared to a control T cell response, or (ii) not having or not at risk of having T1D if the T cell response to the composition is reduced compared to the control T cell response or the same as the control T cell response.

In some embodiments of any one of the methods provided, the step of determining comprises contacting the sample with the composition and measuring a T cell response to the composition. In some embodiments of any one of the methods provided, the sample is contacted with a composition comprising 0.4 micrograms/mL, 1 microgram/mL, 4 micrograms/mL, 5 micrograms/mL, 10 micrograms/mL, 20 micrograms/mL, 25 micrograms/mL, or 50 micrograms/mL of at least one peptide as described herein.

In some embodiments of any one of the methods provided, measuring a T cell response to the composition comprises measuring a level of at least one cytokine in the sample. In some embodiments of any one of the methods provided, the at least one cytokine is IFN-gamma, IL-2 or IP-10. In some embodiments of any one of the methods provided, the at least one cytokine is IL-2 and IP-10. In some embodiments of any one of the methods provided, the at least one cytokine is IFN-gamma, IL-2 and IP-10.

In some embodiments of any one of the methods provided, measuring comprises an enzyme-linked immunosorbent assay (ELISA), an enzyme-linked immunosorbent spot (ELISpot) assay, or a multiplex bead-based immunoassay. In some embodiments of any one of the methods provided, the sample comprises whole blood or peripheral blood mononuclear cells. In some embodiments of any one of the methods provided, the sample comprising a T cell comprises fresh blood from the subject. In some embodiments of any one of the methods provided, the sample is contacted with the composition for about 18 to about 30 hours, e.g., about 24 hours. In some embodiments of any one of the methods provided, the sample is contacted with the composition in a 96-well plate.

In some embodiments of any one of the methods provided, the method further comprises treating the subject if identified as having or at risk of having T1D or providing information to the subject about a treatment. In some embodiments of any one of the methods provided, the subject has T1D and Celiac disease.

Other aspects of the disclosure relate to a method for assessing the efficacy of treatment of Type I Diabetes in a subject, the method comprising: (a) measuring a T cell response to any one of the compositions described herein or any one of the antigen presenting cells described herein in a sample from a subject that has been administered a tolerogenic treatment; and (b) assessing the efficacy based on the measuring.

In some embodiments of any one of the methods provided, the method further comprises (c) treating the subject, or suggesting a treatment to the subject, based on the assessing. In some embodiments of any one of the methods provided, the method further comprises administering the tolerogenic treatment. In some embodiments of any one of the methods provided, the tolerogenic treatment is any one of the compositions described herein or any one of the antigen presenting cells described herein.

In some embodiments of any one of the methods provided, the treating comprises continuing with the treatment, or the suggesting comprises suggesting the subject continue with the treatment, based on the assessing if the assessing indicates the T cell response is at or above a control T cell response. In some embodiments of any one of the methods provided, the treating comprises ceasing the treatment, or the suggesting comprises suggesting the subject cease the treatment, based on the assessing; if the assessing indicates the T cell response is below a control T cell response. In some embodiments of any one of the methods provided, the treating comprises administering a different or additional treatment, or the suggesting comprises suggesting the subject be treated with an additional or different treatment, based on the assessing, if the assessing indicates the T cell response is below a control T cell response.

In some embodiments of any one of the methods provided, the T cell response to the composition or antigen presenting cell is measured by measuring a level of at least one cytokine secreted by a T cell in a sample from the subject after the sample has been contacted with the composition or antigen presenting cell. In some embodiments of any one of the methods provided, the at least one cytokine is IFN-gamma, IL-2, or IP-10. In some embodiments of any one of the methods provided, the at least one cytokine is IL-2 and IP-10. In some embodiments of any one of the methods provided, the at least one cytokine is IFN-gamma, IL-2 and IP-10.

In some embodiments of any one of the methods provided, the sample comprises fresh blood from the subject. In some embodiments of any one of the methods provided, the sample is contacted with the composition for about 18 to about 30 hours, e.g., about 24 hours. In some embodiments of any one of the methods provided, the sample is contacted with the composition in a 96-well plate.

In some embodiments of any one of the methods provided, the subject has T1D and Celiac disease.

Other aspects of the disclosure relate to a method for selecting a subject having Type I Diabetes for treatment, the method comprising: (a) measuring a T cell response to any one of the compositions described herein or any one of the antigen presenting cells described herein in a sample from a subject having Type I Diabetes; and (b) treating the subject, or suggesting a treatment to the subject if the T cell response is at or above a control T cell response.

In some embodiments of any one of the methods provided, the treatment is administration of the composition or antigen present cell to the subject.

In some embodiments of any one of the methods provided, the T cell response to the composition or antigen presenting cell is measured by measuring a level of at least one cytokine secreted by a T cell in a sample from the subject after the sample has been contacted with the composition or antigen presenting cell. In some embodiments of any one of the methods provided, the at least one cytokine is IFN-gamma, IL-2 or IP-10. In some embodiments of any one of the methods provided, the at least one cytokine is IL-2 and IP-10. In some embodiments of any one of the methods provided, the at least one cytokine is IFN-gamma, IL-2 and IP-10.

In some embodiments of any one of the methods provided, the sample comprises fresh blood from the subject. In some embodiments of any one of the methods provided, the sample is contacted with the composition for about 18 to about 30 hours, e.g., about 24 hours. In some embodiments of any one of the methods provided, the sample is contacted with the composition in a 96-well plate.

In some embodiments of any one of the methods provided, the subject has T1D and Celiac disease.

In some embodiments of any one of the compositions, peptides, methods, kits, or antigen presenting cells provided herein, any of the peptides or epitopes in the Examples or Figures is contemplated for use.

The details of one or more embodiments of the disclosure are set forth in the description below. Other features or advantages of the present disclosure will be apparent from the following drawings and detailed description of several embodiments, and also from the appending claims.

DETAILED DESCRIPTION OF THE INVENTION

Figure 1A:
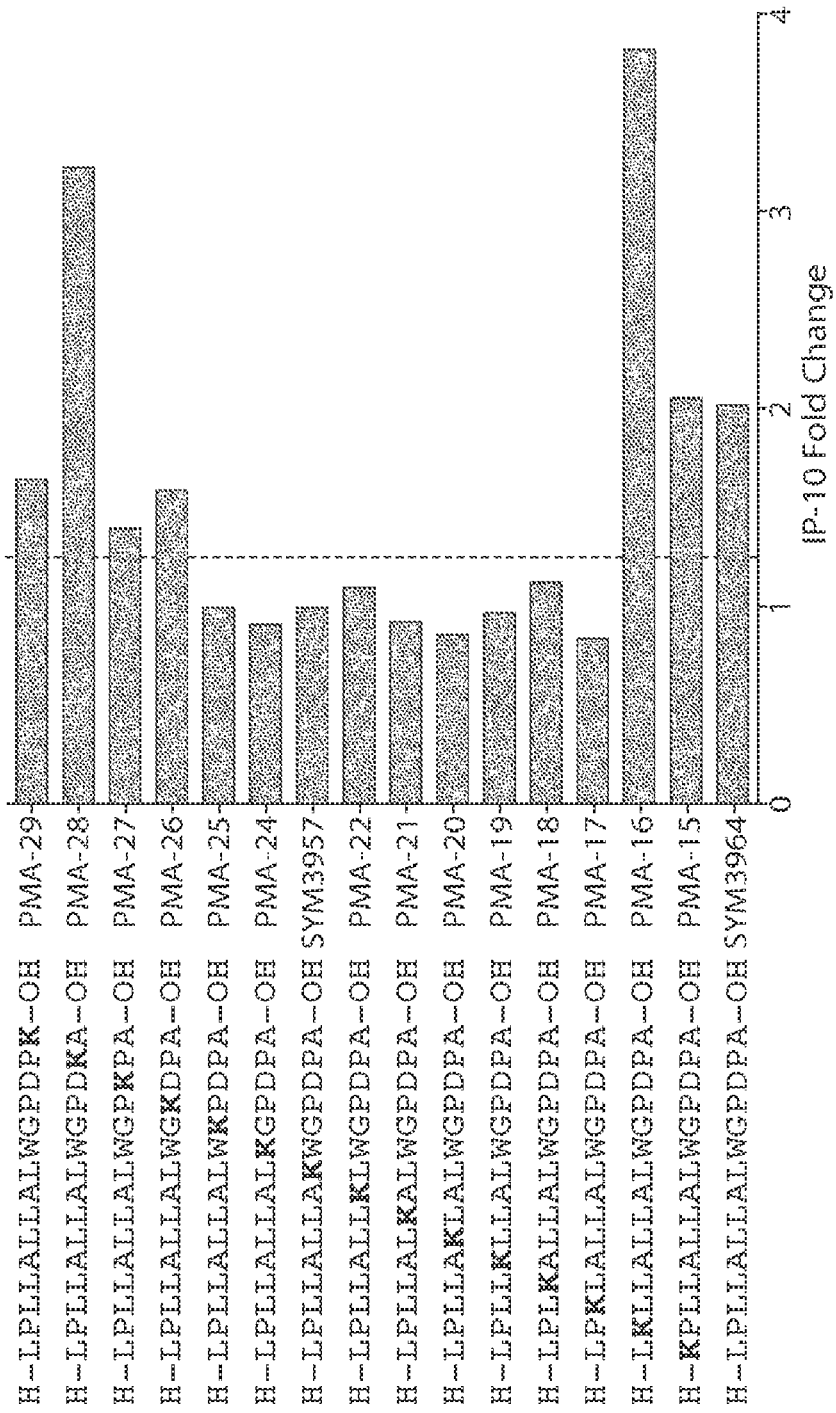
FIG. 1A-FIG. 1C are graphs depicting length and observed bioactivity in a whole blood IP-10 release assay in 4 subjects with T1D for the fine epitope mapping of the dominant 11mer epitope in preproinsulin p10-20: LLAL-LALWGPD (SEQ ID NO: 14). The data are the averages of 4 subjects whole blood IP-10 release measured as fold change over medium alone without peptide. SEQ ID NOs: 82-97 appear in FIG. 1A from top to bottom, respectively. SEQ ID NOs: 75-81 appear in FIG. 1B from top to bottom, respectively. SEQ ID NOs: 98-104 and 97 appear in FIG. 1C from top to bottom, respectively.

Type 1 Diabetes (T1D) is a form of diabetes mellitus that results from the destruction of insulin-producing beta cells in the pancreas due to an autoimmune response to the beta cells. Subjects with T1D may possess HLA-DR3, HLA-DR4, HLA-DQ2 and/or HLA-DQ8 susceptibility alleles. Without wishing to be bound by theory, it is believed that such individuals mount an inappropriate CD4+ T cell-mediated immune response to HLA-DR3, HLA-DR4-, HLA-DQ2- and/or HLA-DQ8-restricted epitopes present in autoantigens, leading to the destruction of the beta cells. As described herein, a peptide screen was performed to identify peptides having epitopes that cause CD4+ T cell responses, e.g., as measured by IP-10 secretion in a whole blood assay. Several peptides were identified as having epitopes that elicited a T cell response upon contact with whole blood obtained from subjects having T1D and Celiac disease. The T cell response did not change before and after gluten challenge, unlike T cell responses to gluten peptides in the same subjects, indicating that these peptides may also be used to treat autoimmune diabetes (e.g., T1D) in subjects that do not have Celiac disease.

Accordingly, the disclosure provides compositions, kits and methods related to treating autoimmune diabetes (e.g., T1D), diagnosing autoimmune diabetes (e.g., T1D), assessing efficacy of treatment of autoimmune diabetes (e.g., T1D), and selecting subjects for treatment of autoimmune diabetes (e.g., T1D).

Peptides and Compositions Containing Peptides

Aspects of the disclosure relate to peptides and uses of peptides in compositions, methods, kits, etc.

In some embodiments of any one of the compositions, peptides, methods, kits, or antigen presenting cells provided herein, at least one peptide (e.g., 1, 2, 3 or more peptides) is provided, the at least one peptide comprising at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence. In some embodiments, the at least one T cell epitope contained within the at least one amino acid sequence comprises an amino acid sequence LLALLALWGPD (SEQ ID NO: 14). In some embodiments, the at least one peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), or PKAARPPVTPVLLEKKS (SEQ ID NO: 13). In some embodiments, each of the at least one peptides are independently at least 8 or 9 amino acids in length. In some embodiments, each of the at least one peptides are independently between 8 to 50 amino acids in length. In some embodiments, each of the at least one peptides are independently between 8 to 30 amino acids in length. In some embodiments, each of the at least one peptides are independently between 10 to 30 amino acids in length. In some embodiments, each of the at least one peptides are independently 8 to 20 amino acids in length. In some embodiments, each of the at least one peptides are independently 10 to 20 amino acids in length. In some embodiments, each of the at least one peptides are independently between 8 to 19 amino acids in length. In some embodiments, each of the at least one peptides are independently between 10 to 19 amino acids in length. In some embodiments, each of the at least one peptides are independently between 8 to 18, 8 to 17, 8 to 16, 8 to 15, 8 to 14, 8 to 13, 8 to 12, or 8 to 11 amino acids in length. In some embodiments, each of the at least one peptides are independently between 10 to 18 amino acids in length. In some embodiments, each of the at least one peptides are independently no more than 20 amino acids in length. In some embodiments, each of the at least one peptides are independently no more than 18 amino acids in length.

The at least one T cell epitope contained within the at least one amino acid sequence described herein may be identified by any method known in the art or described herein. For example, an alanine or lysine scan (e.g., by substitution of each amino acid position with an alanine or lysine or, if the amino acid at the position is already alanine, a non-conservative amino acid) of a peptide containing an amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), or PKAARPPVTPVLLEKKS (SEQ ID NO: 13) may be used to determine shorter amino acid sequences within the peptide that result in a T cell response as described herein, e.g., that result in IP-10 release upon contact of T cells with the alanine- or lysine-substituted peptide. Serial single-amino acid truncations from the N- and C-termini of immunoreactive sequences may also be used to determine core sequences of epitopes, typically, e.g., 9-amino acids in length, which are critical for T cell recognition. Individual T cell clones raised from T1D-patient blood may be used to further determine the restriction of individual epitopes confirming minimal core sequences.

In some embodiments, the at least one peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), or PKAARPPVTPVLLEKKS (SEQ ID NO: 13). In some embodiments of any one of the compositions, peptides, methods, kits, or antigen presenting cells provided herein, the at least one peptide comprises at least one amino acid sequence selected from any one of the sequences provided in the Examples or in the Figures. In some embodiments, each of the at least one peptides are independently at least 8 or 9 amino acids in length. In some embodiments, each of the at least one peptides are independently between 8 to 50 amino acids in length. In some embodiments, each of the at least one peptides are independently between 8 to 30 amino acids in length. In some embodiments, each of the at least one peptides are independently between 10 to 30 amino acids in length. In some embodiments, each of the at least one peptides are independently 8 to 20 amino acids in length. In some embodiments, each of the at least one peptides are independently 10 to 20 amino acids in length. In some embodiments, each of the at least one peptides are independently between 8 to 19 amino acids in length. In some embodiments, each of the at least one peptides are independently between 10 to 19 amino acids in length. In some embodiments, each of the at least one peptides are independently between 8 to 18, 8 to 17, 8 to 16, 8 to 15, 8 to 14, 8 to 13, 8 to 12, or 8 to 11 amino acids in length. In some embodiments, each of the at least one peptides are independently between 10 to 18 amino acids in length. In some embodiments, each of the at least one peptides are independently no more than 20 amino acids in length. In some embodiments, each of the at least one peptides are independently no more than 18 amino acids in length.

In some embodiments of any one of the compositions, peptides, methods, kits, or antigen presenting cells provided herein, at least two peptides are provided (e.g., 2, 3 or more peptides), wherein a first peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or a T cell epitope contained within the at least one amino acid sequence, and a second peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or a T cell epitope contained within the at least one amino acid sequence, wherein the sequence of the first peptide and the second peptide differ by one or more amino acids. In some embodiments of any one of the compositions, peptides, methods, kits, or antigen presenting cells provided herein, at least two peptides are provided, a first peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or a T cell epitope contained within the at least one amino acid sequence; a second peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or a T cell epitope contained within the at least one amino acid sequence; and a third peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or a T cell epitope contained within the at least one amino acid sequence, wherein the sequence of the first peptide, the second peptide and the third peptide differ from each other by one or more amino acids. In some embodiments of any one of the compositions, peptides, methods, kits, or antigen presenting cells provided herein, at least two peptides are provided (e.g., 2, 3 or more peptides), wherein a first peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), or PKAARPPVTPVLLEKKS (SEQ ID NO: 13), and a second peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), or PKAARPPVTPVLLEKKS (SEQ ID NO: 13), wherein the sequence of the first peptide and the second peptide differ by one or more amino acids. In some embodiments of any one of the compositions, peptides, methods, kits, or antigen presenting cells provided herein, the at least one T cell epitope contained within the at least one amino acid sequence comprises an amino acid sequence LLALLALWGPD (SEQ ID NO: 14). Therefore, any one of the peptides described herein (e.g., first, second or third peptide) may comprise an amino acid sequence LLALLALWGPD (SEQ ID NO: 14). In some embodiments, each of the at least two peptides are independently at least 8 or 9 amino acids in length. In some embodiments, each of the at least one peptides are independently between 8 to 50 amino acids in length. In some embodiments, each of the at least one peptides are independently between 8 to 30 amino acids in length. In some embodiments, each of the at least one peptides are independently between 10 to 30 amino acids in length. In some embodiments, each of the at least one peptides are independently 8 to 20 amino acids in length. In some embodiments, each of the at least one peptides are independently 10 to 20 amino acids in length. In some embodiments, each of the at least one peptides are independently between 8 to 19 amino acids in length. In some embodiments, each of the at least one peptides are independently between 10 to 19 amino acids in length. In some embodiments, each of the at least one peptides are independently between 8 to 18, 8 to 17, 8 to 16, 8 to 15, 8 to 14, 8 to 13, 8 to 12, or 8 to 11 amino acids in length. In some embodiments, each of the at least one peptides are independently between 10 to 18 amino acids in length. In some embodiments, each of the at least one peptides are independently no more than 20 amino acids in length. In some embodiments, each of the at least one peptides are independently no more than 18 amino acids in length.

In some embodiments of any one of the compositions, peptides, methods, kits, or antigen presenting cells provided herein, the at least one peptide is not TPKTRREAE-DLQVGQVEL (SEQ ID NO: 15), TPKTRREAE-DLQVGQVELGGGP (SEQ ID NO: 16), MALWMRLLPL-LALLALWGPDPAAA (SEQ ID NO: 17), MRLLPLLALLALWGPDPAAA (SEQ ID NO: 18), GERGFFYTPKTRREAEDLQV (SEQ ID NO: 19), TPK-TRREAEDLQV (SEQ ID NO: 20), EDLQVGQVELGGG-PGA (SEQ ID NO: 21), EAEDLQVGQVELGGGPGAG-SLQPLALEGSLQ (SEQ ID NO: 22), RREAEDLQVGQVELGGGPGAGSLQPLALEGSLQKR (SEQ ID NO: 23), RREAEDLQVGQVELGGGPGAGSLQ-PLALEGSLQAR (SEQ ID NO: 24), HLCGSHLVEALYL-VCGERGFF (SEQ ID NO: 25), FVNQHLCG-SHLVEALYLVCGERGFFYTPKT (SEQ ID NO: 26), FVNQHLCGSHLVEALYLVCGERGFFYTKPT (SEQ ID NO: 27), FVNQHLCGSHLVEALYLVC (SEQ ID NO: 28), FVNQHLCGSHLVEALYLVCGERG (SEQ ID NO: 29), FVNQHLCGSHLVEALYLVCGERGFFP (SEQ ID NO: 30), FVNQHLCGSHLVEALYLVCGERGFFYTPK (SEQ ID NO: 31), FVNQHLCGSHLVEALYLVCGERGFFYT-PKT (SEQ ID NO: 26), TNMFTYEIAPVFVLLEYVTL (SEQ ID NO: 32) or GERGFFYTPKTRREAEDLQV (SEQ ID NO: 19).

In some embodiments of any one of the compositions, peptides, methods, kits, or antigen presenting cells provided, the at least one T cell epitope is not a CD8+ T cell epitope. In some embodiments of any one of the compositions, peptides, methods, kits, or antigen presenting cells provided, the at least one T cell epitope does not comprise LPLLAL-LAL (SEQ ID NO: 76).

Exemplary peptides and methods for synthesizing or obtaining such peptides are known in the art and described herein. A peptide can be recombinantly and/or synthetically produced. In some embodiments, a peptide is chemically synthesized, e.g., using a method known in the art. Non-limiting examples of peptide synthesis include liquid-phase synthesis and solid-phase synthesis. In some embodiments, a peptide is produced by enzymatic digestion, e.g., by enzymatic digestion of a larger polypeptide into short peptides.

In some embodiments of any one of the compositions, peptides, methods, kits, or antigen presenting cells provided herein, one or more glutamate residues of a peptide may be generated by tissue transglutaminase (tTG) deamidation activity upon one or more glutamine residues of the peptide. This deamidation of glutamine to glutamate may cause the generation of peptides that can bind to HLA-DQ2 or -DQ8 molecules with high affinity. This reaction may occur in vitro by contacting the peptide with tTG outside of the subject or in vivo following administration through deamidation via tTG in the body. Deamidation of a peptide may also be accomplished by synthesizing a peptide de novo with glutamate residues in place of one or more glutamine residues, and thus deamidation does not necessarily require use of tTG. For example, in some embodiments, a peptide comprising the amino acid sequence RREAEDLQGSL (SEQ ID NO: 3) can be deamidated to RREAEDLEGSL (SEQ ID NO: 4) and/or a peptide comprising the amino acid sequence DLQVGQVELGGGP (SEQ ID NO: 5) can be deamidated to DLQVGEVELGGGP (SEQ ID NO: 6). Any one of the compositions provided herein can comprise a deamidated form in addition to or instead of the non-deamidated form. Any one of the peptides as described herein in any one of the compositions, methods, kits, or antigen presenting cells may be the deamidated form instead of the non-deamidated form.

In some embodiments of any one of the compositions, peptides, methods, kits, or antigen presenting cells provided herein, it may be desirable to utilize the non-deamidated forms of such peptides, e.g., if the peptides are contained within a composition for administration to a subject where tissue transglutaminase will act in situ (see, e.g., Øyvind Molberg, Stephen McAdam, Knut E. A. Lundin, Christel Kristiansen, Helene Arentz-Hansen, Kjell Kett and Ludvig M. Sollid. T cells from celiac disease lesions recognize gliadin epitopes deamidated in situ by endogenous tissue transglutaminase. Eur. J. Immunol. 2001. 31: 1317-1323). Accordingly, peptides that have not undergone deamidation are also contemplated herein (e.g., peptides comprising the amino acid sequence RREAEDLQGSL; SEQ ID NO: 3 and/or DLQVGQVELGGGP; SEQ ID NO: 5).

A peptide may also be an analog of any one of the peptides described herein. Preferably, in some embodiments the analog is recognized by a $CD4^+$ T cell that recognizes one or more of the peptides described herein. Exemplary analogs comprise a peptide that has a sequence that is, e.g., 75%, 80%, 85%, 90%, 95%, 96%, 97%, 98%, or 99% homologous to the peptides recited herein. Analogs may also be a variant of any one of the peptides provided, such variants can include conservative amino acid substitutions.

The length of the peptide may vary. In some embodiments of any one of the compositions, peptides, methods, kits, or antigen presenting cells provided herein, peptides are, e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length. In some embodiments of any one of the compositions, peptides, methods, kits, or antigen presenting cells provided herein, peptides are, e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 or fewer amino acids in length. In some embodiments of any one of the compositions, peptides, methods, kits, or antigen presenting cells provided herein, peptides are, e.g., 8-100, 8-50, 8-40, 8-30, or 8-20 amino acids in length. In some embodiments of any one of the compositions, peptides, methods, kits, or antigen presenting cells provided herein, peptides are 4-20, 5-20, 6-20, 7-20, 8-20, 9-20, 10-20, 11-20, 12-20, 13-20, 14-20, or 15-20 amino acids in length. In some embodiments of any one of the compositions, peptides, methods, kits, or antigen presenting cells provided herein, peptides are e.g., 10-19, 11-19, 12-19 or 13-19 amino acids in length. In some embodiments of any one of the compositions, peptides, methods, kits, or antigen presenting cells provided herein, peptides are 4-50, 5-50, 6-50, 7-50, 8-50, 9-50, 10-50, 11-50, 12-50, 13-50, 14-50, or 15-50 amino acids in length. In some embodiments of any one of the compositions, peptides, methods, kits, or antigen presenting cells provided herein, each of the at least one peptides are independently between 8 to 50 amino acids in length.

In some embodiments of any one of the compositions provided, a composition comprising one or one or more peptide(s) is contemplated. In some embodiments, the composition comprises at least one (e.g., 1, 2, 3, or more) peptide, the at least one peptide comprising at least one (e.g., 1, 2, 3, or more) amino acid sequence(s) selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or a T cell epitope contained within the at least one amino acid sequence. In some embodiments, the composition comprises at least one (e.g., 1, 2, 3, or more) peptide, the at least one peptide comprising at least one (e.g., 1, 2, 3, or more) amino acid sequence(s) selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), or PKAARPPVTPVLLEKKS (SEQ ID NO: 13). In some embodiments of any one of the compositions provided, the at least one T cell epitope contained within the at least one amino acid sequence of the at least one (e.g., 1, 2, 3, 3 or more) peptide comprises an amino acid sequence LLALLALWGPD (SEQ ID NO: 14).

"First", "second", "third", etc. are not meant to imply an order of use or importance, unless specifically stated otherwise. In some embodiments, the composition comprises at least one, at least two, at least three, or more of any of the peptides provided herein. In some embodiments of any one of the compositions, peptides, methods, kits, or antigen presenting cells provided herein, at least one of the peptides comprises an N-terminal modification (e.g., a pyroglutamate or acetyl group) and/or a C-terminal modification (e.g., an amide group). In some embodiments of any one of the compositions, peptides, methods, kits, or antigen presenting cells provided herein, each of the peptides comprises an N-terminal modification (e.g., a pyroglutamate or acetyl group) and/or a C-terminal modification (e.g., an amide group).

Modifications to a peptide are also contemplated herein. This modification may occur during or after translation or synthesis (for example, by farnesylation, prenylation, myristoylation, glycosylation, palmitoylation, acetylation, phosphorylation (such as phosphotyrosine, phosphoserine or phosphothreonine), amidation, pyrolation, derivatisation by known protecting/blocking groups, proteolytic cleavage, linkage to an antibody molecule or other cellular ligand, and the like). Any of the numerous chemical modification methods known within the art may be utilized including, but not limited to, specific chemical cleavage by cyanogen bromide, trypsin, chymotrypsin, papain, V8 protease, NaBH4, acetylation, formylation, oxidation, reduction, metabolic synthesis in the presence of tunicamycin, etc.

The phrases "protecting group" and "blocking group" as used herein, refers to modifications to the peptide which protect it from undesirable chemical reactions, particularly chemical reactions in vivo. Examples of such protecting groups include esters of carboxylic acids and boronic acids, ethers of alcohols and acetals, and ketals of aldehydes and ketones. Examples of suitable groups include acyl protecting groups such as, for example, furoyl, formyl, adipyl, azelayl, suberyl, dansyl, acetyl, theyl, benzoyl, trifluoroacetyl, succinyl and methoxysuccinyl; aromatic urethane protecting groups such as, for example, benzyloxycarbonyl (Cbz); aliphatic urethane protecting groups such as, for example, t-butoxycarbonyl (Boc) or 9-fluorenylmethoxy-carbonyl (FMOC); pyroglutamate, or acetylation and amidation. Many other modifications providing increased potency, prolonged activity, ease of purification, and/or increased half-life are known to the person skilled in the art.

Any one or more of the peptides may comprise one or more modifications, which may be natural post-translation modifications or artificial modifications. The modification may provide a chemical moiety (typically by substitution of a hydrogen, for example, of a C—H bond), such as an amino, acetyl, acyl, carboxy, hydroxy or halogen (for example, fluorine) group, or a carbohydrate group. Typically, the modification is present on the N- and/or C-terminal. Furthermore, any one or more of the peptides may be PEGylated, where the PEG (polyethyleneoxy group) provides for enhanced lifetime in the blood stream. Any one or more of the peptides may also be combined as a fusion or chimeric protein with other proteins, or with specific binding agents that allow targeting to specific moieties on a target cell.

A peptide may also be chemically modified at the level of amino acid side chains, of amino acid chirality, and/or of the peptide backbone.

Particular changes can be made to a peptide to improve resistance to degradation or optimize solubility properties or otherwise improve bioavailability compared to the parent peptide, thereby providing peptides having similar or improved therapeutic, diagnostic and/or pharmacokinetic properties. A preferred such modification includes the use of an N-terminal acetyl group or pyroglutamate and/or a C-terminal amide. Such modifications have been shown in the art to significantly increase the half-life and bioavailability of the peptides compared to the parent peptides having a free N- and C-terminus (see, e.g., PCT Publication No.: WO/2010/060155). In some embodiments, any one or more of the peptides comprise an N-terminal acetyl group or pyroglutamate group, and/or a C-terminal amide group.

Peptide Production

The peptides described herein can be prepared in any suitable manner. For example, the peptides can be recombinantly and/or synthetically produced.

The peptides may be synthesised by standard chemistry techniques, including synthesis by an automated procedure using a commercially available peptide synthesiser. In general, peptides may be prepared by solid-phase peptide synthesis methodologies which may involve coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminal. After the last residue has been attached, the protected peptide-resin is treated with hydrogen fluoride to cleave the peptide from the resin, as well as deprotect the side chain functional groups. Crude product can be further purified by gel filtration, high pressure liquid chromatography (HPLC), partition chromatography, or ion-exchange chromatography.

If desired, various groups may be introduced into the peptide during synthesis or during expression, which allow for linking to other molecules or to a surface. For example, cysteines can be used to make thioethers, histidines for linking to a metal ion complex, carboxyl groups for forming amides or esters, amino groups for forming amides, and the like.

The peptides may also be produced using cell-free translation systems. Standard translation systems, such as reticulocyte lysates and wheat germ extracts, using RNA as a template; whereas "coupled" and "linked" systems start with DNA templates, which are transcribed into RNA then translated.

Alternatively, the peptides may be produced by transfecting host cells with expression vectors that comprise polynucleotide(s) that encode one or more peptides.

For recombinant production, a recombinant construct comprising a sequence which encodes one or more of the peptides is introduced into host cells by conventional methods such as calcium phosphate transfection, DEAE-dextran mediated transfection, microinjection, cationic lipid-mediated transfection, electroporation, transduction, scrape lading, ballistic introduction or infection.

One or more of the peptides may be expressed in suitable host cells, such as, for example, mammalian cells (for example, COS, CHO, BHK, 293 HEK, VERO, HeLa, HepG2, MDCK, W138, or NIH 3T3 cells), yeast (for example, *Saccharomyces* or *Pichia*), bacteria (for example, *E. coli, P. pastoris,* or *B. subtilis*), insect cells (for example, baculovirus in Sf9 cells) or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the peptide or variant thereof.

Suitable expression vectors include, for example, chromosomal, non-chromosomal and synthetic polynucleotides, for example, derivatives of SV40, bacterial plasmids, phage DNAs, yeast plasmids, vectors derived from combinations of plasmids and phage DNAs, viral DNA such as vaccinia viruses, adenovirus, adeno-associated virus, lentivirus, canary pox virus, fowl pox virus, pseudorabies, baculovirus, herpes virus and retrovirus. The polynucleotide may be introduced into the expression vector by conventional procedures known in the art.

The polynucleotide which encodes one or more peptides may be operatively linked to an expression control sequence, i.e., a promoter, which directs mRNA synthesis. Representative examples of such promoters include the LTR or SV40 promoter, the *E. coli* lac or trp, the phage lambda PL promoter and other promoters known to control expression of genes in prokaryotic or eukaryotic cells or in viruses. The expression vector may also contain a ribosome binding site for translation initiation and a transcription terminator. The expression vectors may also include an origin of replication and a selectable marker, such as the ampicillin resistance gene of *E. coli* to permit selection of transformed cells, i.e., cells that are expressing the heterologous polynucleotide. The nucleic acid molecule encoding one or more of the peptides may be incorporated into the vector in frame with translation initiation and termination sequences.

One or more of the peptides can be recovered and purified from recombinant cell cultures (i.e., from the cells or culture medium) by well-known methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin chromatography, and HPLC. Well known techniques for refolding proteins may be employed to regenerate active conformation when the peptide is denatured during isolation and or purification.

To produce a glycosylated peptide, it is preferred that recombinant techniques be used. To produce a glycosylated peptide, it is preferred that mammalian cells such as, COS-7 and Hep-G2 cells be employed in the recombinant techniques.

The peptides can also be prepared by cleavage of longer peptides, especially from food extracts.

Pharmaceutically acceptable salts of the peptides can be synthesised from the peptides which contain a basic or acid moiety by conventional chemical methods. Generally, the salts are prepared by reacting the free base or acid with stoichiometric amounts or with an excess of the desired salt-forming inorganic or organic acid or base in a suitable solvent.

In some embodiments, any one of the compositions described herein further comprises a pharmaceutically acceptable carrier. The term "pharmaceutically acceptable carrier" refers to molecular entities and compositions that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, excipients, solvents, surfactants, suspending agents, buffering agents, lubricating agents, adjuvants, vehicles, emulsifiers, absorbents, dispersion media, coatings, stabilizers, protective colloids, adhesives, thickeners, thixotropic agents, penetration agents, sequestering agents, isotonic and absorption delaying agents that do not affect the activity of the active agents of the pharmaceutical composition. The carrier can be any of those conventionally used and is limited only by chemico-physical considerations, such as solubility and lack of reactivity with the active agent, and by the route of administration. Suitable carriers for the pharmaceutical composition include those conventionally used, for example, water, saline, aqueous dextrose, lactose, Ringer's solution, a buffered solution, hyaluronan, glycols, starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Liposomes may also be used as carriers. Other carriers are well known in the art (see, e.g., Remington: The Science and Practice of Pharmacy, 21st Ed. Lippincott Williams & Wilkins, 2005).

Assessing Efficacy of Treatment and Selecting Subjects for Treatment

Aspects of the disclosure relate to methods of assessing efficacy of treatment of autoimmune diabetes (e.g., T1D) in a subject. In some embodiments of any one of the methods provided, the subject has T1D or T1D and Celiac disease.

In some embodiments of any one of the methods provided, the method comprises:

(a) measuring a T cell response to a composition comprising at least one peptide as described herein or an antigen presenting cell as described herein in a sample from a subject that has been administered a tolerogenic treatment (such as a peptide composition or antigen presenting cell comprising a peptide);

(b) assessing the efficacy based on the measuring.

In some embodiments of any one of the methods provided, the method comprises:

(a) measuring a T cell response to a composition comprising at least one peptide as described herein or an antigen presenting cell as described herein in a sample from a subject that has been administered the composition or antigen presenting cell; and (b) assessing the efficacy based on the measuring. The composition may be any one of the compositions provided herein.

In some embodiments of any one of the methods provided, the method further comprises (c) treating the subject, or suggesting a treatment to the subject, based on the assessing. In some embodiments of any one of the methods provided, the method further comprises administering the tolerogenic treatment. In some embodiments of any one of the methods provided, the method further comprises administering the composition or antigen presenting cell to the subject. In some embodiments, the composition comprises at least one peptide comprising at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence. In some embodiments of any one of the compositions provided, the at least one T cell epitope contained within the at least one amino acid sequence comprises an amino acid sequence LLALLALWGPD (SEQ ID NO: 14).

In some embodiments of any one of the methods provided, the treating comprises continuing with the treatment, or the suggesting comprises suggesting the subject continue with the treatment, based on the assessing if the assessing indicates the T cell response is at or above a control T cell response. In some embodiments of any one of the methods provided, the treating comprises ceasing the treatment, or the suggesting comprises suggesting the subject cease the treatment, based on the assessing; if the assessing indicates the T cell response is below a control T cell response. In some embodiments of any one of the methods provided, the treating comprises administering a different or additional treatment, or the suggesting comprises suggesting the subject be treated with an additional or different treatment, based on the assessing, if the assessing indicates the T cell response is below a control T cell response.

In some embodiments of any one of the methods provided, the T cell response to the composition or antigen presenting cell is measured by measuring a level of a cytokine secreted by a T cell in a sample from the subject after the sample has been contacted with the composition or antigen presenting cell. In some embodiments, sample has been contacted with a composition comprising 0.4 micrograms/mL, 1 microgram/mL, 4 micrograms/ml, 5 micrograms/ml, 10 micrograms/ml, 20 micrograms/ml, 25 micrograms/ml, or 50 micrograms/mL of at least one peptide as described herein. In some embodiments, the cytokine is one or more of IFN-γ, IL-2 or IP-10. In some embodiments, the cytokine is IP-10.

In some embodiments, the sample comprises fresh blood from the subject. In some embodiments, the sample is contacted with the composition for about 18 to about 30 hours, e.g., about 24 hours. In some embodiments, the sample is contacted with the composition in a 96-well plate.

Other aspects of the disclosure relate to methods of selecting a subject having autoimmune diabetes (e.g., T1D) for treatment. In some embodiments of any one of the methods, the subject has T1D or T1D and Celiac disease. In some embodiments of any one of the methods provided, the method comprises (a) measuring a T cell response to a composition comprising at least one peptide as described herein or antigen presenting cell as described herein in a sample from a subject having autoimmune diabetes (e.g., T1D); and (b) treating the subject, or suggesting a treatment to the subject if the T cell response is at or above a control T cell response. The composition may be any one of the compositions provided herein. In some embodiments, the composition comprises at least one peptide comprising at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence. In some embodiments of any one of the methods provided, the at least one T cell epitope contained within the at least one amino acid sequence comprises an amino acid sequence LLALLALWGPD (SEQ ID NO: 14).

In some embodiments of any one of the methods provided, the treatment comprises administration of the composition or antigen present cell to the subject.

In some embodiments of any one of the methods provided, the T cell response to the composition or antigen presenting cell is measured by measuring a level of a cytokine secreted by a T cell in a sample from the subject after the sample has been contacted with the composition or antigen presenting cell. In some embodiments, the cytokine is one or more of IFN-γ, IL-2 or IP-10. In some embodiments, the cytokine is IP-10.

In some embodiments, the sample comprises fresh blood from the subject. In some embodiments, the sample is contacted with the antigen presenting cell for about 18 to about 30 hours, e.g., about 24 hours. In some embodiments, the sample is contacted with the antigen presenting cell in a 96-well plate.

T Cell Responses and Measurement Thereof

Aspects of the disclosure relate to a determination or measurement of a T cell response in a sample comprising T cells from a subject. Such a T cell response can be measured ex vivo, e.g., by measuring a T cell response in a sample comprising T cells from the subject.

As described herein, an elevated T cell response, such as an elevated CD4+ T cell response, from a sample comprising T cells from a subject compared to a control T cell response can correlate with the presence of autoimmune diabetes (e.g., T1D) in the subject. Accordingly, aspects of the disclosure relate to methods that comprise determining or measuring a T cell response in a sample comprising T cells from a subject, e.g., having or suspected of having autoimmune diabetes (e.g., T1D). In some embodiments of any one of the compositions, peptides, methods, kits, or antigen presenting cells provided, the elevated T cell response is a CD4+ T cell response. In some embodiments of any one of the compositions, peptides, methods, kits, or antigen presenting cells provided, the elevated T cell response is a CD8+ T cell response. In some embodiments of any one of the compositions, peptides, methods, kits, or antigen presenting cells provided, the elevated T cell response is a CD4+ but not a CD8+ T cell response.

In some embodiments of any one of the methods provided, measuring a T cell response in a sample comprising T cells from a subject comprises contacting the sample with a composition comprising at least one peptide as described herein. The composition may be any one of the compositions provided herein. For example, whole blood or PBMCs obtained from a subject may be contacted with the composition comprising the peptides in order to stimulate T cells in the whole blood sample or PBMCs.

Measuring a T cell response can be accomplished using any assay known in the art (see, e.g., Molecular Cloning: A Laboratory Manual, M. Green and J. Sambrook, Fourth Edition, Cold Spring Harbor Laboratory Press, Cold Spring Harbor, N.Y., 2012; Current Protocols in Molecular Biology, F. M. Ausubel, et al., Current Edition, John Wiley & Sons, Inc., New York). In some embodiments, measuring a T cell response comprises an MHC Class II tetramer assay, such as flow cytometry with MHC Class II tetramer staining (see, e.g., Raki M, Fallang L E, Brottveit M, Bergseng E, Quarsten H, Lundin K E, Sollid L M: Tetramer visualization of gut-homing gluten-specific T cells in the peripheral blood of Celiac disease patients. Proceedings of the National Academy of Sciences of the United States of America 2007; Anderson R P, van Heel D A, Tye-Din J A, Barnardo M, Salio M, Jewell D P, Hill A V: T cells in peripheral blood after gluten challenge in coeliac disease. Gut 2005, 54(9): 1217-1223; Brottveit M, Raki M, Bergseng E, Fallang L E, Simonsen B, Lovik A, Larsen S, Loberg E M, Jahnsen F L, Sollid L M et al: Assessing possible Celiac disease by an HLA-DQ2-gliadin Tetramer Test. The American journal of gastroenterology 2011, 106(7):1318-1324; and Anderson R P, Degano P, Godkin A J, Jewell D P, Hill A V: In vivo antigen challenge in Celiac disease identifies a single transglutaminase-modified peptide as the dominant A-gliadin T cell epitope. Nature Medicine 2000, 6(3):337-342).

In some embodiments of any one of the methods, measuring a T cell response in a sample comprising T cells from a subject comprises measuring a level of at least one cytokine in the sample. In some embodiments of any one of the methods, measuring a T cell response in a sample comprising T cells from a subject comprises contacting the sample with a composition comprising at least one peptide as described herein, and measuring a level of at least one cytokine in the sample. In some embodiments of any one of the methods, the at least one cytokine is IL-2, IFN-γ, or IP-10. In some embodiments of any one of the methods, the at least one cytokine comprises all three of IL-2, IFN-γ, and IP-10. In some embodiments of any one of the methods, the at least one cytokine is IP-10. In some embodiments of any one of the methods, the at least one cytokine is IP-10. IL-2, and IFN-γ.

Interferon-γ (IFN-γ, also called IFNG, IFG, and IFI) is a dimerized soluble cytokine of the type II class of interferons. IFN-γ typically binds to a heterodimeric receptor consisting of Interferon γ receptor 1 (IFNGR1) and Interferon γ receptor 2 (IFNGR2). IFN-γ can also bind to the glycosaminoglycan heparan sulfate (HS). IFN-γ is produced predominantly by natural killer (NK) and natural killer T (NKT) cells as part of the innate immune response, and by CD4 Th1 and CD8 cytotoxic T lymphocyte (CTL) effector T cells once antigen-specific immunity develops in a subject. In humans, the IFN-γ protein is encoded by the IFNG gene. The Genbank number for the human IFNG gene is 3458. Exemplary Genbank mRNA transcript IDs and protein IDs for IFN-γ are NM_000619.2 and NP_000610.2, respectively. Exemplary RNA and protein sequences of IFN-γ are provided below.

```
>gi|56786137|ref|NM_000619.2| Homo sapiens
interferon, gamma (IFNG), mRNA
                                      (SEQ ID NO: 33)
CACATTGTTCTGATCATCTGAAGATCAGCTATTAGAAGAGAAAGATCAGT

TAAGTCCTTTGGACCTGATCAGCTTGATACAAGAACTACTGATTTCAACT

TCTTTGGCTTAATTCTCTCGGAAACGATGAAATATACAAGTTATATCTTG

GCTTTTCAGCTCTGCATCGTTTTGGGTTCTCTTGGCTGTTACTGCCAGGA

CCCATATGTAAAAGAAGCAGAAAACCTTAAGAAATATTTTAATGCAGGTC

ATTCAGATGTAGCGGATAATGGAACTCTTTTCTTAGGCATTTTGAAGAAT

TGGAAAGAGGAGAGTGACAGAAAAATAATGCAGAGCCAAATTGTCTCCTT

TTACTTCAAACTTTTTAAAAACTTTAAAGATGACCAGAGCATCCAAAAGA

GTGTGGAGACCATCAAGGAAGACATGAATGTCAAGTTTTTCAATAGCAAC

AAAAAGAAACGAGATGACTTCGAAAAGCTGACTAATTATTCGGTAACTGA

CTTGAATGTCCAACGCAAAGCAATACATGAACTCATCCAAGTGATGGCTG

AACTGTCGCCAGCAGCTAAAACAGGGAAGCGAAAAAGGAGTCAGATGCTG

TTTCGAGGTCGAAGAGCATCCCAGTAATGGTTGTCCTGCCTGCAATATTT

GAATTTTAAATCTAAATCTATTTATTAATATTTAACATTATTTATATGGG

GAATATATTTTTAGACTCATCAATCAAATAAGTATTTATAATAGCAACTT

TTGTGTAATGAAAATGAATATCTATTAATATATGTATTATTTATAATTCC

TATATCCTGTGACTGTCTCACTTAATCCTTTGTTTTCTGACTAATTAGGC

AAGGCTATGTGATTACAAGGCTTTATCTCAGGGGCCAACTAGGCAGCCAA

CCTAAGCAAGATCCCATGGGTTGTGTGTTTATTTCACTTGATGATACAAT

GAACACTTATAAGTGAAGTGATACTATCCAGTTACTGCCGGTTTGAAAAT

ATGCCTGCAATCTGAGCCAGTGCTTTAATGGCATGTCAGACAGAACTTGA

ATGTGTCAGGTGACCCTGATGAAAACATAGCATCTCAGGAGATTTCATGC

CTGGTGCTTCCAAATATTGTTGACAACTGTGACTGTACCCAAATGGAAAG

TAACTCATTTGTTAAAATTATCAATATCTAATATATATGAATAAAGTGTA

AGTTCACAACAAAAAAAAAAAAAAAAAAAAAAAAAAAAAAAA

>gi|56786138|ref|NP_000610.2| interferon gamma
precursor [Homo sapiens]
                                      (SEQ ID NO: 34)
MKYTSYILAFQLCIVLGSLGCYCQDPYVKEAENLKKYFNAGHSDVADNGT

LFLGILKNWKEESDRKIMQSQIVSFYFKLFKNFKDDQSIQKSVETIKEDM

NVKFFNSNKKKRDDFEKLTNYSVTDLNVQRKAIHELIQVMAELSPAAKTG

KRKRSQMLFRGRRASQ

>gi|56786138:24-166 interferon gamma mature
protein [Homo sapiens]
                                      (SEQ ID NO: 35)
QDPYVKEAENLKKYFNAGHSDVADNGTLFLGILKNWKEESDRKIMQSQIV

SFYFKLFKNFKDDQSIQKSVETIKEDMNVKFFNSNKKKRDDFEKLTNYSV

TDLNVQRKAIHELIQVMAELSPAAKTGKRKRSQMLFRGRRASQ
```

IFN-γ inducible protein-10 (IP-10, also referred to as C-X-C motif chemokine 10, CXCL10, small-inducible cytokine B10, SCYB10, C7, IFI10, crg-2, gIP-10, or mob-1) is a protein that in humans is encoded by the CXCL10 gene. IP-10 is a small cytokine belonging to the CXC chemokine family and binds to the chemokine receptor CXCR3. The Genbank ID number for the human CXCL10 gene is 3627. Exemplary Genbank mRNA transcript IDs and protein IDs for IP-10 are NM_001565.3 and NP_001556.2, respectively. Exemplary sequences for IP-10 are provided below.

>gi|323422857|ref|NM_001565.3| Homo sapiens chemokine (C-X-C motif) ligand 10 (CXCL10), mRNA
(SEQ ID NO: 36)
CTTTGCAGATAAATATGGCACACTAGCCCCACGTTTTCTGAGACATTCCT

CAATTGCTTAGACATATTCTGAGCCTACAGCAGAGGAACCTCCAGTCTCA

GCACCATGAATCAAACTGCCATTCTGATTTGCTGCCTTATCTTTCTGACT

CTAAGTGGCATTCAAGGAGTACCTCTCTCTAGAACTGTACGCTGTACCTG

CATCAGCATTAGTAATCAACCTGTTAATCCAAGGTCTTTAGAAAAACTTG

AAATTATTCCTGCAAGCCAATTTTGTCCACGTGTTGAGATCATTGCTACA

ATGAAAAAGAAGGGTGAGAAGAGATGTCTGAATCCAGAATCGAAGGCCAT

CAAGAATTTACTGAAAGCAGTTAGCAAGGAAAGGTCTAAAAGATCTCCTT

AAAACCAGAGGGGAGCAAAATCGATGCAGTGCTTCCAAGGATGGACCACA

CAGAGGCTGCCTCTCCCATCACTTCCCTACATGGAGTATATGTCAAGCCA

TAATTGTTCTTAGTTTGCAGTTACACTAAAAGGTGACCAATGATGGTCAC

CAAATCAGCTGCTACTACTCCTGTAGGAAGGTTAATGTTCATCATCCTAA

GCTATTCAGTAATAACTCTACCCTGGCACTATAATGTAAGCTCTACTGAG

GTGCTATGTTCTTAGTGGATGTTCTGACCCTGCTTCAAATATTTCCCTCA

CCTTTCCCATCTTCCAAGGGTACTAAGGAATCTTTCTGCTTTGGGGTTTA

TCAGAATTCTCAGAATCTCAAATAACTAAAAGGTATGCAATCAAATCTGC

TTTTTAAAGAATGCTCTTTACTTCATGGACTTCCACTGCCATCCTCCCAA

GGGGCCCAAATTCTTTCAGTGGCTACCTACATACAATTCCAAACACATAC

AGGAAGGTAGAAATATCTGAAAATGTATGTGTAAGTATTCTTATTTAATG

AAAGACTGTACAAAGTAGAAGTCTTAGATGTATATATTTCCTATATTGTT

TTCAGTGTACATGGAATAACATGTAATTAAGTACTATGTATCAATGAGTA

ACAGGAAAATTTTAAAAATACAGATAGATATATGCTCTGCATGTTACATA

AGATAAATGTGCTGAATGGTTTTCAAAATAAAAATGAGGTACTCTCCTGG

AAATATTAAGAAAGACTATCTAAATGTTGAAAGATCAAAAGGTTAATAAA

GTAATTATAACTAAGAAAAAAAAAAAA

>gi|149999382|ref|NP_001556.2| C-X-C motif chemokine 10 precursor [Homo sapiens]
(SEQ ID NO: 37)
MNQTAILICCLIFLTLSGIQGVPLSRTVRCTCISISNQPVNPRSLEKLEI

IPASQFCPRVEIIATMKKKGEKRCLNPESKAIKNLLKAVSKERSKRSP

>gi|149999382:22-98 C-X-C motif chemokine 10 mature protein [Homo sapiens]
(SEQ ID NO: 38)
VPLSRTVRCTCISISNQPVNPRSLEKLEIIPASQFCPRVEIIATMKKKGE

KRCLNPESKAIKNLLKAVSKERSKRSP

Interleukin-2 (IL-2) is a protein that in humans is encoded by the IL2 gene. IL-2 is a secreted cytokine and binds, e.g., to the heterotrimeric protein receptor interleukin-2 receptor (IL-2R). The Genbank ID number for the human IL2 gene is 3558. Exemplary mRNA sequences and protein sequences for IL-2 are shown below.

>|gi|125661059|ref|NM_000586.3| Homo sapiens interleukin 2 (IL2), mRNA
(SEQ ID NO: 39)
AGTTCCCTATCACTCTCTTTAATCACTACTCACAGTAACCTCAACTCCTG

CCACAATGTACAGGATGCAACTCCTGTCTTGCATTGCACTAAGTCTTGCA

CTTGTCACAAACAGTGCACCTACTTCAAGTTCTACAAAGAAAACACAGCT

ACAACTGGAGCATTTACTGCTGGATTTACAGATGATTTTGAATGGAATTA

ATAATTACAAGAATCCCAAACTCACCAGGATGCTCACATTTAAGTTTTAC

ATGCCCAAGAAGGCCACAGAACTGAAACATCTTCAGTGTCTAGAAGAAGA

ACTCAAACCTCTGGAGGAAGTGCTAAATTTAGCTCAAAGCAAAAACTTTC

ACTTAAGACCCAGGGACTTAATCAGCAATATCAACGTAATAGTTCTGGAA

CTAAAGGGATCTGAAACAACATTCATGTGTGAATATGCTGATGAGACAGC

AACCATTGTAGAATTTCTGAACAGATGGATTACCTTTTGTCAAAGCATCA

TCTCAACACTGACTTGATAATTAAGTGCTTCCCACTTAAAACATATCAGG

CCTTCTATTTATTTAAATATTTAAATTTTATATTTATTGTTGAATGTATG

GTTTGCTACCTATTGTAACTATTATTCTTAATCTTAAAACTATAAATATG

GATCTTTTATGATTCTTTTTGTAAGCCCTAGGGGCTCTAAAATGGTTTCA

CTTATTTATCCCAAAATATTTATTATTATGTTGAATGTTAAATATAGTAT

CTATGTAGATTGGTTAGTAAAACTATTTAATAAATTTGATAAATATAAAA

AAAAAAAAAAAAAAAAAAAAA

>gi|28178861|ref|NP_000577.2| interleukin-2 precursor [Homo sapiens]
(SEQ ID NO: 40)
MYRMQLLSCIALSLALVTNSAPTSSSTKKTQLQLEHLLLDLQMILNGINN

YKNPKLTRMLTFKFYMPKKATELKHLQCLEEELKPLEEVLNLAQSKNFHL

RPRDLISNINVIVLELKGSETTFMCEYADETATIVEFLNRWITFCQSIIS

TLT

>|gi|28178861|ref|NP_000577.2| interleukin-2 mature protein [Homo sapiens]
(SEQ ID NO: 41)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT

In some embodiments of any one of the methods, measuring a T cell response comprises measuring a level of at least one cytokine. Levels of at least one cytokine include levels of cytokine RNA, e.g., mRNA, and/or levels of cytokine protein. In a preferred embodiment, levels of the at least one cytokine are protein levels.

Assays for detecting cytokine RNA include, but are not limited to, Northern blot analysis, RT-PCR, sequencing technology, RNA in situ hybridization (using e.g., DNA or RNA probes to hybridize RNA molecules present in the sample), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface (e.g., a glass wafer with addressable location, such as Affymetrix microarray (Affymetrix®, Santa Clara, Calif.)). Designing nucleic acid binding partners, such as probes, is well known in the art. In some embodiments, the nucleic acid binding partners bind to a part of or an entire nucleic acid sequence of at least one cytokine, e.g., IFN-γ, IL-2 or IP-10.

Assays for detecting protein levels include, but are not limited to, immunoassays (also referred to herein as immune-based or immuno-based assays, e.g., Western blot, ELISA, and ELISpot assays), Mass spectrometry, and multiplex bead-based assays. Binding partners for protein detection can be designed using methods known in the art and as described herein. In some embodiments, the protein binding partners, e.g., antibodies, bind to a part of or an entire amino acid sequence of at least one cytokine, e.g., IFN-γ, IL-2 or IP-10. Other examples of protein detection and quantitation methods include multiplexed immunoassays as described for example in U.S. Pat. Nos. 6,939,720 and 8,148,171, and published U.S. Patent Application No. 2008/0255766, and protein microarrays as described for example in published U.S. Patent Application No. 2009/0088329.

Any suitable binding partner is contemplated herein. In some embodiments, the binding partner is any molecule that binds specifically to a cytokine as provided herein. A molecule is said to exhibit "specific binding" if it reacts or associates more frequently, more rapidly, with greater duration and/or with greater affinity with a particular target than it does with alternative targets. As described herein, "binds specifically", when referring to a protein, means that the molecule is more likely to bind to a portion of or the entirety of a protein to be measured than to a portion of or the entirety of another protein. In some embodiments, the binding partner is an antibody or antigen-binding fragment thereof, such as Fab, F(ab)2, Fv, single chain antibodies, Fab and sFab fragments, F(ab')2, Fd fragments, scFv, or dAb fragments. Methods for producing antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, N.Y. (1989), WO2006/040153, WO2006/122786, and WO2003/002609). Binding partners also include other peptide molecules and aptamers that bind specifically. Methods for producing peptide molecules and aptamers are well known in the art (see, e.g., published US Patent Application No. 2009/0075834, U.S. Pat. Nos. 7,435,542, 7,807,351, and 7,239,742). In some embodiments, the binding partner is any molecule that binds specifically to an mRNA (e.g., IFN-γ or IP-10 mRNA). As described herein, "binds specifically to an mRNA" means that the molecule is more likely to bind to a portion of or the entirety of the mRNA to be measured (e.g., by complementary base-pairing) than to a portion of or the entirety of another mRNA or other nucleic acid. In some embodiments, the binding partner that binds specifically to an mRNA is a nucleic acid, e.g., a probe.

In some embodiments of any one of the methods, measuring a level of at least one cytokine comprises a multiplex bead-based assay. An exemplary multiplex bead-based assay involves use of magnetic beads that are internally dyed with fluorescent dyes to produce a specific spectral address. Binding partners (e.g., antibodies) are conjugated to the surface of beads to capture the at least one cytokine. The sample is loaded into a 96-well plate containing the beads and the sample is incubated to allow binding of the at least one cytokine to the beads. A second biotinylated binding partner for the at least one cytokine is added after the at least one cytokine binds to the beads. A streptavidin-conjugated detectable label is then bound to the biotin. Light emitting diodes are used to illuminate the samples, causing the fluorescent dyes in the beads to fluoresce, as well as the detectable label to fluoresce. The concentration of the at least one cytokine is then determined based on the level of fluorescence. An exemplary system for running a multiplex bead-based assay is the MAGPIX® system available from Luminex® Corporation (see, e.g., U.S. Pat. Nos. 8,031,918, 8,296,088, 8,274,656, 8,532,351, 8,542,897, 6,514,295, 6,599,331, 6,632,526, 6,929,859, 7,445,844, 7,718,262, 8,283,037, and 8,568,881, all of which are incorporated by reference herein, and in particular the systems provided herein).

In some embodiments of any one of the methods, measuring a level of at least one cytokine comprises an enzyme-linked immunosorbent assay (ELISA) or enzyme-linked immunosorbent spot (ELISpot) assay. ELISA and ELISpot assays are well known in the art (see, e.g., U.S. Pat. Nos. 5,939,281, 6,410,252, and 7,575,870; Czerkinsky C, Nilsson L, Nygren H, Ouchterlony O, Tarkowski A (1983) "A solid-phase enzyme-linked immunospot (ELISPOT) assay for enumeration of specific antibody-secreting cells". J Immunol Methods 65 (1-2): 109-121 and Lequin R (2005). "Enzyme immunoassay (EIA)/enzyme-linked immunosorbent assay (ELISA)". Clin. Chem. 51 (12): 2415-8).

An exemplary ELISA involves at least one binding partner, e.g., an antibody or antigen-binding fragment thereof, with specificity for the at least one cytokine, e.g., IFN-γ, IL-2 or IP-10. The sample with an unknown amount of the at least one cytokine can be immobilized on a solid support (e.g., a polystyrene microtiter plate) either non-specifically (via adsorption to the surface) or specifically (via capture by another binding partner specific to the same at least one cytokine, as in a "sandwich" ELISA). After the antigen is immobilized, the binding partner for the at least one cytokine is added, forming a complex with the immobilized at least one cytokine. The binding partner can be attached to a detectable label as described herein (e.g., a fluorophor or an enzyme), or can itself be detected by an agent that recognizes the at least one cytokine binding partner that is attached to a detectable label as described herein (e.g., a fluorophor or an enzyme). If the detectable label is an enzyme, a substrate for the enzyme is added, and the enzyme elicits a chromogenic or fluorescent signal by acting on the substrate. The detectable label can then be detected using an appropriate machine, e.g., a fluorimeter or spectrophotometer, or by eye.

An exemplary ELISpot assay involves a binding agent for the at least one cytokine (e.g., an anti-IFN-γ antibody) that is coated aseptically onto a PVDF (polyvinylidene fluoride)-backed microplate. Cells of interest (e.g., peripheral blood mononuclear cells) are plated out at varying densities, along with one or more peptides as described herein, and allowed to incubate for a period of time (e.g., about 24 hours). The at least one cytokine secreted by activated cells is captured locally by the binding partner for the at least one cytokine on the high surface area PVDF membrane. After the at least one cytokine is immobilized, a second binding partner for the at least one cytokine is added, forming a complex with the immobilized at least one cytokine. The binding partner can be linked to a detectable label (e.g., a fluorophor or an enzyme), or can itself be detected by an agent that recognizes the binding partner for the at least one cytokine (e.g., a secondary antibody) that is linked to a detectable label (e.g., a fluorophor or an enzyme). If the detectable label is an enzyme, a substrate for the enzyme is added, and the enzyme elicits a chromogenic or fluorescent signal by acting on the substrate. The detectable label can then be detected using an appropriate machine, e.g., a fluorimeter or spectrophotometer, or by eye.

In some embodiments of any one of the methods, a level of at least one cytokine is measured using an ELISA. As an exemplary method, a composition comprising at least one peptide as described herein is dried onto the inner wall of a blood collection tube. A negative control tube containing no antigen is provided. A positive control tube containing a mitogen is also provided. Blood from a subject is drawn into each of the three tubes. Each tube is agitated to ensure mixing. The tubes are then incubated at 37 degrees Celsius, preferably immediately after blood draw or at least within about 16 hours of collection. After incubation, the cells are separated from the plasma by centrifugation. The plasma is then loaded into an ELISA plate for detection of levels of at least one cytokine (e.g., IFN-γ, IL-2 or IP-10) present in the plasma. A standard ELISA assay as described above can then be used to detect the levels of the at least one cytokine present in each plasma sample.

In some embodiments of any one of the methods, a T cell response measurement in a sample obtained from the subject after a challenge as described herein is detected using any one of the methods above or any other appropriate method and is then compared to a control T cell response. Exemplary control T cell responses include, but are not limited to, a T cell response in a sample obtained from a diseased subject(s) (e.g., subject(s) with T1D), a healthy subject(s) (e.g., subject(s) without T1D). In some embodiments of any one of the methods, a control T cell response is measured using any one of the methods above or any other appropriate methods. In some embodiments of any one of the methods, the same method is used to measure a T cell response in the sample of the subject and the control sample.

In some embodiments of any one of the methods, a T cell response is compared to a control T cell response. In some embodiments of any one of the methods, if the control T cell response is a T cell response in a sample from a healthy control subject or subjects, then an elevated T cell response compared to the control T cell response is indicative that the subject has or is at risk of having T1D while a reduced or equal T cell response compared to the control T cell response is indicative that the subject does not have or is not at risk of having T1D.

An elevated T cell response includes a response that is, for example, 1%, 5%, 10%, 20%, 30%, 40%, 50%, 60%, 70%, 80%, 90%, 100%, 150%, 200%, 300%, 400%, 500% or more above a control T cell response. In some embodiments of any one of the methods provided, an elevated T cell response is a response that is at least two-fold above a control T cell response. In some embodiments of any one of the methods provided, the control T cell response is a T cell response in a sample that has been contacted with a composition comprising phosphate buffered saline and/or dimethyl sulfoxide. A reduced T cell response includes a response that is, for example, 1%, 5%, 10%, 20%, 30%, 40%, 50%, 60%, 70%, 80%, 90%, 100%, 150%, 200%, 300%, 400%, 500% or more below a control T cell response.

In some embodiments of any one of the methods, a second control T cell response is contemplated. In some embodiments of any one of the methods, the second control T cell response is a negative control T cell response. Exemplary negative controls include, but are not limited to, a T cell response in a sample that has been contacted with a non-T cell-activating peptide (e.g., a peptide not recognized by T cells present in a sample from a subject), such as a non-CD4+-T cell-activating peptide, or a T cell response in a sample that has not been contacted with a T cell-activating peptide (e.g., contacting the sample with a saline solution containing no peptides), such as a CD4+ T cell-activating peptide. Such a second control T cell response can be measured using any one of the methods above or any other appropriate methods. In some embodiments of any one of the methods, the second control T cell response is a positive control T cell response. Exemplary positive controls include, but are not limited to, a T cell response in a sample that has been contacted with a mitogen (e.g., phytohaemagglutinin, concanavalin A, lipopolysaccharide, or pokeweed mitogen). In some embodiments of any one of the methods provided, a positive control T cell response is a T cell response in a sample that has been contacted with a pathogen-derived recall antigen peptide mixture (e.g., CEF; a pool of 23 peptides consisting of MHC class I-restricted T-cell epitopes from human cytomegalovirus, Epstein Barr virus and influenza virus available from Mabtech (#3615-1; Nacka Strand, Sweden) or CEFT, a pool of 27 peptides consisting of MHC class I- and II-restricted T-cell epitopes from *Clostridium tetani*, Epstein-Barr virus, Human cytomegalovirus, Influenza A, available from Creative Peptides (#PPO-H107)). Positive and/or negative controls may be used to determine that an assay, such as an ELISA or ELISpot assay, is not defective or contaminated.

Treatment

Other aspects of the disclosure relate to treatment of subjects having autoimmune diabetes (e.g., T1D).

In some embodiments of any one of the methods, the subject to be treated is one selected by any one of the methods described herein, e.g., by evaluating a T cell response to select a subject having autoimmune diabetes (e.g., T1D) for treatment. In some embodiments of any one of the methods, a method of treatment comprises administering an effective amount of a composition comprising at least one peptide described herein to a subject having autoimmune diabetes (e.g., T1D). The compositions may be any one of the compositions provided herein. In some embodiments of any one of the methods, the composition comprises at least one peptide comprising at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence. In some embodiments of any one of the methods provided, the at least one T cell epitope contained within the at least one amino acid sequence comprises an amino acid sequence LLALLALWGPD (SEQ ID NO: 14). In some embodiments of any one of the methods provided, the at least one T cell epitope is not a CD8+ T cell epitope.

Modifications to such peptides, e.g., an N-terminal acetylation or N-terminal pyroglutamate and/or C-terminal amide, are contemplated and described herein. Treatments may be administrated using any method known in the art. Pharmaceutical compositions suitable for each administration route are well known in the art (see, e.g., Remington: The Science and Practice of Pharmacy, 22nd Ed. Pharmaceutical Press, 2012). In some embodiments of any one of the methods, a treatment, e.g., a composition described herein, is administered via intradermal injection.

The peptides may be in a salt form, preferably, a pharmaceutically acceptable salt form. "A pharmaceutically acceptable salt form" includes the conventional non-toxic salts or quaternary ammonium salts of a peptide, for example, from non-toxic organic or inorganic acids. Conventional non-toxic salts include, for example, those derived from inorganic acids such as hydrochloride, hydrobromic, sulphuric, sulfonic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

Any one of the compositions provided may include a pharmaceutically acceptable carrier. The term "pharmaceutically acceptable carrier" refers to molecular entities and compositions that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, excipients, solvents, surfactants, suspending agents, buffering agents, lubricating agents, adjuvants, vehicles, emulsifiers, absorbents, dispersion media, coatings, stabilizers, protective colloids, adhesives, thickeners, thixotropic agents, penetration agents, sequestering agents, isotonic and absorption delaying agents that do not affect the activity of the active agents of the pharmaceutical composition. The carrier can be any of those conventionally used and is limited only by chemico-physical considerations, such as solubility and lack of reactivity with the active agent, and by the route of administration. Suitable carriers for any one of the compositions provided include those conventionally used, for example, water, saline, aqueous dextrose, lactose, Ringer's solution, a buffered solution, hyaluronan, glycols, starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Liposomes may also be used as carriers. Other carriers are well known in the art (see, e.g., Remington: The Science and Practice of Pharmacy, 22nd Ed. Pharmaceutical Press, 2012).

Any one of the compositions provided may be in the form of a sterile injectable aqueous or oleagenous suspension. In some embodiments of any one of the compositions, the composition is formulated as a sterile, injectable solution. This suspension or solution may be formulated according to known methods using those suitable dispersing or wetting agents and suspending agents which have been mentioned above. The sterile injectable preparation may be a suspension in a non-toxic parenterally-acceptable diluent or solvent, for example as a solution in 1,3-butanediol. Among the acceptable carriers that may be employed are water, Ringer's solution and isotonic sodium chloride solution. In some embodiments of any one of the compositions, the composition is formulated as a sterile, injectable solution, wherein the solution is a sodium chloride solution (e.g., sodium chloride 0.9% USP). In some embodiments of any one of the compositions, the composition is formulated as a bolus for intradermal injection. Examples of appropriate delivery mechanisms for intradermal administration include, but are not limited to, implants, depots, syringes, needles, capsules, and osmotic pumps.

It can be advantageous to formulate the active agent in a dosage unit form for ease of administration and uniformity of dosage. "Dosage unit form" as used herein refers to physically discrete units suited as unitary dosages for the subject to be treated; each unit containing a predetermined quantity of active agent calculated to produce the desired therapeutic effect in association with the required pharmaceutical carrier. The specification for the dosage unit forms are dictated by and directly dependent on the unique characteristics of the active agent and the particular therapeutic effect to be achieved, and the limitations inherent in the art of compounding such an active agent for the treatment of subjects. Alternatively, the compositions may be presented in multi-dose form. Examples of dosage units include sealed ampoules and vials and may be stored in a freeze-dried condition requiring only the addition of the sterile liquid carrier immediately prior to use.

The actual amount administered (or dose or dosage) and the rate and time-course of administration will depend on the nature and severity of the condition being treated as well as the characteristics of the subject to be treated (weight, age, etc.). Prescription of treatment, for example, decisions on dosage, timing, frequency, etc., is within the responsibility of general practitioners or specialists (including human medical practitioner, veterinarian or medical scientist) and typically takes account of the disorder to be treated, the condition of the subject, the site of delivery, the method of administration and other factors known to practitioners. Examples of techniques and protocols can be found in, e.g., Remington: The Science and Practice of Pharmacy, 22nd Ed. Pharmaceutical Press, 2012. Effective amounts may be measured from ng/kg body weight to g/kg body weight per minute, hour, day, week or month. Dosage amounts may vary from, e.g., 10 ng/kg to up to 100 mg/kg of mammal body weight or more per day, preferably about 1 µg/kg/day to 10 mg/kg/day, depending upon the route of administration.

As used herein, the terms "treat", "treating", and "treatment" include abrogating, inhibiting, slowing, or reversing the progression of a disease or condition, or ameliorating or preventing a clinical symptom of the disease (for example, T1D). Treatment may include induction of immune tolerance (for example, to islet cells), modification of the cytokine secretion profile of the subject and/or induction of suppressor T cell subpopulations to secrete cytokines. In some embodiments of any one of the methods, an effective amount of a treatment is administered. The term "effective amount" means the amount of a treatment sufficient to provide the desired therapeutic or physiological effect when administered under appropriate or sufficient conditions.

Toxicity and therapeutic efficacy of the agent can be determined by standard pharmaceutical procedures in cell cultures or experimental animals by determining the IC50 and the maximal tolerated dose. The data obtained from these cell culture assays and animal studies can be used to formulate a range suitable for humans.

Subjects

A subject may include any subject that is suspected of having or has autoimmune diabetes, including T1D, latent autoimmune diabetes in adults (LADA), or be considered at elevated risk of developing T1D (pre-diabetes). In some embodiments, such subjects possess MHC-Class II genes associated with T1D (HLA-DR3, DR4, DQ2 or and DQ8) and also have detectable levels of serum IgG specific autoantigens associated with T1D (e.g. anti-insulin, anti-GAD, anti-IA-2, and/or anti-zinc-transporter-8). In some embodiments of any one of the methods provided herein, the subject may include any subject that has or is suspected of having T1D and Celiac disease. Preferably, the subject is a human. In some embodiments, the subject has one or more HLA-DRB, HLA-DQA and HLA-DQB susceptibility alleles encoding HLA-DR3, HLA-DR4, HLA-DQ2.5

(DQA1*05 and DQB1*02) or HLA-DQ8 (DQA1*03 and DQB1*0302). In some embodiments, a subject may have a family member that has HLA-DQ8 (DQA1*03 and DQB1*0302). The presence of susceptibility alleles can be detected by any nucleic acid detection method known in the art, e.g., by polymerase chain reaction (PCR) amplification of DNA extracted from the patient followed by hybridization with sequence-specific oligonucleotide probes. A subject may be identified as having or suspected of having T1D or T1D and Celiac disease using diagnostic methods known in the art and/or described herein (e.g., diagnostic assays for T1D and diagnostic assays for Celiac disease).

Exemplary diagnostic assays for T1D include, but are not limited to, a glycated hemoglobin test, a glucose tolerance test, a fasting blood sugar test, and/or an autoantibody assay. In some embodiments, a glycated hemoglobin level at or above 6.5, plasma glucose at or above 11.1 mmol/L (200 mg/dL), a fasting plasma glucose level at or above 7.0 mmol/L, the presence of autoantibodies, or a combination thereof, indicates the subject has T1D.

Glycated hemoglobin may be detected using high-performance liquid chromatography (HPLC), immunoassay, enzymatic assay, capillary electrophoresis, or boronate affinity chromatography.

A glucose tolerance test may comprise administering glucose to a subject and obtaining blood from the subject after the glucose administration to determine how quickly the glucose is cleared from the blood. In some embodiments, an oral glucose tolerance test (OGTT) is used and a standard dose of glucose is ingested by mouth and blood levels are measured from a sample collected two hours later. Glucose may be measured using any method known in the art.

A fasting blood sugar test may comprise measuring blood glucose levels after a subject has not eaten for at least 8 hours. Glucose may be measured using any method known in the art.

Autoantibodies may be detected using any method known in the art, e.g., by ELISA, histology, cytology, immunofluorescence or western blotting. In some embodiments, autoantibodies are detecting using an immunoassay. In some embodiments, autoantibodies comprise one or more of islet cell autoantibodies, insulin autoantibodies, 65-kDa isoform of glutamic acid decarboxylase (GAD65) autoantibodies, islet antigen-2 (IA-2) autoantibodies, and zinc transporter (ZnT8) autoantibodies. Islet cell autoantibodies may be detected by indirect immunofluorescence. GAD65, IA-2, and/or ZnT8 autoantibodies may be detected using radioimmunoassay or ELISA.

Genetic testing (genotyping) is also contemplated. Subjects can be tested for the presence of the HLA-DRB, HLA-DQA and HLA-DQB susceptibility alleles encoding, e.g., HLA-DR3 (DRB1*03) or HLA-DR4 (DRB1*04), HLA-DQ2.5 (DQA1*05 and DQB1*02), DQ2.2 (DQA1*02 and DQB1*02) or DQ8 (DQA1*03 and DQB1*0302). Exemplary sequences that encode the DQA and DQB susceptibility alleles include HLA-DQA1*0501 (Genbank accession number: AF515813.1) HLA-DQA1*0505 (AH013295.2), HLA-DQB1*0201 (AY375842.1) or HLA-DQB1*0202 (AY375844.1). Methods of genetic testing are well known in the art (see, e.g., Nguyen et al. Definition of High-Risk Type 1 Diabetes HLA-DR and HLA-DQ Types Using Only Three Single Nucleotide Polymorphisms. Diabetes 2013. 62: 2135-2140; Morahan et al. The genetics of type 1 diabetes. In The HLA Complex in Biology and Medicine: A Resource Book. Mehra N K, Ed., New Delhi, JayPee Brothers Publishing, 2010, p. 205-218; Leslie et al. A statistical method for predicting classical HLA alleles from SNP data. Am J Hum Genet 2008; 82:48-56; Dilthey et al. HLA*IMP—an integrated framework for imputing classical HLA alleles from SNP genotypes. Bioinformatics 2011; 27:968-972; Ferreira et al. High-density SNP mapping of the HLA region identifies multiple independent susceptibility loci associated with selective IgA deficiency. PLoS Genet 2012; 8:e1002476; Barker et al. Two single nucleotide polymorphisms identify the highest-risk diabetes HLA genotype: potential for rapid screening. Diabetes 2008; 57:3152-3155; 29. Sanjeevi et al. DR4 subtypes and their molecular properties in a population-based study of Swedish childhood diabetes. Tissue Antigens 1996; 47:275-283; Aly et al. Extreme genetic risk for type 1A diabetes. Proc Natl Acad Sci USA 2006; 103:14074-14079).

Subjects that have one or more copies of a susceptibility allele are considered to be positive for that allele. Detection of the presence of susceptibility alleles can be accomplished by any nucleic acid assay known in the art, e.g., by polymerase chain reaction (PCR) amplification of DNA extracted from the patient followed by hybridization with sequence-specific oligonucleotide probes or using leukocyte-derived DNA.

T cell response tests are also contemplated as a diagnostic for autoimmune diabetes (e.g., T1D) and are provided herein. In some embodiments, a T cell response test comprises contacting a sample comprising a T cell with a peptide as described herein and measuring a T cell response in the sample. In some embodiments, a T cell response is measured by measuring a level of a cytokine as described herein (e.g., IP-10, IL-2, and/or IFN-γ), where an increased level of the cytokine compared to a control level (e.g., a level of the cytokine in a sample that has not been contacted with a peptide as described herein) may identify a subject as having autoimmune diabetes, such as T1D. Exemplary T cell response tests are known in the art (see, e.g., PCT Publication Nos.: WO/2001/025793, WO/2003/104273, WO/2005/105129, and WO/2010/060155).

In some embodiments of any one of the methods, the subject has one or more symptoms of T1D. Exemplary symptoms of T1D include, but are not limited to, polyuria (frequent urination), polydipsia (increased thirst), polyphagia (increased hunger), or weight loss. In some embodiments, the subject may have diabetic ketoacidosis. Symptoms of diabetic ketoacidosis include xeroderma (dry skin), rapid deep breathing, drowsiness, abdominal pain, and vomiting. Other symptoms of T1D are known in the art and within the knowledge of the skilled practitioner.

In some embodiments of any one of the methods, the subject is on a gluten-free diet.

Samples

Samples, as used herein, refer to biological samples taken or derived from a subject, e.g., a subject having or suspected of having autoimmune diabetes (e.g., T1D). Examples of samples include tissue samples or fluid samples. Examples of fluid samples are whole blood, plasma, serum, and other bodily fluids that comprise T cells. In some embodiments of any one of the methods or kits provided herein, the sample comprises T cells. In some embodiments of any one of the methods or kits provided herein, the sample comprises T cells and monocytes and/or granulocytes. In some embodiments of any one of the methods or kits provided herein, the sample comprising T cells comprise whole blood or peripheral blood mononuclear cells (PBMCs). The T cell may be a CD4+ T cell, e.g., an islet-cell-reactive CD4+ T cell. In some embodiments of any one of the methods provided herein, the method comprises obtaining or providing the sample. In some embodiments of any one of the methods, a first sample and second sample are contemplated. Additional samples, e.g., third, fourth, fifth, etc., are also contemplated if additional measurements of a T cell response are desired. Such additional samples may be obtained from the subject at any time.

Controls and Control Subjects

In some embodiments of any one of the methods, the methods provided herein comprise measuring or use of a control T cell response. In some embodiments of any one of the methods, the control T cell response is a T cell response in a sample from the subject.

In some embodiments of any one of the methods, the control T cell response is a T cell response in a sample obtained from a control subject (or subjects). In some embodiments, a control subject, e.g., has one or more HLA-DR3, HLA-DR4, HLA-DQA and HLA-DQB susceptibility alleles encoding, e.g., HLA-DR3 (DRB1*03), HLA-DR4 (DRB1*04), HLA-DQ2.5 (DQA1*05 and DQB1*02) or DQ8 (DQA1*03 and DQB1*0302) described herein but does not have T1D or does not have T1D and Celiac disease. In some embodiments, a control subject does not have any of the HLA-DR3, HLA-DR4, HLA-DQA and HLA-DQB susceptibility alleles. In some embodiments, a control subject is a healthy individual not having or suspected of having T1D or T1D and Celiac disease. In some embodiments of any one of the methods or kits, a control level is a pre-determined value from a control subject or subjects, such that the control level need not be measured every time the methods described herein are performed.

In some embodiments, a control level is a level from a sample contacted with a composition comprising phosphate buffered saline or phosphate buffered saline and dimethyl sulfoxide.

Polynucleotides, Antigen Presenting Cells, and HLA Molecules

The at least one peptide described herein may be encoded by one or more polynucleotides. In some embodiments of any one of the compositions, methods, or kits provided herein, a composition may comprise a mixture of peptides and polynucleotides that encode the peptides.

The overall length of each constituent polynucleotide may be, for example, 21 to 150 nucleotides, such as, 21, 22, 23, 24, 25, 26, 27, 28, 29, 30, 31, 32, 33, 34, 35, 36, 37, 38, 39, 40, 41, 42, 43, 44, 45, 50, 60, 70, 80, 90, 100, 110, 120, 130, 140, or 150 nucleotides.

Analogues of the polynucleotides are also contemplated. Analogues include polynucleotides that vary by one or more nucleotides from a reference polynucleotide. For example, an analogue can comprise a substitution of one or more naturally occurring nucleotides with a nucleotide analogue (such as the morpholine ring), methylated nucleotide, internucleotide modifications such as uncharged linkages (for example, methyl phosphonates, phosphotriesters, phosphoamidates, carbamates, etc.), charged linkages (for example, phosphorothioates, phosphorodithioates, etc.), pendent moieties (for example, polypeptides), intercalators (for example, acridine, psoralen, etc.), chelators, alkylators and modified linkages (for example, α-anomeric nucleic acids, etc.). Polynucleotides encoding one or more of the peptides may be provided in a vector.

A polynucleotide encoding one or more of the peptides defined herein can be used for the recombinant production of the peptides using techniques well known in the art. A polynucleotide of the disclosure may include a DNA sequence that can be derived from one or more of the peptides, bearing in mind the degeneracy of codon usage. This is well known in the art, as is knowledge of codon usage in different expression hosts, which is helpful in optimizing the recombinant expression of the peptides.

When the polynucleotide is used for the recombinant production of one or more of the peptides, the polynucleotide may include the coding sequence for the peptides alone or the coding sequence for the peptides in reading frame with other coding sequences, such as those encoding a leader or secretory sequence, a pre-, or pro- or prepro-protein sequence, linker peptide sequence, or other fusion peptide portions. For example, a marker sequence which facilitates purification of the fused peptide can be encoded. In certain embodiments, the marker sequence is a hexa-histidine peptide, as provided in the pQE vector (Qiagen, Inc.), or is an HA tag, or is glutathione-S-transferase. The polynucleotide may also contain non-coding 5' and 3' sequences, such as transcribed, non-translated sequences, splicing and polyadenylation signals, ribosome binding sites and sequences that stabilise mRNA.

Antigen presenting cells (APCs) are also contemplated herein. In some embodiments, an antigen presenting cell comprising a composition, peptide, or polynucleotide as described herein is contemplated. The composition, peptide, or polynucleotide defined herein may be delivered by loading APCs with, for example, at least one peptide described herein and/or a polynucleotide encoding one or more thereof.

In some embodiments, the APCs are selected from the group consisting of dendritic cells, macrophages, B-lymphocytes and liver sinusoidal endothelial cells that express MHC class II molecules shared with the MHC phenotype of the subject. For example, the APCs may express HLA DQ8. The APCs employed for this purpose may be isolated from the subject to whom they are to be delivered after loading, or they may be obtained from an allo-matched subject.

By "loading" an APC it is meant that the APC is incubated or transfected with one or more peptides or a polynucleotide encoding one or more thereof. Loading an APC can be achieved by using conventional nucleic acid transfection methods, such as lipid-mediated transfection, electroporation, or calcium phosphate transfection.

In some embodiments, one or more peptides described herein are bound to a) an HLA molecule, or b) a fragment of an HLA molecule, capable of binding the peptide(s). In some embodiments, the HLA molecule is a heterodimer of an HLA-DR3 molecule, an HLA-DR4 molecule, or an HLA-DQA protein encoded by HLA-DQA1*05, DQA1*02, or DQA1*03, and an HLA-DQB protein encoded by HLA-DQB1*02, or DQB1*0302. In some embodiments, the fragment of an HLA molecule is a fragment of such a heterodimer of an HLA-DR3 molecule, an HLA-DR4 molecule, or an HLA-DQA protein encoded by HLA-DQA1*05, DQA1*02, or DQA1*03, and an HLA-DQB protein encoded by HLA-DQB1*02, or DQB1*0302.

Kits

Other aspects of this disclosure relate to kits. In some embodiments of any one of the kits, the kit comprises any one of the compositions as described herein.

In some embodiments, the composition comprises at least one (e.g., 1, 2, 3 or more) peptide comprising at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQV-GEVELGGGP (SEQ ID NO: 6), CGSHLVEALYLVC (SEQ ID NO: 7), MNILLEYVVKS (SEQ ID NO: 8), NMFTYE-IAPVFVLLEYV (SEQ ID NO: 9), NVCFWYIPPSLR-TLEDN (SEQ ID NO: 10), FNQLSTGLDMVGLAADW (SEQ ID NO: 11), GRTGTYILIDMVLNRMA (SEQ ID NO: 12), PKAARPPVTPVLLEKKS (SEQ ID NO: 13), or at least one T cell epitope contained within the at least one amino acid sequence. In some embodiments of any one of the kits provided, the at least one T cell epitope contained within the at least one amino acid sequence of the at least one peptide (e.g., 1, 2, 3, or more) comprises an amino acid sequence LLALLALWGPD (SEQ ID NO: 14). In some embodiments of any one of the kits provided, the at least one T cell epitope of the at least one peptide (e.g., 1, 2, 3, or more) is not a CD8+ T cell epitope. In some embodiments of any one of the kits provided, the at least one T cell epitope does not comprise LPLLALLAL (SEQ ID NO: 76).

In some embodiments of any one of the kits, the kit further comprises means to detect binding of the one or more of the peptides in the composition to a T cell. In some embodiments of any one of the kits, the kit further comprises means for administering the composition to a subject, e.g., a needle.

In some embodiments of any one of the kits, the means to detect binding of one or more of the peptides in the composition to T cells is a binding partner (e.g., an antibody) specific for a cytokine, e.g., IFN-gamma, IL-2 or IP-10. Binding partners are described herein. In some embodiments of any one of the kits, the kit further comprises an agent that recognizes the binding partner. In some embodiments of any one of the kits, the kit further comprises a container for blood. In some embodiments of any one of the kits, the composition is contained within the container (e.g., dried onto the wall of the container).

In some embodiments of any one of the kits, the kit comprises a first and second binding partner for the cytokine. Binding partners are described herein. In some embodiments of any one of the kits, the first and second binding partners are antibodies or antigen binding fragments thereof. In some embodiments of any one of the kits, the second binding partner is bound to a surface. The second binding partner may be bound to the surface covalently or non-covalently. The second binding partner may be bound directly to the surface, or may be bound indirectly, e.g., through a linker. Examples of linkers, include, but are not limited to, carbon-containing chains, polyethylene glycol (PEG), nucleic acids, monosaccharide units, and peptides. The surface can be made of any material, e.g., metal, plastic, paper, or any other polymer, or any combination thereof. In some embodiments of any one of the kits, the first binding partner for the cytokine is washed over the cytokine bound to the second binding partner (e.g., as in a sandwich ELISA). The first binding partner may comprise a detectable label, or an agent that recognizes the first binding partner for the cytokine (e.g., a secondary antibody) may comprise a detectable label.

Any suitable agent that recognizes a binding partner for the cytokine is contemplated. In some embodiments of any one of the kits, the binding partner is any molecule that binds specifically to the binding partner for the cytokine. In some embodiments of any one of the kits, the agent is an antibody (e.g., a secondary antibody) or antigen-binding fragment thereof, such as Fab, F(ab)2, Fv, single chain antibodies, Fab and sFab fragments, F(ab')2, Fd fragments, scFv, or dAb fragments. Agents also include other peptide molecules and aptamers that bind specifically to a binding partner for the cytokine. In some embodiments of any one of the kits, the binding partner for the cytokine comprises a biotin moiety and the agent is a composition that binds to the biotin moiety (e.g., an avidin or streptavidin).

In some embodiments of any one of the kits, the binding partner for the cytokine comprises a detectable label. Any suitable detectable label is contemplated. Detectable labels include any composition detectable by spectroscopic, photochemical, biochemical, immunochemical, chemical, or other physical means, e.g., an enzyme, a radioactive label, a fluorophore, an electron dense reagent, biotin, digoxigenin, or a hapten. Such detectable labels are well-known in the art are detectable through use of, e.g., an enzyme assay, a chromogenic assay, a luminometric assay, a fluorogenic assay, or a radioimmune assay. The reaction conditions to perform detection of the detectable label depend upon the detection method selected.

In some embodiments of any one of the kits, the kit further comprises a negative control, e.g., a composition that does not comprise a peptide as described herein, e.g., a saline solution or cell culture medium. In some embodiments of any one of the kits, the kit further comprises a positive control, e.g., a composition comprising the cytokine at a pre-determined concentration.

In some embodiments of any one of the kits, the kit comprises any combination of the components mentioned above.

In some embodiments of any one of the kits, the kit further comprises instructions for use of the composition. In some embodiments of any one of the kits, the instructions include a method as described herein. Instructions can be in any suitable form, e.g., as a printed insert or a label.

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, techniques utilized in the present disclosure are standard procedures, well known to those skilled in the art. Such techniques are described and explained throughout the literature in sources such as, J. Sambrook et al., Molecular Cloning: A Laboratory Manual, Cold Spring Harbour Laboratory Press (2012); T. A. Brown (editor), Essential Molecular Biology: A Practical Approach, Volumes 1 and 2, IRL Press (2000 and 2002); D. M. Glover and B. D. Hames (editors), Current Protocols in Molecular Biology, Greene Pub. Associates and Wiley-Interscience (1988, including all updates until present); Edward A. Greenfield (editor) Antibodies: A Laboratory Manual, Cold Spring Harbour Laboratory, (2013); and J. E. Coligan et al. (editors), Current Protocols in Immunology, John Wiley & Sons (including all updates until present).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Islet Autoimmunity in T1D

The objective of the study was to quantify and compare T cell responses to pancreatic islet autoantigens, immunodominant gluten peptides, and pathogen-derived recall antigens before and after oral gluten challenge in patients with both Type-1 diabetes (T1D) and Celiac disease.

Background

Dietary gluten may play a role in causing or enhancing islet autoimmunity, but the mechanism is not understood. In patient-based studies over the last 14-years, short-term "gluten challenge" has provided a detailed understanding of the immune response underlying Celiac disease. In the present study, gluten challenge was used for the first time to study patients affected by Celiac disease as well as T1D to detect CD4+ T cells specific for autoantigens implicated in T1D, and to test whether islet autoimmunity is affected by reactivation of gluten immunity.

In Celiac disease, the most prevalent genetic association is with the MHC-Class II alleles encoding HLA-DQ2.5, and gluten-derived epitopes recognized by Celiac disease-specific CD4+ T cells are preferentially presented by HLA-DQ2.5. Most of the 10% of patients with Celiac disease who are negative for HLA-DQA1*05 and DQB1*02, which encode HLA-DQ2.5, possess the HLA-DQA1*03 and DQB1*0302 alleles encoding HLA-DQ8, and in these patients distinctive gluten-specific epitopes are restricted by HLA-DQ8. The amino acid sequences of gluten-derived HLA-DQ2.5- and DQ8-restricted epitopes have been described (Sollid L M et al. Immunogenetics. 2012). Six-days after Celiac disease patients who usually exclude dietary gluten commence oral gluten challenge, certain gluten peptides stimulate interferon (IFN)-γ secretion when incubated with peripheral blood mononuclear cells (PBMC) or whole blood (Ontiveros N et al. Clin Exp Immunol 2014). IFN-γ secretion elicited by gluten peptides can be detected by ELISpot assay and is due to activated CD4+ T cells (Anderson R P et al., Nature Med 2000), which have been further characterized by flow cytometry using MHC-Class II multimers (Raki M et al., PNAS USA 2007). In HLA-DQ2.5+ Celiac disease patients who regularly consume gluten (untreated), the median frequency of circulating CD4+ T cells stained by HLA-DQ2.5 multimers specific for the two dominant wheat gluten epitopes is approximately 16 per million CD4+ T cells; and in HLA-DQ2.5+ Celiac disease patients who exclude dietary gluten the median frequency is 5 per million (Christophersen A. et al., UEGW J 2014). Oral gluten challenge transiently increases the frequencies of CD4+ T cells specific for dominant gluten epitopes by 10-100-fold (Anderson R P et al. Gut 2005; Raki M et al. PNAS USA 2007), allowing otherwise undetectable gluten epitope-specific T cells to be quantified and characterized by ex vivo IFN-γ secretion assays such as ELISpot using PBMC or ELISA using plasma from whole blood incubated with gluten peptides.

In recent studies using blood collected before and 6 days after oral gluten challenge in HLA-DQ2.5+ Celiac disease patients, IFN-γ inducible protein (IP)-10 and interleukin (IL)-2 were found to increase more consistently and to relatively higher concentrations in plasma from whole blood incubated with dominant gluten peptides. In the majority of patients, incubation of whole blood collected before oral gluten challenge with gluten peptides stimulated IP-10 and sometimes IL-2 levels that were significantly higher than whole blood incubated with culture medium alone. After oral gluten challenge, IP-10 and IL-2 as well as IFN-γ were elevated in whole blood incubated with gluten peptides.

This observation suggested that rare antigen-specific CD4+ T cells could be detected in cytokine release assays measuring IP-10 in plasma from whole blood incubated with candidate peptides encompassing cognate epitopes.

This novel approach to mapping epitopes for rare antigen-specific CD4+ T cells was tested in patients with Type-1 diabetes (T1D) who also had Celiac disease. T1D is also a T-cell mediated disease, but the epitopes recognized by disease-causing CD4+ T cells is unclear. The HLA-DR3-DQ2.5 and HLA-DR4-DQ8 haplotypes are strongly associated with T1D, and T-cell epitopes derived from autoantigens recognized by IgG in T1D have been reported. However, no single HLA-DR or DQ-restricted epitope has been consistently associated with T1D, and many regions of the most thoroughly studied islet autoantigens (preproinsulin, glutamic acid decarboxylase (GAD)-65, and insulinoma-associated antigen (IA)-2) are capable of being recognized by CD4+ T cells in MHC Class II transgenic mice, healthy human and/or T1D patients (Di Lorenzo T P et al., Clin Exp Immunol 2007).

In patients with T1D and Celiac disease, oral gluten challenge would allow CD4+ T cell responses to well-characterized gluten-derived epitopes to be used as a positive control for whole blood IFN-γ, IL-2 and IP-10 responses elicited by peptides derived from autoantigens implicated in T1D. Mapping epitopes relevant to T1D might then possible for the first time using fresh blood in overnight assays. In the current study, cytokine responses to pools and individual peptides encompassing all unique 12mers in the T1D autoantigens, preproinsulin, GAD65 and IA-2 were assessed before and after oral gluten challenge in T1D patients with Celiac disease following a gluten exclusion diet.

Methods

Subjects were eligible if they were adults aged 18-55 yrs, had not received immunosuppressive medication within the previous 3-months, and adhered to a gluten-free diet. All subjects had biopsy-confirmed Celiac disease and were also insulin-treated Type-1 diabetics. Autoantibodies associated with T1D and Celiac disease were assessed (Barbara Davis Center, Denver Colo.; and Quest Diagnostics). Each of the four subjects showed elevated insulin autoantibodies, but autoantibodies specific for glutamic acid decarboxylase (GAD), insulinoma-associated antigen (IA)-2, or zinc-transporter-8 were not detected (Table 1). MHC Class-II alleles were determined (Barbara Davis Center, Denver Colo.) and showed each of the four subjects possessed alleles encoding HLA-DR3 and HLA-DQ2.5, and three also possessed HLA-DR4 and DQ8 (Table 2). All subjects strictly adhered to a gluten free diet until undergoing a 3-day oral food challenge. The food consumed during the challenge consisted of cookies prepared from wheat gluten, and barley and rye flour. Three cookies consumed daily were estimated to provide a total of 4.5 g wheat gluten, 3 g barley hordein, and 1.5 g rye secalin. Heparinized blood was collected before and 6 days after commencing the oral food challenge.

TABLE 1

Subject demographics and serology

| Subject | Age | Sex | Glutamic acid decarboxylase IgG(N < 20; hi > 25 | IA-2 IgG (N < 5,; hi > 7) | Insulin IgG (N < 0.011, hi > 0.013) | ZnT8-IgG (N <0.021; hi > 0.030) | Deamidated gliadin peptide IgA(N < 20) IgA | tTG-IgA (N < 0.050; hi > 0.100) |
|---|---|---|---|---|---|---|---|---|
| 1 | 28 | M | 0 | 0 | 0.259 | −0.004 | 21 | 0.033 |
| 7 | 23 | F | 12 | 2 | 0.168 | −0.005 | 6 | 0.094 |
| 6 | 44 | M | 0 | 0 | 1.206 | −0.007 | 22 | 0.079 |
| 2 | 22 | M | 0 | 0 | 0.089 | −0.003 | 28 | 0.006 |

TABLE 2

MHC Class II alleles of Subjects

| Subject | T1D Susceptibility HLA-DR, and-DQ | HLA-DQA | HLA-DQA | HLA-DQB | HLA-DQB | HLA-DRB1 | HLA-DRB1 |
|---|---|---|---|---|---|---|---|
| 1 | DR3/4 DQ2.5/8 | 301 | 501 | 302 | 201 | 401 | 301 |
| 7 | DR3/4 DQ2.5/8 | 501 | 301 | 201 | 302 | 301 | 402 |
| 6 | DR3 DQ2.5 | 501 | 401 | 201 | 402 | 301 | 801 |
| 2 | DR3/4 DQ2.5/8 | 303 | 501 | 302 | 201 | 405 | 301 |

IFN-γ ELISpot and whole blood cytokine release assays were performed to assess T-cell responses to pools of 17mer peptides encompassing all unique 12mer amino-acid sequences derived from pancreatic islet antigens commonly recognized by autoantibodies in T1D: insulin, glutamic decarboxylase-65 (GAD65), and insulinoma-associated antigen (IA)-2 (purity 70% by HPLC, identity confirmed by LC-MS; synthesized by JPT Peptide Technologies GmbH, Germany) (Table 3). Libraries were designed according to Beissbarth et al (Bioninformatics T. et al. Suppl 1:i29-37) using protein sequences sourced from the public NCBI Genbank database (ncbi.nlm.nih.gov/protein). Table 3 summarizes the resulting peptide libraries.

TABLE 3

Islet autoantigen peptide libraries

| Library | Insulin | GAD65 | IA-2 |
|---|---|---|---|
| Antigen: | Preproinsulin | Glutamic decarboxylase 65 (GAD65) | Insulinoma antigen-2 (IA-2) or Tyrosine phosphatase like autoantigen (PTPRN) or (ICA512) |
| Search Items | "homo sapiens" and "preproinsulin", or "proinsulin", or "insulin" | "homo sapiens" and "glutamate decarboxylase", or "glutamic decarboxylase", or "glutamic" and "decarboxylase" and "65" | "Receptor-type tyrosine-protein phosphate-like N" |
| Genbank entries retrieved | 19 | 20 | 3 |
| Unique 12mers | 154 | 692 | 1141 |
| Total 17mers in library | 34 | 151 | 255 |
| Pools per library | 1 | 2 | 3 |
| 17mers per pool | 34 | 75 or 76 | 85 |

TABLE 3-continued

Islet autoantigen peptide libraries

| Library | Insulin | GAD65 | IA-2 |
|---|---|---|---|
| Deamidation - additional sequences generated with glutamate substitutions at potential deamidation sites[1] | 1 in AAP35454.1, AAA59179.1, AEG19452.1, and ABI63346.1 | 4 in NP_001127838.1, 1 in CAB62572.1, 4 in CAA49554.1, 2 in AAB28987.1, 1 in EAW86101.1, 2 in CAH73660.1, and 3 in CAH73658.1 | 15 in Q16849 |
| Genbank accession numbers: | 0601246A AAA59172.1 AAA59172.1 AAA59173.1 AAA59179.1 AAH05255.1 AAN39451.1 AAP35454.1 AAW83741.1 ABI63346.1 AEG19452.1 AFK93533.1 CAA08766.1 CAA23828.1 CAA49913.1 NP_000198.1 NP_001172026.1 NP_001172027.1 P01308.1 | EAW86103.1 AAA58491.1 AAA62367.1 AAB28987.1 AAI26328.1 AAI26330.1 AAP88040.1 CAA49554.1 CAB62572.1 CAC09233.1 CAH73658.1 CAH73659.1 CAH73660.1 EAW86101.1 EAW86102.1 EAW86104.1 NP_000809.1 NP_001127838.1 Q05329.1 Q5VZ30 | NP_001186692.1 NP_001186693.1 Q16849.1 |

[1]If a glutamine residue in the primary sequence conformed to the deamidation motif defined for transglutaminase-2 ($QX_1PX_3$, or $QX_1X_2[F,Y,W,I,L,V]$, where $X_1$ and $X_3$ are not proline) a second primary sequence was generated with glutamine replaced by glutamate. This deamidated primary sequences was included amongst those used to generate peptide libraries.

In addition, a pool of 3 gluten peptides consisting of immune-dominant HLA-DQ2.5-restricted T cell epitopes (95% purity by HPLC, identity confirmed by LC-MS; synthesized by CS Bio CA), a pool with 10 additional gluten peptides consisting of immuno-dominant HLA-DQ2.5, -DQ8, and DQ2.2 restricted T cell epitopes (90% purity by HPLC, identity confirmed by LC-MS; synthesized by Pepscan Netherlands), a pool of 14 gluten peptides consisting of 11 from the two smaller pools (90% purity by HPLC, identity confirmed by LC-MS; synthesized by Pepscan Netherlands), a pool of 71 gluten-derived peptides consisting of all the peptides in the three smaller pools as well as 55 additional peptides consisting of sequences implicated in HLA-DQ2.5-associated Celiac disease (purity 70% by HPLC, identity confirmed by LC-MS; JPT Peptide Technologies) (Tye-Din et al. Sci Transl Med 2010), and of 23 MHC class-I (CEF) (Product no. 3615-1, Mabtech AG, Sweden) and 14 MHC class-II restricted epitopes derived from recall viral antigens (PM-CEFT-MHC-II, JPT Peptide Technologies GmbH, Germany) were also assessed. Individual constituent peptides from the preproinsulin, GAD, IA-2 and gluten pools were assessed in whole blood cytokine release assays using blood collected 6 days after commencing oral gluten challenge.

In whole blood assays 225 μL volumes of fresh heparinized blood were incubated with 25 μL of peptide in phosphate buffered saline (PBS) with dimethylsulfoxide (DMSO) to a final concentration of 0.05% or 0.1% in 96-well round-bottom plates. Concentrations of constituent peptides in islet-autoantigen pools in whole blood assays were 0.4, 1 or 4 μg/mL; for CEF 0.1 μg/mL; CEFT 1 μg/mL; 3-gluten-peptide pool 10, 20 or 50 μg/mL, 13-gluten-peptide pool 5, 10, or 25 μg/mL; 14-gluten-peptide pool 5, 10, or 25 μg/mL; 71-gluten-peptide pool 1, 5 or 10 μg/mL. The final concentration of individual peptides incubated in whole blood with 10% PBS was 20 μg/mL with 0.0.5% DMSO. Whole blood assays were incubated for 24 hours at 37° C. in 5% $CO_2$. At the conclusion of the incubation period, approximately 120 μL plasma was separated from blood after centrifuging plates and then transferred to a corresponding well in a "mirror image" sterile 96-well plate. Plates containing plasma were sealed with adhesive plastic coverslips and frozen at −80° C. Multiplex bead-based cytokine assays (MAGPIX®) were performed on plasma thawed while being centrifuged at room temperature for 10 min. Plasma was pipetted directly into dedicated 96-well plates for magnetic bead-based assays to measure the concentrations of interferon (IFN)-γ-induced protein-10 (IP-10), interleukin (IL)-2 and IFN-γ. For peptide pools assessed before and after oral gluten challenge, triplicate plasma samples were assessed and the final concentration was expressed as the mean of triplicates after removal of outliers. The assay blank was determined by the mean levels of cytokines in plasma from blood incubated with 10% PBS and 0.1% DMSO. After oral gluten challenge, individual peptides in libraries were incubated in duplicate wells with whole blood. Plasma from duplicate wells was combined and assessed in triplicate wells for the multiplex cytokine assay. Each 96-well MAGPIX® plate was considered a separate assay that included 6 replicates with plasma from whole blood incubated with medium only. For each cytokine, a standard curve was determined using standards provided by the manufacturer from 3.2 to 10,000 pg/mL. If a cytokine concentration was reported as being <3.2 pg/mL a value of 3.2 pg/mL was recorded, and if >10,000 pg/mL a value of 10,000 pg/mL was recorded. Cytokine levels were considered elevated if the mean cytokine concentration in triplicate test wells was at least twice the mean level in 6 replicate wells in the same 96-well plate containing plasma from whole blood incubated with medium only.

In ELISpot assays, 0.4 million freshly isolated peripheral blood mononuclear cells (PBMC) re-suspended in 50 μL X-Vivo® serum-free medium were incubated with peptide pools dissolved in 40 μL X-Vivo® and 10 μL PBS. IFN-γ ELISpot assays were performed in pre-coated 96-well MAIP plates (Mabtech) that were incubated at 37° C. in 5% $CO_2$. After 18 h, PBMCs were discarded from ELISpot plates, and plates were washed and developed for later analysis by an automated ELISpot reader (Zellnet Inc., NJ). Spot forming counts were determined for each well.

Results

Gluten Peptide Pool Responses:

Cytokine release responses to pools and individual gluten-derived peptides were either unchanged or substantially increased after oral gluten challenge (Table 4 and Tables 5A-C). Amongst the whole blood cytokine release assays, responses to gluten peptides were least common and weakest in the whole blood IFN-γ release assay and most consistent and pronounced in the IP-10 assay after oral gluten challenge. However, IP-10 responses to the two larger gluten peptide pools were more than double those to medium alone in blood collected before as well as after oral gluten challenge in all four subjects. IL-2 responses to the highest concentrations (10-50 μg/mL) of gluten peptide pools were also more than double responses to medium alone in blood collected before oral gluten challenge in three subjects. Whole blood IFN-γ release and IFN-γ ELISpot responses to gluten peptide pools were not elevated before oral gluten challenge.

TABLE 4

| IFNg ELISpot responses[1] to peptide pools[2] | | | | | | | | |
|---|---|---|---|---|---|---|---|---|
| Subject | 1 | | 7 | | 6 | | 2 | |
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| Medium & PBMC 0.5% DMSO | 0 | 0 | 1 | 5 | 0 | 0 | 0 | 0 |
| Medium & PBMC 0.5% DMSO | 4 | 1 | 7 | 7 | 2 | 7 | 5 | 4 |
| Medium no PBMC 0.5% DMSO | 2 | 1 | 4 | 7 | 3 | 5 | 3 | 2 |
| PHA 10 ug/mL 0.5% DMSO | 2171 | 1730 | 1263 | 2109 | 1693 | 763 | 2487 | 2784 |
| Recall antigen pools | | | | | | | | |
| CEF each peptide 0.1 ug/mL | 249 | 75 | 12 | 45 | 42 | 74 | 11 | 14 |
| CEFT each peptide 1 ug/mL | 9 | 5 | 22 | 36 | 34 | 59 | 3 | 16 |
| Islet autoantigen-derived pools | | | | | | | | |
| Insulin-34 peptides 17mers 20 ug/mL | 222 | 147 | 92 | 410 | 141 | 25 | 261 | 338 |
| GAD65 pool 1-75 17mers 20 ug/mL | 21 | 1 | 11 | 20 | 5 | 21 | 8 | 7 |
| GAD 65 pool 2-76 17mers 20 ug/mL | 84 | 3 | 14 | 18 | 7 | 15 | 3 | 4 |
| IA2 pool 1-85 17mers 20 ug/mL | 6 | 3 | 8 | 17 | 19 | 32 | 2 | 7 |
| IA2 pool 2-85 17mers 20 ug/mL | 56 | 6 | 76 | 95 | 71 | 151 | 19 | 23 |
| IA2 pool 3-85 17mers 20 ug/mL | 23 | 1 | 9 | 22 | 24 | 40 | 3 | 7 |
| Gluten pools (epitope restrictions) | | | | | | | | |
| 71-peptides (DQ2.5/2.2/8) 50 uM | 2 | 4 | 8 | 53 | 8 | 354 | 2 | 11 |
| 14-peptides (DQ2.5/2.2/8) 25 uM | 2 | 4 | 8 | 53 | 8 | 354 | 2 | 11 |
| 13-peptides (DQ2.5/2.2/8) 25 uM | 2 | 2 | 4 | 65 | 2 | 281 | 3 | 9 |
| 3-peptides (DQ2.5) 50 ug/mL | 2 | 3 | 4 | 19 | 5 | 270 | 4 | 2 |

[1]Spot forming units (sum of 3 wells, 0.4 million PBMC per well)
[2]Pools with individual peptides at concentrations indicated in a final concentration of 0.5% DMSO

TABLE 5A

| | Whole blood IFNg release to Gluten Peptide Pools | | | | | | | |
|---|---|---|---|---|---|---|---|---|
| Subject | 1 | | 7 | | 6 | | 2 | |
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| | Concentration pg/mL | | | | | | | |
| Medium 0.05% | 55 | 66 | 239 | 150 | 97 | 98 | 3.8 | 4.9 |
| CEF 0.1 ug/mL | 44 | 53 | 458 | 172 | 96 | 85 | 4.0 | 4.4 |
| CEFT 1 ug/mL | 56 | 66 | 394 | 254 | 112 | 81 | 7.4 | 8.3 |
| 71-peptides (DQ2.5/2.2/8) 10 ug/mL | 76 | 75 | 391 | 247 | 93 | 277 | 6.2 | 25.1 |
| 71-peptides (DQ2.5/2.2/8) 5 ug/mL | 32 | 73 | 348 | 224 | 100 | 305 | 4.2 | 15.7 |
| 71-peptides (DQ2.5/2.2/8) 1 ug/mL | 87 | 71 | 201 | 216 | 83 | 185 | 3.5 | 13.3 |
| 14-peptides (DQ2.5/2.2/8) 25 uM | 54 | 78 | 450 | 238 | 83 | 105 | 6.5 | 4.5 |
| 14-peptides (DQ2.5/2.2/8) 10 uM | 52 | 63 | 154 | 201 | 74 | 109 | 3.7 | 3.9 |
| 14-peptides (DQ2.5/2.2/8) 5 uM | 43 | 65 | 133 | 213 | 91 | 136 | 3.8 | 6.8 |
| 13-peptides (DQ2.5/2.2/8) 25 uM | 71 | 69 | 454 | 220 | 90 | 198 | 4.0 | 8.1 |
| 13-peptides (DQ2.5/2.2/8) 10 uM | 60 | 76 | 424 | 409 | 74 | 163 | 3.2 | 9.8 |
| 13-peptides (DQ2.5/2.2/8) 5 uM | 51 | 76 | 169 | 292 | 93 | 134 | 3.2 | 12.7 |
| 3-peptides (DQ2.5) 50 ug/mL | 61 | 74 | 410 | 227 | 85 | 234 | 3.9 | 8.3 |
| 3-peptides (DQ2.5) 20 ug/mL | 58 | 58 | 78 | 266 | 98 | 245 | 3.2 | 5.8 |
| 3-peptides (DQ2.5) 10 ug/mL | 69 | 64 | 296 | 205 | 91 | 192 | 3.2 | 5.7 |
| (pE)PEQPIPEQPQPYPQQ-NH2 (SEQ ID NO: 42) 10 uM | 42 | 72 | 170 | 102 | 96 | 278 | 3.3 | 8.6 |
| (pE)QPFPQPEQPFPWQP-NH2 (SEQ ID NO: 43) 10 uM | 60 | 62 | 158 | 150 | 94 | 258 | 4.5 | 6.4 |
| (pE)LQPFPQPELPYPQPQ-NH2 (SEQ ID NO: 44) 10 uM | 39 | 55 | 407 | 194 | 102 | 200 | 4.1 | 13.9 |
| | Fold-change over medium only (bold >2) | | | | | | | |
| Medium 0.05% | 1.00 | 1.00 | 1.00 | 1.00 | 1.00 | 1.00 | 1.00 | 1.00 |
| CEF 0.1 ug/mL | 0.80 | 0.81 | 1.92 | 1.14 | 0.99 | 0.86 | 1.03 | 0.90 |
| CEFT 1ug/mL | 1.03 | 1.01 | 1.65 | 1.69 | 1.16 | 0.83 | 1.94 | 1.70 |
| 71-peptides (DQ2.5/2.2/8) 10 ug/mL | 1.39 | 1.14 | 1.64 | 1.64 | 0.97 | 2.83 | 1.62 | 5.15 |
| 71-peptides (DQ2.5/2.2/8) 5 ug/mL | 0.59 | 1.11 | 1.46 | 1.49 | 1.04 | 3.11 | 1.09 | 3.23 |
| 71-peptides (DQ2.5/2.2/8) 1 ug/mL | 1.59 | 1.08 | 0.84 | 1.44 | 0.86 | 1.89 | 0.90 | 2.74 |
| 14-peptides (DQ2.5/2.2/8) 25 uM | 0.99 | 1.19 | 1.88 | 1.58 | 0.85 | 1.07 | 1.71 | 0.93 |
| 14-peptides (DQ2.5/2.2/8) 10 uM | 0.96 | 0.95 | 0.65 | 1.34 | 0.76 | 1.11 | 0.96 | 0.80 |
| 14-peptides (DQ2.5/2.2/8) 5 uM | 0.79 | 0.98 | 0.56 | 1.41 | 0.94 | 1.39 | 0.98 | 1.40 |
| 13-peptides (DQ2.5/2.2/8) 25 uM | 1.30 | 1.04 | 1.90 | 1.46 | 0.94 | 2.02 | 1.03 | 1.66 |
| 13-peptides (DQ2.5/2.2/8) 10 uM | 1.10 | 1.16 | 1.77 | 2.72 | 0.76 | 1.66 | 0.84 | 2.01 |
| 13-peptides (DQ2.5/2.2/8) 5 uM | 0.93 | 1.15 | 0.71 | 1.94 | 0.96 | 1.36 | 0.84 | 2.61 |
| 3-peptides (DQ2.5) 50 ug/mL | 1.12 | 1.13 | 1.72 | 1.51 | 0.88 | 2.38 | 1.01 | 1.71 |
| 3-peptides (DQ2.5) 20 ug/mL | 1.06 | 0.88 | 0.33 | 1.77 | 1.01 | 2.50 | 0.84 | 1.18 |
| 3-peptides (DQ2.5) 10 ug/mL | 1.27 | 0.98 | 1.24 | 1.36 | 0.94 | 1.96 | 0.84 | 1.17 |
| (pE)PEQPIPEQPQPYPQQ-NH2 (SEQ ID NO: 42) 10 uM | 0.76 | 1.09 | 0.71 | 0.68 | 0.99 | 2.84 | 0.85 | 1.77 |
| (pE)QPFPQPEQPFPWQP-NH2 (SEQ ID NO: 43)10 uM | 1.09 | 0.95 | 0.66 | 1.00 | 0.98 | 2.63 | 1.19 | 1.32 |
| (pE)LQPFPQPELPYPQPQ-NH2 (SEQ ID NO: 44) 10 uM | 0.71 | 0.84 | 1.71 | 1.29 | 1.05 | 2.03 | 1.06 | 2.85 |

TABLE 5B

| Whole blood IL-2 release to Gluten Peptide Pools | | | | | | | | |
|---|---|---|---|---|---|---|---|---|
| Subject | 1 | | 7 | | 6 | | 2 | |
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| | Concentration pg/mL | | | | | | | |
| Medium 0.05% | 3.2 | 3.2 | 62.7 | 42.1 | 5.0 | 4.2 | 3.2 | 3.2 |
| CEF 0.1 ug/mL | 3.2 | 3.2 | 195.5 | 53.9 | 4.5 | 3.7 | 3.2 | 3.2 |
| CEFT 1 ug/mL | 3.2 | 3.2 | 228.5 | 135.5 | 22.2 | 20.8 | 6.5 | 7.4 |
| 71-peptides (DQ2.5/2.2/8) 10 ug/mL | 15.0 | 13.1 | 169.9 | 162.6 | 30.5 | 110.2 | 3.2 | 50.4 |
| 71-peptides (DQ2.5/2.2/8) 5 ug/mL | 3.7 | 26.5 | 118.5 | 117.2 | 36.6 | 139.3 | 3.2 | 19.0 |
| 71-peptides (DQ2.5/2.2/8) 1 ug/mL | 3.4 | 4.4 | 61.8 | 127.6 | 16.9 | 73.6 | 3.2 | 13.1 |
| 14-peptides (DQ2.5/2.2/8) 25 uM | 5.8 | 25.9 | 165.7 | 191.2 | 3.2 | 6.0 | 3.2 | 3.2 |
| 14-peptides (DQ2.5/2.2/8) 10 uM | 4.1 | 7.6 | 32.7 | 117.0 | 8.5 | 14.8 | 3.2 | 3.2 |
| 14-peptides (DQ2.5/2.2/8) 5 uM | 3.2 | 11.7 | 37.5 | 125.7 | 4.9 | 23.5 | 3.2 | 3.2 |
| 13-peptides (DQ2.5/2.2/8) 25 uM | 3.2 | 9.6 | 162.1 | 167.2 | 11.7 | 92.2 | 3.2 | 3.2 |
| 13-peptides (DQ2.5/2.2/8) 10 uM | 3.2 | 5.8 | 110.4 | 128.2 | 12.5 | 89.7 | 3.2 | 3.2 |
| 13-peptides (DQ2.5/2.2/8) 5 uM | 3.2 | 14.2 | 56.2 | 186.2 | 7.4 | 60.0 | 3.2 | 29.6 |
| 3-peptides (DQ2.5) 50 ug/mL | 3.2 | 10.6 | 149.5 | 121.4 | 7.6 | 82.6 | 3.2 | 3.2 |
| 3-peptides (DQ2.5) 20 ug/mL | 3.2 | 3.2 | 20.8 | 131.4 | 22.7 | 110.3 | 3.2 | 3.2 |
| 3-peptides (DQ2.5) 10 ug/mL | 3.2 | 5.6 | 92.8 | 106.5 | 9.0 | 58.0 | 3.2 | 3.2 |
| (pE)PEQPIPEQPQPYPQQ-NH2 (SEQ ID NO: 42) 10 uM | 3.2 | 3.2 | 106.1 | 27.8 | 23.3 | 134.3 | 3.2 | 22.4 |
| (pE)QPFPQPEQPFPWQP-NH2 (SEQ ID NO: 43) 10 uM | 3.2 | 3.2 | 41.4 | 55.1 | 17.9 | 115.9 | 3.2 | 5.2 |
| (pE)LQPFPQPELPYPQPQ-NH2 (SEQ ID NO: 44) 10 uM | 3.2 | 3.2 | 144.4 | 71.2 | 12.5 | 88.5 | 3.2 | 12.2 |
| | Fold-change over medium only (bold >2) | | | | | | | |
| Medium 0.05% | 1.00 | 1.00 | 1.00 | 1.00 | 1.00 | 1.00 | 1.00 | 1.00 |
| CEF 0.1 ug/mL | 1.00 | 1.00 | 3.12 | 1.28 | 0.91 | 0.87 | 1.00 | 1.00 |
| CEFT 1 ug/mL | 1.00 | 1.00 | 3.65 | 3.22 | 4.48 | 4.92 | 2.03 | 2.30 |
| 71-peptides (DQ2.5/2.2/8) 10 ug/mL | 4.70 | 4.11 | 2.71 | 3.86 | 6.17 | 25.99 | 1.00 | 15.75 |
| 71-peptides (DQ2.5/2.2/8) 5 ug/mL | 1.14 | 8.28 | 1.89 | 2.78 | 7.39 | 32.84 | 1.00 | 5.94 |
| 71-peptides (DQ2.5/2.2/8) 1 ug/mL | 1.06 | 1.38 | 0.99 | 3.03 | 3.42 | 17.36 | 1.00 | 4.10 |
| 14-peptides (DQ2.5/2.2/8) 25 uM | 1.82 | 8.08 | 2.64 | 4.54 | 0.65 | 1.41 | 1.00 | 1.00 |
| 14-peptides (DQ2.5/2.2/8) 10 uM | 1.28 | 2.38 | 0.52 | 2.78 | 1.72 | 3.48 | 1.00 | 1.00 |
| 14-peptides (DQ2.5/2.2/8) 5 uM | 1.00 | 3.65 | 0.60 | 2.99 | 0.99 | 5.55 | 1.00 | 1.00 |
| 13-peptides (DQ2.5/2.2/8) 25 uM | 1.00 | 2.99 | 2.59 | 3.97 | 2.36 | 21.74 | 1.00 | 1.00 |
| 13-peptides (DQ2.5/2.2/8) 10 uM | 1.00 | 1.82 | 1.76 | 3.04 | 2.52 | 21.16 | 1.00 | 1.00 |
| 13-peptides (DQ2.5/2.2/8) 5 uM | 1.00 | 4.44 | 0.90 | 4.42 | 1.49 | 14.16 | 1.00 | 9.25 |
| 3-peptides (DQ2.5) 50 ug/mL | 1.00 | 3.30 | 2.39 | 2.88 | 1.53 | 19.49 | 1.00 | 1.00 |
| 3-peptides (DQ2.5) 20 ug/mL | 1.00 | 1.00 | 0.33 | 3.12 | 4.58 | 26.02 | 1.00 | 1.00 |
| 3-peptides (DQ2.5) 10 ug/mL | 1.00 | 1.75 | 1.48 | 2.53 | 1.81 | 13.67 | 1.00 | 1.00 |
| (pE)PEQPIPEQPQPYPQQ-NH2 (SEQ ID NO: 42) 10 uM | 1.00 | 1.00 | 1.69 | 0.66 | 4.71 | 31.67 | 1.00 | 7.00 |
| (pE)QPFPQPEQPFPWQP-NH2 (SEQ ID NO: 43) 10 uM | 1.00 | 1.00 | 0.66 | 1.31 | 3.62 | 27.33 | 1.00 | 1.61 |

TABLE 5B-continued

Whole blood IL-2 release to Gluten Peptide Pools

| Subject | 1 | | 7 | | 6 | | 2 | |
|---|---|---|---|---|---|---|---|---|
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| (pE)LQPFPQPELPYPQPQ-NH2 (SEQ ID NO: 44) 10 uM | 1.00 | 1.00 | 2.30 | 1.69 | 2.52 | 20.88 | 1.00 | 3.82 |

TABLE 5C

Whole blood IP-10 release to Gluten Peptide Pools

| Subject | 1 | | 7 | | 6 | | 2 | |
|---|---|---|---|---|---|---|---|---|
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| | Concentration pg/mL | | | | | | | |
| Medium 0.05% | 266 | 335 | 743 | 892 | 277 | 201 | 266 | 312 |
| CEF 0.1 ug/mL | 225 | 346 | 1211 | 764 | 318 | 644 | 241 | 282 |
| CEFT 1 ug/mL | 586 | 604 | 10000 | 10000 | 5439 | 8789 | 937 | 1235 |
| 71-peptides (DQ2.5/2.2/8) 10 ug/mL | 688 | 1546 | 1805 | 10000 | 3479 | 10000 | 561 | 3696 |
| 71-peptides (DQ2.5/2.2/8) 5 ug/mL | 763 | 3100 | 1212 | 10000 | 3143 | 10000 | 464 | 2957 |
| 71-peptides (DQ2.5/2.2/8) 1 ug/mL | 582 | 854 | 2061 | 10000 | 2744 | 10000 | 578 | 1969 |
| 14-peptides (DQ2.5/2.2/8) 25 uM | 949 | 2132 | 2662 | 10000 | 219 | 1852 | 266 | 265 |
| 14-peptides (DQ2.5/2.2/8) 10 uM | 326 | 1554 | 1378 | 10000 | 902 | 3621 | 242 | 273 |
| 14-peptides (DQ2.5/2.2/8) 5 uM | 226 | 852 | 1448 | 10000 | 523 | 9960 | 271 | 540 |
| 13-peptides (DQ2.5/2.2/8) 25 uM | 328 | 945 | 1482 | 10000 | 886 | 10000 | 258 | 421 |
| 13-peptides (DQ2.5/2.2/8) 10 uM | 264 | 1010 | 907 | 10000 | 1238 | 10000 | 214 | 1330 |
| 13-peptides (DQ2.5/2.2/8) 5 uM | 234 | 1379 | 910 | 10000 | 448 | 10000 | 252 | 2724 |
| 3-peptides (DQ2.5) 50 ug/mL | 233 | 980 | 955 | 10000 | 320 | 10000 | 228 | 498 |
| 3-peptides (DQ2.5) 20 ug/mL | 249 | 419 | 536 | 10000 | 2479 | 10000 | 229 | 671 |
| 3-peptides (DQ2.5) 10 ug/mL | 316 | 643 | 843 | 10000 | 1329 | 10000 | 253 | 695 |
| (pE)PEQPIPEQPQPYPQQ-NH2 (SEQ ID NO: 42) 10 uM | 235 | 325 | 713 | 2549 | 3409 | 10000 | 336 | 1269 |
| (pE)QPFPQPEQPFPWQP-NH2 (SEQ ID NO: 43) 10 uM | 218 | 501 | 900 | 10000 | 1934 | 10000 | 376 | 1140 |
| (pE)LQPFPQPELPYPQPQ-NH2 (SEQ ID NO: 44) 10 uM | 201 | 384 | 977 | 3293 | 1616 | 10000 | 320 | 1844 |
| | Fold-change over medium only (bold >2) | | | | | | | |
| Medium 0.05% | 1.00 | 1.00 | 1.00 | 1.00 | 1.00 | 1.00 | 1.00 | 1.00 |
| CEF 0.1 ug/mL | 0.85 | 1.03 | 1.63 | 0.86 | 1.15 | 3.21 | 0.91 | 0.90 |
| CEFT 1 ug/mL | 2.21 | 1.80 | 13.46 | 11.21 | 19.62 | 43.73 | 3.53 | 3.95 |
| 71-peptides (DQ2.5/2.2/8) 10 ug/mL | 2.59 | 4.61 | 2.43 | 11.21 | 12.55 | 49.76 | 2.11 | 11.83 |
| 71-peptides (DQ2.5/2.2/8) 5 ug/mL | 2.87 | 9.25 | 1.63 | 11.21 | 11.34 | 49.76 | 1.75 | 9.47 |
| 71-peptides (DQ2.5/2.2/8) 1 ug/mL | 2.19 | 2.55 | 2.77 | 11.21 | 9.90 | 49.76 | 2.18 | 6.30 |
| 14-peptides (DQ2.5/2.2/8) 25 uM | 3.58 | 6.36 | 3.58 | 11.21 | 0.79 | 9.21 | 1.00 | 0.85 |

TABLE 5C-continued

Whole blood IP-10 release to Gluten Peptide Pools

| Subject | 1 | | 7 | | 6 | | 2 | |
|---|---|---|---|---|---|---|---|---|
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| 14-peptides (DQ2.5/2.2/8) 10 uM | 1.23 | 4.64 | 1.85 | 11.21 | 3.25 | 18.02 | 0.91 | 0.87 |
| 14-peptides (DQ2.5/2.2/8) 5 uM | 0.85 | 2.54 | 1.95 | 11.21 | 1.89 | 49.56 | 1.02 | 1.73 |
| 13-peptides (DQ2.5/2.2/8) 25 uM | 1.24 | 2.82 | 1.99 | 11.21 | 3.19 | 49.76 | 0.97 | 1.35 |
| 13-peptides (DQ2.5/2.2/8) 10 uM | 1.00 | 3.01 | 1.22 | 11.21 | 4.47 | 49.76 | 0.81 | 4.26 |
| 13-peptides (DQ2.5/2.2/8) 5 uM | 0.88 | 4.11 | 1.23 | 11.21 | 1.62 | 49.76 | 0.95 | 8.72 |
| 3-peptides (DQ2.5) 50 ug/mL | 0.88 | 2.92 | 1.29 | 11.21 | 1.16 | 49.76 | 0.86 | 1.60 |
| 3-peptides (DQ2.5) 20 ug/mL | 0.94 | 1.25 | 0.72 | 11.21 | 8.94 | 49.76 | 0.86 | 2.15 |
| 3-peptides (DQ2.5) 10 ug/mL | 1.19 | 1.92 | 1.14 | 11.21 | 4.79 | 49.76 | 0.95 | 2.22 |
| (pE)PEQPIPEQPQPYPQQ-NH2 (SEQ ID NO: 42) 10 uM | 0.89 | 0.97 | 0.96 | 2.86 | 12.30 | 49.76 | 1.26 | 4.06 |
| (pE)QPFPQPEQPFPWQP-NH2 (SEQ ID NO: 43) 10 uM | 0.82 | 1.49 | 1.21 | 11.21 | 6.98 | 49.76 | 1.42 | 3.65 |
| (pE)LQPFPQPELPYPQPQ-NH2 (SEQ ID NO: 44) 10 uM | 0.76 | 1.15 | 1.32 | 3.69 | 5.83 | 49.76 | 1.20 | 5.90 |

T1D Autoantigen Peptide Pool Responses:

Responses to T1D autoantigen peptide pools in cytokine release assays, especially whole blood IP-10 release, were frequently elevated (Table 4 and Tables 6A-C). The highest concentration of peptide pools tested (4 µg/mL) almost always stimulated stronger responses than the lowest concentration (0.4 µg/mL). With the exception of pool 1 for GAD65 in one patient, each of the eight T1D autoantigen peptide pools elicited whole blood IP-10 responses that were more than double those to medium alone in all four subjects. The preproinsulin pool and IA-2 pool 2 frequently stimulated strongest cytokine release responses, especially in the IFN-γ ELISpot. Consistency and magnitude of cytokine release stimulated by T1D autoantigen peptide pools was not consistently changed after oral gluten challenge.

TABLE 6A

Whole blood IFNg release to Islet-autoantigen Peptide Pools

| Subject | 1 | | 7 | | 6 | | 2 | |
|---|---|---|---|---|---|---|---|---|
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| | Concentration pg/mL | | | | | | | |
| Medium 0.05% | 91 | 117 | 473 | 78 | 88 | 105 | 4.5 | 6.4 |
| CEF 0.1 ug/mL | 64 | 123 | 496 | 114 | 74 | 107 | 4.0 | 5.7 |
| CEFT 1 ug/mL | 58 | 105 | 553 | 113 | 82 | 113 | 6.3 | 5.9 |
| Insulin-34 peptides 17mers 4 ug/mL | 76 | 149 | 910 | 211 | 111 | 124 | 24.2 | 47.7 |
| Insulin-34 peptides 17mers 1 ug/mL | 69 | 111 | 678 | 105 | 90 | 97 | 11.4 | 11.0 |
| Insulin-34 peptides 17mers 0.4 ug/mL | 66 | 129 | 461 | 65 | 85 | 86 | 4.8 | 6.8 |
| GAD65 pool 1-75 17mers 4 ug/mL | 80 | 167 | 650 | 226 | 108 | 104 | 6.7 | 8.8 |
| GAD65 pool 1-75 17mers 1 ug/mL | 67 | 72 | 807 | 77 | 90 | 98 | 3.5 | 5.5 |
| GAD 65 pool 1-75 17mers 0.4 ug/mL | 67 | 121 | 592 | 59 | 75 | 85 | 4.0 | 5.4 |
| GAD65 pool 2-76 17mers 4 ug/mL | 84 | 126 | 532 | 139 | 113 | 106 | 6.4 | 10.7 |
| GAD65 pool 2-76 17mers 1 ug/mL | 67 | 124 | 597 | 146 | 76 | 105 | 6.2 | 7.7 |
| GAD65 pool 2-76 17mers 0.4 ug/mL | 56 | 131 | 592 | 87 | 70 | 96 | 7.3 | 6.0 |
| IA2 pool 1-85 17mers 4 ug/mL | 142 | 118 | 563 | 142 | 108 | 98 | 8.0 | 9.1 |
| IA2 pool 1-85 17mers 1 ug/mL | 64 | 62 | 517 | 99 | 74 | 81 | 3.5 | 5.7 |
| IA2 pool 1-85 17mers 0.4 ug/mL | 71 | 127 | 496 | 105 | 66 | 93 | 4.8 | 4.1 |
| IA2 pool 2-85 17mers 4 ug/mL | 68 | 164 | 509 | 173 | 146 | 140 | 31.9 | 32.5 |
| IA2 pool 2-85 17mers 1 ug/mL | 103 | 131 | 318 | 71 | 94 | 126 | 9.3 | 8.8 |
| IA2 pool 2-85 17mers 0.4 ug/mL | 74 | 29 | 472 | 163 | 76 | 87 | 5.6 | 4.6 |
| IA2 pool 3-85 17mers 4 ug/mL | 71 | 82 | 198 | 75 | 95 | 91 | 13.0 | 8.7 |
| IA2 pool 3-85 17mers 1 ug/mL | 53 | 90 | 258 | 44 | 70 | 73 | 4.1 | 6.3 |
| IA2 pool 3-85 17mers 0.4 ug/mL | 64 | 111 | 453 | 92 | 71 | 70 | 4.2 | 5.0 |

TABLE 6A-continued

Whole blood IFNg release to Islet-autoantigen Peptide Pools

| Subject | 1 | | 7 | | 6 | | 2 | |
|---|---|---|---|---|---|---|---|---|
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| | Fold-change over medium only (bold >2) | | | | | | | |
| Medium 0.05% | 1.00 | 1.00 | 1.00 | 1.00 | 1.00 | 1.00 | 1.00 | 1.00 |
| CEF 0.1 ug/mL | 0.70 | 1.05 | 1.05 | 1.46 | 0.84 | 1.02 | 0.88 | 0.89 |
| CEFT 1 ug/mL | 0.63 | 0.90 | 1.17 | 1.44 | 0.93 | 1.07 | 1.40 | 0.93 |
| Insulin-34 peptides 17mers 4 ug/mL | 0.83 | 1'27 | 1.92 | 2.69 | 1.26 | 1.18 | 5.41 | 7.49 |
| Insulin-34 peptides 17mers 1 ug/mL | 0.75 | 0'94 | 1.43 | 1.35 | 1.01 | 0.92 | 2.54 | 1.73 |
| Insulin-34 peptides 17mers 0.4 ug/mL | 0.72 | 1.10 | 0.97 | 0.83 | 0.96 | 0.82 | 1.08 | 1.06 |
| GAD65 pool 1-75 17mers 4 ug/mL | 0.87 | 1.43 | 1.37 | 2.89 | 1.22 | 0.99 | 1.50 | 1.37 |
| GAD65 pool 1-75 17mers 1 ug/mL | 0.73 | 0.61 | 1.28 | 0.98 | 1.01 | 0.94 | 0.77 | 0.86 |
| GAD65 pool 1-75 17mers 0.4 ug/mL | 0.74 | 1.03 | 1.25 | 0.76 | 0.85 | 0.81 | 0.88 | 0.84 |
| GAD65 pool 2-76 17mers 4 ug/mL | 0.92 | 1.08 | 1.12 | 1.78 | 1.28 | 1.01 | 1.43 | 1.68 |
| GAD65 pool 2-76 17mers 1 ug/mL | 0.74 | 1.06 | 1.26 | 1.87 | 0.86 | 1.01 | 1.38 | 1.21 |
| GAD65 pool 2-76 17mers 0.4 ug/mL | 0.61 | 1.12 | 1.25 | 1.12 | 0.80 | 0.91 | 1.63 | 0.94 |
| IA2 pool 1-85 17mers 4 ug/mL | 1.56 | 1.01 | 1.19 | 1.82 | 1.22 | 0.93 | 1.78 | 1.43 |
| IA2 pool 1-85 17mers 1 ug/mL | 0.71 | 0.53 | 1.09 | 1.27 | 0.84 | 0.78 | 0.77 | 0.89 |
| IA2 pool 1-85 17mers 0.4 ug/mL | 0.78 | 1.09 | 1.05 | 1.34 | 0.75 | 0.89 | 1.08 | 0.65 |
| IA2 pool 2-85 17mers 4 ug/mL | 0.74 | 1.40 | 1.07 | 2.21 | 1.65 | 1.33 | 7.11 | 5.10 |
| IA2 pool 2-85 17mers 1 ug/mL | 1.13 | 1.12 | 0.67 | 0.91 | 1.06 | 1.20 | 2.08 | 1.37 |
| IA2 pool 2-85 17mers 0.4 ug/mL | 0.81 | 0.24 | 1.00 | 2.08 | 0.86 | 0.83 | 1.26 | 0.71 |
| IA2 pool 3-85 17mers 4 ug/mL | 0.78 | 0.70 | 0.42 | 0.96 | 1.08 | 0.87 | 2.90 | 1.36 |
| IA2 pool 3-85 17mers 1 ug/mL | 0.58 | 0.77 | 0.55 | 0.56 | 0.79 | 0.70 | 0.90 | 0.98 |
| IA2 pool 3-85 17mers 0.4 ug/mL | 0.70 | 0.95 | 0.96 | 1.18 | 0.80 | 0.67 | 0.93 | 0.78 |

TABLE 6B

Whole blood IL-2 release to Islet-autoantigen Peptide Pools

| Subject | 1 | | 7 | | 6 | | 2 | |
|---|---|---|---|---|---|---|---|---|
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| | Concentration pg/mL | | | | | | | |
| Medium 0.05% | 3.2 | 3.2 | 162 | 23 | 3.6 | 4.3 | 3.2 | 3.2 |
| CEF 0.1ug/mL | 3.2 | 3.2 | 211 | 33 | 3.2 | 5.0 | 3.2 | 3.2 |
| CEFT 1 ug/mL | 3.2 | 3.2 | 236 | 47 | 17.1 | 24.4 | 8.4 | 3.2 |
| Insulin-34 peptides 17mers 4 ug/mL | 5.2 | 6.3 | 311 | 94 | 15.8 | 16.7 | 21.7 | 34.0 |
| Insulin-34 peptides 17mers 1 ug/mL | 5.1 | 3.2 | 205 | 34 | 5.8 | 5.0 | 6.4 | 3.2 |
| Insulin-34 peptides 17mers 0.4 ug/mL | 3.2 | 3.2 | 136 | 19 | 3.5 | 3.2 | 3.2 | 3.2 |
| GAD 65 pool 1-75 17mers 4 ug/mL | 14.0 | 3.2 | 236 | 95 | 10.4 | 7.2 | 3.2 | 3.2 |
| GAD65 pool 1-75 17mers 1 ug/mL | 3.2 | 3.2 | 216 | 23 | 3.6 | 4.8 | 3.2 | 3.2 |
| GAD6 5pool 1-75 17mers 0.4 ug/mL | 3.2 | 3.2 | 181 | 18 | 3.2 | 3.2 | 3.2 | 3.2 |
| GAD65 pool 2-76 17mers 4 ug/mL | 6.0 | 3.2 | 190 | 55 | 14.2 | 9.7 | 3.2 | 3.2 |
| GAD65 pool 2-76 17mers 1 ug/mL | 4.2 | 3.2 | 193 | 28 | 7.1 | 5.6 | 6.4 | 3.2 |
| GAD65 pool 2-76 17mers 0.4 ug/mL | 3.2 | 3.2 | 213 | 28 | 5.2 | 3.9 | 3.2 | 3.2 |
| IA2 pool 1-85 17mers 4 ug/mL | 46.1 | 5.4 | 264 | 83 | 23.0 | 18.7 | 37.5 | 56.3 |
| IA2 pool 1-85 17mers 1 ug/mL | 3.2 | 3.2 | 172 | 32 | 4.8 | 7.1 | 20.5 | 12.1 |
| IA2 pool 1-85 17mers 0.4 ug/mL | 3.2 | 3.2 | 168 | 30 | 3.2 | 3.2 | 3.2 | 3.2 |
| IA2 pool 2-85 17mers 4 ug/mL | 3.8 | 21.6 | 170 | 85 | 44.9 | 27.6 | 40.2 | 39.4 |
| IA2 pool 2-85 17mers 1 ug/mL | 23.9 | 6.2 | 77 | 21 | 12.2 | 21.7 | 14.6 | 3.2 |
| IA2 pool 2-85 17mers 0.4 ug/mL | 6.6 | 3.2 | 203 | 55 | 3.8 | 4.2 | 3.2 | 3.2 |
| IA2 pool 3-85 17mers 4 ug/mL | 3.2 | 3.2 | 10 | 12 | 5.2 | 6.2 | 33.3 | 29.1 |
| IA2 pool 3-85 17mers 1 ug/mL | 3.2 | 3.2 | 67 | 10 | 3.2 | 3.2 | 14.6 | 14.8 |
| IA2 pool 3-85 17mers 0.4 ug/mL | 3.2 | 3.2 | 190 | 29 | 3.2 | 3.2 | 21.3 | 3.2 |

TABLE 6B-continued

Whole blood IL-2 release to Islet-autoantigen Peptide Pools

| Subject | 1 | | 7 | | 6 | | 2 | |
|---|---|---|---|---|---|---|---|---|
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| | Fold-change over medium only (bold >2) | | | | | | | |
| Medium 0.05% | 1.00 | 1.00 | 1.00 | 1.00 | 1.00 | 1.00 | 1.00 | 1.00 |
| CEF 0.1 ug/mL | 1.00 | 1.00 | 1.30 | 1.41 | 0.88 | 1.15 | 1.00 | 1.00 |
| CEFT 1 ug/mL | 1.00 | 1.00 | 1.46 | 2.03 | 4.72 | 5.65 | 2.62 | 1.00 |
| Insulin-34 peptides 17mers 4 ug/mL | 1.63 | 1.97 | 1.92 | 4.08 | 4.36 | 3.88 | 6.78 | 10.62 |
| Insulin-34 peptides 17mers 1 ug/mL | 1.60 | 1.00 | 1.27 | 1.47 | 1.59 | 1.16 | 2.00 | 1.00 |
| Insulin-34 peptides 17mers 0.4 ug/mL | 1.00 | 1.00 | 0.84 | 0.84 | 0.95 | 0.74 | 1.00 | 1.00 |
| GAD65 pool 1-75 17mers 4 ug/mL | 4.37 | 1.00 | 1.46 | 4.09 | 2.88 | 1.66 | 1.00 | 1.00 |
| GAD65 pool 1-75 17mers 1 ug/mL | 1.00 | 1.00 | 1.34 | 1.00 | 1.00 | 1.10 | 1.00 | 1.00 |
| GAD65 pool 1-75 17mers 0.4 ug/mL | 1.00 | 1.00 | 1.12 | 0.79 | 0.88 | 0.74 | 1.00 | 1.00 |
| GAD65 pool 2-76 17mers 4 ug/mL | 1.86 | 1.00 | 1.18 | 2.37 | 3.92 | 2.24 | 1.00 | 1.00 |
| GAD65 pool 2-76 17mers 1 ug/mL | 1.32 | 1.00 | 1.19 | 1.19 | 1.97 | 1.29 | 2.01 | 1.00 |
| GAD65 pool 2-76 17mers 0.4 ug/mL | 1.00 | 1.00 | 1.32 | 1.22 | 1.45 | 0.90 | 1.00 | 1.00 |
| IA2 pool 1-85 17mers 4 ug/mL | 14.41 | 1.70 | 1.63 | 3.61 | 6.35 | 4.34 | 11.71 | 17.59 |
| IA2 pool 1-85 17mers 1 ug/mL | 1.00 | 1.00 | 1.06 | 1.39 | 1.32 | 1.65 | 6.40 | 3.77 |
| IA2 pool 1-85 17mers 0.4 ug/mL | 1.00 | 1.00 | 1.04 | 1.28 | 0.88 | 0.75 | 1.00 | 1.00 |
| IA2 pool 2-85 17mers 4 ug/mL | 1.19 | 6.74 | 1.05 | 3.70 | 12.40 | 6.39 | 12.57 | 12.30 |
| IA2 pool 2-85 17mers 1 ug/mL | 7.48 | 1.93 | 0.48 | 0.90 | 3.36 | 5.03 | 4.56 | 1.00 |
| IA2 pool 2-85 17mers 0.4 ug/mL | 2.05 | 1.00 | 1.25 | 2.36 | 1.04 | 0.98 | 1.00 | 1.00 |
| IA2 pool 3-85 17mers 4 ug/mL | 1.00 | 1.00 | 0.06 | 0.51 | 1.45 | 1.43 | 10.40 | 9.09 |
| IA2 pool 3-85 17mers 1 ug/mL | 1.00 | 1.00 | 0.41 | 0.44 | 0.88 | 0.74 | 4.57 | 4.63 |
| IA2 pool 3-85 17mers 0.4 ug/mL | 1.00 | 1.00 | 1.18 | 1.24 | 0.88 | 0.74 | 6.67 | 1.00 |

TABLE 6C

Whole blood IP-10 release to Islet-autoantigen Peptide Pools

| Subject | 1 | | 7 | | 6 | | 2 | |
|---|---|---|---|---|---|---|---|---|
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| | Concentration pg/mL | | | | | | | |
| Medium 0.05% | 10000 | 342 | 861 | 599 | 260 | 206 | 309 | 359 |
| CEF 0.1 ug/mL | 264 | 325 | 775 | 658 | 716 | 399 | 270 | 303 |
| CEFT 1 ug/mL | 275 | 355 | 7407 | 5957 | 5857 | 9218 | 815 | 887 |
| Insulin-34 peptides 17mers 4 ug/mL | 3183 | 9830 | 10000 | 10000 | 10000 | 10000 | 7297 | 5697 |
| Insulin-34 peptides 17mers 1 ug/mL | 4716 | 3055 | 10000 | 7466 | 2606 | 3322 | 4015 | 3093 |
| Insulin-34 peptides 17mers 0.4 ug/mL | 579 | 986 | 2281 | 1361 | 365 | 343 | 308 | 772 |
| GAD65 pool 1-75 17mers 4 ug/mL | 1913 | 1568 | 2171 | 1157 | 5406 | 1264 | 580 | 565 |
| GAD65 pool 1-75 17mers 1 ug/mL | 663 | 906 | 1130 | 681 | 681 | 462 | 334 | 370 |
| GAD65 pool 1-75 17mers 0.4 ug/mL | 284 | 608 | 967 | 797 | 326 | 294 | 382 | 327 |
| GAD65 pool 2-76 17mers 4 ug/mL | 5459 | 793 | 10000 | 9488 | 1972 | 2608 | 465 | 902 |
| GAD65 pool 2-76 17mers 1 ug/mL | 2180 | 903 | 10000 | 3692 | 3112 | 1225 | 1535 | 752 |
| GAD65 pool 2-76 17mers 0.4 ug/mL | 541 | 657 | 5150 | 1618 | 1800 | 1061 | 263 | 619 |
| IA2 pool 1-85 17mers 4 ug/mL | 10000 | 2496 | 10000 | 9969 | 4531 | 2775 | 1528 | 1376 |
| IA2 pool 1-85 17mers 1 ug/mL | 3121 | 1146 | 3363 | 1259 | 1450 | 1884 | 543 | 586 |
| IA2 pool 1-85 17mers 0.4 ug/mL | 1347 | 838 | 1296 | 836 | 264 | 300 | 298 | 299 |
| IA2 pool 2-85 17mers 4 ug/mL | 1653 | 5006 | 10000 | 10000 | 10000 | 10000 | 4721 | 5850 |

TABLE 6C-continued

Whole blood IP-10 release to Islet-autoantigen Peptide Pools

| Subject | 1 | | 7 | | 6 | | 2 | |
|---|---|---|---|---|---|---|---|---|
| HLA-DR | 3, 4 | | 3, 4 | | 3 | | 3, 4 | |
| HLA-DQ | 2.5, 8 | | 2.5, 8 | | 2.5 | | 2.5, 8 | |
| Days since commencing oral challenge | 0 | 6 | 0 | 6 | 0 | 6 | 0 | 6 |
| IA2 pool 2-85 17mers 1 ug/mL | 8939 | 3346 | 10000 | 4159 | 7063 | 10000 | 2118 | 1183 |
| IA2 pool 2-85 17mers 0.4 ug/mL | 1442 | 427 | 1799 | 3332 | 2153 | 2902 | 418 | 273 |
| IA2 pool 3-85 17mers 4 ug/mL | 255 | 801 | 1194 | 897 | 1130 | 646 | 1984 | 1351 |
| IA2 pool 3-85 17mers 1 ug/mL | 752 | 789 | 986 | 553 | 307 | 253 | 386 | 619 |
| IA2 pool 3-85 17mers 0.4 ug/mL | 502 | 386 | 921 | 2347 | 234 | 197 | 360 | 344 |
| | Fold-change over medium only (bold > 2) | | | | | | | |
| Medium 0.05% | 37.89 | 1.00 | 1.00 | 1.00 | 1.00 | 1.00 | 1.00 | 1.00 |
| CEF 0.1ug/mL | 1.00 | 0.95 | 0.90 | 1.10 | 2.76 | 1.94 | 0.87 | 0.84 |
| CEFT 1 ug/mL | 1.04 | 1.04 | 8.60 | 9.94 | 22.53 | 44.82 | 2.63 | 2.47 |
| Insulin-34 peptides 17mers 4 ug/mL | 12.06 | 28.71 | 11.61 | 16.68 | 38.46 | 48.62 | 23.58 | 15.85 |
| Insulin-34 peptides 17mers 1 ug/mL | 17.87 | 8.92 | 11.61 | 12.46 | 10.02 | 16.15 | 12.98 | 8.60 |
| Insulin-34 peptides 17mers 0.4 ug/mL | 2.19 | 2.88 | 2.65 | 2.27 | 1.40 | 1.67 | 1.00 | 2.15 |
| GAD65 pool 1-75 17mers 4 ug/mL | 7.25 | 4.58 | 2.52 | 1.93 | 20.79 | 6.15 | 1.88 | 1.57 |
| GAD65 pool 1-75 17mers 1 ug/mL | 2.51 | 2.65 | 1.31 | 1.14 | 2.62 | 2.25 | 1.08 | 1.03 |
| GAD65 pool 1-75 17mers 0.4 ug/mL | 1.07 | 1.78 | 1.12 | 1.33 | 1.25 | 1.43 | 1.24 | 0.91 |
| GAD65 pool 2-76 17mers 4 ug/mL | 20.68 | 2.32 | 11.61 | 15.83 | 7.58 | 12.68 | 1.50 | 2.51 |
| GAD65 pool 2-76 17mers 1 ug/mL | 8.26 | 2.64 | 11.61 | 6.16 | 11.97 | 5.96 | 4.96 | 2.09 |
| GAD65 pool 2-76 17mers 0.4 ug/mL | 2.05 | 1.92 | 5.98 | 2.70 | 6.92 | 5.16 | 0.85 | 1.72 |
| IA2 pool 1-85 17mers 4 ug/mL | 37.89 | 7.29 | 11.61 | 16.63 | 17.43 | 13.49 | 4.94 | 3.83 |
| IA2 pool 1-85 17mers 1 ug/mL | 11.82 | 3.35 | 3.91 | 2.10 | 5.58 | 9.16 | 1.76 | 1.63 |
| IA2 pool 1-85 17mers 0.4 ug/mL | 5.10 | 2.45 | 1.50 | 1.39 | 1.01 | 1.46 | 0.96 | 0.83 |
| IA2 pool 2-85 17mers 4 ug/mL | 6.26 | 14.62 | 11.61 | 16.68 | 38.46 | 48.62 | 15.26 | 16.27 |
| IA2 pool 2-85 17mers 1 ug/mL | 33.87 | 9.77 | 11.61 | 6.94 | 27.17 | 48.62 | 6.84 | 3.29 |
| IA2 pool 2-85 17mers 0.4 ug/mL | 5.46 | 1.25 | 2.09 | 5.56 | 8.28 | 14.11 | 1.35 | 0.76 |
| IA2 pool 3-85 17mers 4 ug/mL | 0.97 | 2.34 | 1.39 | 1.50 | 4.35 | 3.14 | 6.41 | 3.76 |
| IA2 pool 3-85 17mers 1 ug/mL | 2.85 | 2.31 | 1.15 | 0.92 | 1.18 | 1.23 | 1.25 | 1.72 |
| IA2 pool 3-85 17mers 0.4 ug/mL | 1.90 | 1.13 | 1.07 | 3.92 | 0.90 | 0.96 | 1.16 | 0.96 |

T1D Autoantigen Peptide-Specific Responses:

Each of the 440 individual T1D autoantigen-derived 17mer peptides (20 μg/mL) were incubated in a single well with whole blood collected 6-days after commencing oral gluten challenge. The preproinsulin derived peptide data are provided in Table 7A and B. Amongst the 34 preproinsulin-derived peptides, one elicited IP-10 responses in all four subjects that were 2-fold greater than to medium alone. The 17mer was derived from the preproinsulin signal sequence (PLLALLALWGPDPAAAF, SEQ ID NO: 45) and overlapped a further 17mer that was recognized more weakly by three subjects (MRLLPLLALLALWGPDP, SEQ ID NO: 47). A further 17mer (MALWMRLLPLLALLALW, SEQ ID NO: 54) with an overlap sequence corresponding to PLLAL-LALW (SEQ ID NO: 105) also stimulated IP-10 release in the strongest responder to CGSHLVEALYLVCGERG (SEQ ID NO: 53). Together these findings indicate that T1D patients frequently possess T cells specific for the overlapping sequence (PLLALLALWGPDP, SEQ ID NO: 1) which may harbor one or more MHC-Class II epitopes. Three other regions in preproinsulin were also immunogenic: (1) the peptide FYTPKTRREAEDLQGSL (SEQ ID NO: 46) stimulated elevated IP-10 release in three subjects, and in one of these subjects IL-2 and IFN-γ release was also increased. Overlapping sequences were also immunogenic, supporting importance of the sequence PKTRREAEVGQ (SEQ ID NO: 2) and RREAEDLEGSL (SEQ ID NO: 4), (2) REAE-DLQVGQVELGGGP (SEQ ID NO: 48) and in particular the overlap sequence DLQVGQVELGGGP (SEQ ID NO: 5), and (3) IP-10 release was pronounced in one subject who was HLA-DR3+DR4− and HLADQ2.5+DQ8− to NQHL-CGSHLVEALYLVC (SEQ ID NO: 51) and more weakly to an overlapping peptide CGSHLVEALYLVCGERG (SEQ ID NO: 53) that sharing the sequence CGSHLVEALYLVC (SEQ ID NO: 7), suggesting epitope/s are harbored in this sequence. Since the preproinsulin pool consisted of only 34 peptides and consistently stimulated strong IP-10 release and IFN-γ ELISpot responses, these findings suggest epitopes in preproinsulin, especially in the signal sequence including the sequence PLLALLALW (SEQ ID NO: 105) frequently play an important role in the immune-pathogenesis of T1D.

TABLE 7A

Preproinsulin peptides stimulating >2-fold increase in whole blood IP-10, IL-2 or IFN-g release

| | | Subject | | | |
|---|---|---|---|---|---|
| | | 1 | 7 | 6 | 2 |
| | | HLA-DR | | | |
| | | 3, 4 | 3, 4 | 3 | 3, 4 |
| | | HLA-DQ | | | |
| SEQ ID NO: | Amino acid sequence | 2.5, 8 | 2.5, 8 | 2.5 | 2.5, 8 |
| | | IP-10 fold-change | | | |
| 45 | PLLALLALWGPDPAAAF | 3.27 | 2.73 | 31.61 | 6.60 |
| 46 | FYTPKTRREAEDLQGSL | 1.06 | 2.70 | 2.24 | 4.64 |
| 47 | MRLLPLLALLALWGPDP | 2.07 | 2.18 | 7.26 | 1.37 |
| 48 | REAEDLQVGQVELGGGP | 2.00 | 2.48 | 1.13 | 1.67 |
| 49 | RREAEDLEGSLQPLALE | 1.36 | 0.99 | 3.15 | 2.58 |
| 50 | EDLQVGEVELGGGPGAG | 1.14 | 1.61 | 0.87 | 0.96 |
| 51 | NQHLCGSHLVEALYLVC | 0.95 | 1.57 | 75.09 | 1.45 |
| 52 | PKTRREAEVGQVELGGG | 1.08 | 0.97 | 3.69 | 1.56 |
| 53 | CGSHLVEALYLVCGERG | 1.13 | 0.83 | 3.30 | 1.50 |
| 54 | MALWMRLLPLLALLALW | 1.04 | 0.73 | 2.20 | 1.05 |
| 55 | YTPKTRREAEDLQVGQV | 1.06 | 1.42 | 1.56 | 1.22 |
| 56 | EAEVGQVELGGGPGAGS | 0.96 | 1.43 | 0.91 | 1.05 |
| 57 | RGFFYTPKTRREAEVGE | 0.92 | 0.75 | 0.90 | 0.91 |
| 58 | PLALEGSLQKRGIVEQC | 1.23 | 1.09 | 0.87 | 1.02 |
| | | IL-2 fold-change | | | |
| 45 | PLLALLALWGPDPAAAF | 1.00 | 3.77 | 1.64 | 1.00 |
| 46 | FYTPKTRREAEDLQGSL | 1.00 | 8.19 | 1.16 | 1.00 |
| 47 | MRLLPLLALLALWGPDP | 1.00 | 0.36 | 1.00 | 1.00 |
| 48 | REAEDLQVGQVELGGGP | 1.00 | 0.50 | 1.12 | 1.00 |
| 49 | RREAEDLEGSLQPLALE | 1.00 | 0.42 | 1.08 | 1.00 |
| 50 | EDLQVGEVELGGGPGAG | 1.00 | 7.35 | 1.00 | 1.00 |
| 51 | NQHLCGSHLVEALYLVC | 1.00 | 0.21 | 1.00 | 1.00 |
| 52 | PKTRREAEVGQVELGGG | 1.00 | 0.21 | 1.00 | 1.00 |
| 53 | CGSHLVEALYLVCGERG | 1.00 | 0.56 | 1.08 | 1.00 |
| 54 | MALWMRLLPLLALLALW | 1.00 | 0.21 | 1.00 | 1.00 |

TABLE 7A-continued

Preproinsulin peptides stimulating >2-fold increase in whole blood IP-10, IL-2 or IFN-g release

| | | Subject | | | |
|---|---|---|---|---|---|
| | | 1 | 7 | 6 | 2 |
| | | HLA-DR | | | |
| | | 3, 4 | 3, 4 | 3 | 3, 4 |
| | | HLA-DQ | | | |
| SEQ ID NO: | Amino acid sequence | 2.5, 8 | 2.5, 8 | 2.5 | 2.5, 8 |
| 55 | YTPKTRREAEDLQVGQV | 1.00 | 8.00 | 1.04 | 1.00 |
| 56 | EAEVGQVELGGGPGAGS | 1.00 | 4.83 | 1.00 | 1.00 |
| 57 | RGFFYTPKTRREAEVGE | 1.00 | 2.59 | 1.00 | 1.00 |
| 58 | PLALEGSLQKRGIVEQC | 1.00 | 3.50 | 1.00 | 1.00 |
| | | IFN-g fold-change | | | |
| 45 | PLLALLALWGPDPAAAF | 0.78 | 1.55 | 1.11 | 1.53 |
| 46 | FYTPKTRREAEDLQGSL | 0.92 | 2.02 | 1.15 | 1.47 |
| 47 | MRLLPLLALLALWGPDP | 1.02 | 0.53 | 0.91 | 0.85 |
| 48 | REAEDLQVGQVELGGGP | 0.75 | 0.67 | 1.07 | 0.88 |
| 49 | RREAEDLEGSLQPLALE | 0.99 | 0.77 | 1.00 | 1.27 |
| 50 | EDLQVGEVELGGGPGAG | 0.93 | 2.06 | 0.71 | 1.01 |
| 51 | NQHLCGSHLVEALYLVC | 0.91 | 0.53 | 1.66 | 0.82 |
| 52 | PKTRREAEVGQVELGGG | 1.07 | 0.52 | 0.81 | 1.08 |
| 53 | CGSHLVEALYLVCGERG | 0.99 | 0.69 | 0.74 | 1.01 |
| 54 | MALWMRLLPLLALLALW | 1.02 | 0.67 | 0.88 | 1.01 |
| 55 | YTPKTRREAEDLQVGQV | 0.51 | 1.86 | 1.00 | 0.82 |
| 56 | EAEVGQVELGGGPGAGS | 1.07 | 1.55 | 0.97 | 0.82 |
| 57 | RGFFYTPKTRREAEVGE | 1.06 | 1.09 | 1.06 | 0.82 |
| 58 | PLALEGSLQKRGIVEQC | 0.43 | 1.53 | 0.86 | 0.82 |

TABLE 7B

Alignment of preproinsulin peptides stimulating
>2-fold increase in whole blood IP-10,
IL-2 or IFN-g release

| | | Subject | | | |
|---|---|---|---|---|---|
| | | 1 | 7 | 6 | 2 |
| | | HLA-DR | | | |
| | | 3, 4 | 3, 4 | 3 | 3, 4 |
| | | HLA-DQ | | | |
| SEQ ID NO: | Amino acid sequence | 2.5, 8 | 2.5, 8 | 2.5 | 2.5, 8 |
| | | IP-10 fold-change | | | |
| 45 | PLLALLALWGPDPAAAF | 3.27 | 2.73 | 31.61 | 6.60 |
| 47 | MRLLPLLALLALWGPDP | 2.07 | 2.18 | 7.26 | 1.37 |
| 54 | MALWMRLLPLLALLALW | 1.04 | 0.73 | 2.20 | 1.05 |
| 57 | RGFFYTPKTRREAEVGE | 0.92 | 0.75 | 0.90 | 0.91 |
| 52 | PKTRREAEVGQVELGGG | 1.08 | 0.97 | 3.69 | 1.56 |
| 46 | FYTPKTRREAEDLQGSL | 1.06 | 2.70 | 2.24 | 4.64 |
| 55 | YTPKTRREAEDLQVGQV | 1.06 | 1.42 | 1.56 | 1.22 |
| 49 | RREAEDLEGSLQPLALE | 1.36 | 0.99 | 3.15 | 2.58 |
| 56 | EAEVGQVELGGGPGAGS | 0.96 | 1.43 | 0.91 | 1.05 |
| 48 | REAEDLQVGQVELGGGP | 2.00 | 2.48 | 1.13 | 1.67 |
| 50 | EDLQVGEVELGGGPGAG | 1.14 | 1.61 | 0.87 | 0.96 |
| 58 | PLALEGSLQKRGIVEQC | 1.23 | 1.09 | 0.87 | 1.02 |
| 51 | NQHLCGSHLVEALYLVC | 0.95 | 1.57 | 75.09 | 1.45 |
| 53 | CGSHLVEALYLVCGERG | 1.13 | 0.83 | 3.30 | 1.50 |
| | | IL-2 fold-change | | | |
| 45 | PLLALLALWGPDPAAAF | 1.00 | 3.77 | 1.64 | 1.00 |
| 47 | MRLLPLLALLALWGPDP | 1.00 | 0.36 | 1.00 | 1.00 |
| 54 | MALWMRLLPLLALLALW | 1.00 | 0.21 | 1.00 | 1.00 |
| 57 | RGFFYTPKTRREAEVGE | 1.00 | 2.59 | 1.00 | 1.00 |
| 52 | PKTRREAEVGQVELGGG | 1.00 | 0.21 | 1.00 | 1.00 |
| 46 | FYTPKTRREAEDLQGSL | 1.00 | 8.19 | 1.16 | 1.00 |
| 55 | YTPKTRREAEDLQVGQV | 1.00 | 8.00 | 1.04 | 1.00 |
| 49 | RREAEDLEGSLQPLALE | 1.00 | 0.42 | 1.08 | 1.00 |
| 56 | EAEVGQVELGGGPGAGS | 1.00 | 4.83 | 1.00 | 1.00 |
| 48 | REAEDLQVGQVELGGGP | 1.00 | 0.50 | 1.12 | 1.00 |
| 50 | EDLQVGEVELGGGPGAG | 1.00 | 7.35 | 1.00 | 1.00 |
| 58 | PLALEGSLQKRGIVEQC | 1.00 | 3.50 | 1.00 | 1.00 |
| 51 | NQHLCGSHLVEALYLVC | 1.00 | 0.21 | 1.00 | 1.00 |
| 53 | CGSHLVEALYLVCGERG | 1.00 | 0.56 | 1.08 | 1.00 |
| | | IFN-g fold-change | | | |
| 45 | PLLALLALWGPDPAAAF | 0.78 | 1.55 | 1.11 | 1.53 |
| 47 | MRLLPLLALLALWGPDP | 1.02 | 0.53 | 0.91 | 0.85 |

TABLE 7B-continued

Alignment of preproinsulin peptides stimulating >2-fold increase in whole blood IP-10, IL-2 or IFN-g release

| | | Subject | | | |
|---|---|---|---|---|---|
| | | 1 | 7 | 6 | 2 |
| | | HLA-DR | | | |
| | | 3, 4 | 3, 4 | 3 | 3, 4 |
| | | HLA-DQ | | | |
| SEQ ID NO: | Amino acid sequence | 2.5, 8 | 2.5, 8 | 2.5 | 2.5, 8 |
| 54 | MALWMRLLPLLALLALW | 1.02 | 0.67 | 0.88 | 1.01 |
| 57 | RGFFYTPKTRREAEVGE | 1.06 | 1.09 | 1.06 | 0.82 |
| 52 | PKTRREAEVGQVELGGG | 1.07 | 0.52 | 0.81 | 1.08 |
| 46 | FYTPKTRREAEDLQGSL | 0.92 | 2.02 | 1.15 | 1.47 |
| 55 | YTPKTRREAEDLQVGQV | 0.51 | 1.86 | 1.00 | 0.82 |
| 49 | RREAEDLEGSLQPLALE | 0.99 | 0.77 | 1.00 | 1.27 |
| 56 | EAEVGQVELGGGPGAGS | 1.07 | 1.55 | 0.97 | 0.82 |
| 48 | REAEDLQVGQVELGGGP | 0.75 | 0.67 | 1.07 | 0.88 |
| 50 | EDLQVGEVELGGGPGAG | 0.93 | 2.06 | 0.71 | 1.01 |
| 58 | PLALEGSLQKRGIVEQC | 0.43 | 1.53 | 0.86 | 0.82 |
| 51 | NQHLCGSHLVEALYLVC | 0.91 | 0.53 | 1.66 | 0.82 |
| 53 | CGSHLVEALYLVCGERG | 0.99 | 0.69 | 0.74 | 1.01 |

Three 17mers in the 155-member GAD65 peptide library elicited increased IP-10 release in all four subjects: NMFTYEIAPVFVLLEYV (SEQ ID NO: 9), NVCFWYIPPSLRTLEDN (SEQ ID NO: 10), and FNQLSTGLDMVGLAADW (SEQ ID NO: 11) (Table 8). Three subjects showed elevated IP-10 release to two further sequences: RPTLAFLQDVMNILLQY (SEQ ID NO: 59) and KYKIWMHVDAAWGGGLL (SEQ ID NO: 60), and two subjects responded to the overlapping sequences: AFLQDVMNILLEYVVKS (SEQ ID NO: 63) and MNILLEYVVKSFDRSTK (SEQ ID NO: 64) indicating that the overlap sequence MNILLEYVVKS (SEQ ID NO: 8) harbored epitope(s) commonly recognized in T1D patients. One subjected responded to the peptide FDRSTKVIDFHYPNELL (SEQ ID NO: 61) with elevated IP-10, IL-2 and IFN-γ.

TABLE 8

GAD65 peptides stimulating >2-fold increase in whole blood IP-10, IL-2 or IFN-g release in 2 or more subjects

| | | Subject | | | |
|---|---|---|---|---|---|
| | | 1 | 7 | 6 | 2 |
| | | HLA-DR | | | |
| | | 3, 4 | 3, 4 | 3 | 3, 4 |
| | | HLA-DQ | | | |
| SEQ ID NO: | Amino acid sequence | 2.5, 8 | 2.5, 8 | 2.5 | 2.5, 8 |
| | | IP-10 fold-change | | | |
| 9 | NMFTYEIAPVFVLLEYV | 7.27 | 2.10 | 17.85 | 2.02 |
| 10 | NVCFWYIPPSLRTLEDN | 10.24 | 9.00 | 6.04 | 8.08 |
| 11 | FNQLSTGLDMVGLAADW | 23.55 | 15.66 | 57.27 | 5.90 |
| 59 | RPTLAFLQDVMNILLQY | 3.22 | 1.05 | 2.62 | 2.10 |
| 60 | KYKIWMHVDAAWGGGLL | 2.13 | 2.20 | 2.07 | 1.35 |
| 61 | FDRSTKVIDFHYPNELL | 1.38 | 2.11 | 1.15 | 1.14 |
| 62 | KTGIVSSKIIKLFFRLQ | 1.15 | 1.25 | 4.16 | 1.32 |
| 63 | AFLQDVMNILLEYVVKS | 3.00 | 1.74 | 2.83 | 1.06 |
| 64 | MNILLEYVVKSFDRSTK | 1.95 | 0.84 | 2.16 | 4.08 |
| | | IL-2 fold-change | | | |
| 9 | NMFTYEIAPVFVLLEYV | 1.00 | 0.81 | 2.43 | 1.00 |
| 10 | NVCFWYIPPSLRTLEDN | 1.00 | 3.40 | 1.49 | 1.00 |

TABLE 8-continued

GAD65 peptides stimulating >2-fold increase in whole blood IP-10, IL-2 or IFN-g release in 2 or more subjects

| SEQ ID NO: | Amino acid sequence | Subject 1 HLA-DR 3, 4 HLA-DQ 2.5, 8 | Subject 7 HLA-DR 3, 4 HLA-DQ 2.5, 8 | Subject 6 HLA-DR 3 HLA-DQ 2.5 | Subject 2 HLA-DR 3, 4 HLA-DQ 2.5, 8 |
|---|---|---|---|---|---|
| 11 | FNQLSTGLDMVGLAADW | 1.00 | 1.37 | 1.28 | 1.00 |
| 59 | RPTLAFLQDVMNILLQY | 1.00 | 0.58 | 1.54 | 1.00 |
| 60 | KYKIWMHVDAAWGGGLL | 1.00 | 0.87 | 1.80 | 1.00 |
| 61 | FDRSTKVIDFHYPNELL | 1.00 | 11.19 | 1.00 | 1.00 |
| 62 | KTGIVSSKIIKLFFRLQ | 1.00 | 10.36 | 1.00 | 1.00 |
| 63 | AFLQDVMNILLEYVVKS | 1.00 | 1.54 | 0.97 | 1.00 |
| 64 | MNILLEYVVKSFDRSTK | 1.00 | 0.36 | 0.85 | 1.00 |
| IFN-g fold-change | | | | | |
| 9 | NMFTYEIAPVFVLLEYV | 0.76 | 0.83 | 0.83 | 1.49 |
| 10 | NVCFWYIPPSLRTLEDN | 0.78 | 1.58 | 1.42 | 0.66 |
| 11 | FNQLSTGLDMVGLAADW | 0.94 | 1.05 | 0.81 | 1.15 |
| 59 | RPTLAFLQDVMNILLQY | 0.84 | 0.76 | 0.71 | 1.32 |
| 60 | KYKIWMHVDAAWGGGLL | 0.69 | 0.75 | 1.24 | 0.93 |
| 61 | FDRSTKVIDFHYPNELL | 0.36 | 2.47 | 0.84 | 0.67 |
| 62 | KTGIVSSKIIKLFFRLQ | 0.55 | 2.45 | 1.11 | 0.67 |
| 63 | AFLQDVMNILLEYVVKS | 0.97 | 0.93 | 1.00 | 0.62 |
| 64 | MNILLEYVVKSFDRSTK | 0.90 | 0.57 | 0.90 | 1.49 |

One peptide amongst the 255 17mers in the IA-2 library consistently stimulated IP-10 and IL-2 release, and in two subjects also stimulated IFN-γ release, suggesting that it is the immune-dominant peptide in IA-2 (GRTGTYILIDMV-LNRMA (SEQ ID NO: 12), Table 9). A second peptide, PKAARPPVTPVLLEKKS (SEQ ID NO: 13), evoked IP-10 but not IL-2 or IFN-γ release in all four subjects. Three subjects showed IP-10 release in response to the peptide CTVIVMLTPLVEDGVKQ (SEQ ID NO: 66). Two subjects each responded with IP-10 release to the two peptides: AHSTSPMRSVLLTLVAL (SEQ ID NO: 70) and SPLQAELLPPLLEHLLL (SEQ ID NO: 71). Only Subject 7 responded to three peptides: WESGCTVIVMLTPLVED (SEQ ID NO: 67), SSEVQQVPSPVSSEPPK (SEQ ID NO: 68), and NVGADIKKTMEGPVEGR (SEQ ID NO: 69), but IP-10, IL-2 and IFN-γ release were each elevated.

TABLE 9

IA-2 peptides stimulating >2-fold increase in whole blood IP-10, IL-2 or IFN-g release in 2 or more subjects

| SEQ ID NO: | Amino acid sequence | Subject 1 HLA-DR 3, 4 HLA-DQ 2.5, 8 | Subject 7 HLA-DR 3, 4 HLA-DQ 2.5, 8 | Subject 6 HLA-DR 3 HLA-DQ 2.5 | Subject 2 HLA-DR 3, 4 HLA-DQ 2.5, 8 |
|---|---|---|---|---|---|
| IP-10 fold-change | | | | | |
| 12 | GRTGTYILIDMVLNRMA | 5.74 | 19.82 | 56.20 | 19.96 |
| 13 | PKAARPPVTPVLLEKKS | 31.41 | 17.78 | 38.82 | 34.34 |
| 65 | LAEHVHMSSGSFINISV | 1.27 | 2.28 | 1.28 | 8.79 |
| 66 | CTVIVMLTPLVEDGVKQ | 3.57 | 2.08 | 2.80 | 1.49 |
| 67 | WESGCTVIVMLTPLVED | 1.32 | 2.14 | 1.91 | 1.56 |
| 68 | SSEVQQVPSPVSSEPPK | 1.36 | 2.06 | 1.03 | 0.90 |
| 69 | NVGADIKKTMEGPVEGR | 1.64 | 2.20 | 0.96 | 1.33 |
| 70 | AHSTSPMRSVLLTLVAL | 1.97 | 3.09 | 2.16 | 1.19 |
| 71 | SPLQAELLPPLLEHLLL | 4.23 | 14.74 | 0.80 | 1.09 |
| IL-2 fold-change | | | | | |
| 12 | GRTGTYILIDMVLNRMA | 5.51 | 11.23 | 14.18 | 6.83 |
| 13 | PKAARPPVTPVLLEKKS | 1.00 | 0.47 | 1.00 | 1.00 |
| 65 | LAEHVHMSSGSFINISV | 1.00 | 2.57 | 1.15 | 1.00 |
| 66 | CTVIVMLTPLVEDGVKQ | 1.00 | 1.98 | 1.00 | 1.00 |
| 67 | WESGCTVIVMLTPLVED | 1.00 | 7.17 | 1.00 | 1.00 |
| 68 | SSEVQQVPSPVSSEPPK | 1.00 | 6.44 | 1.00 | 1.00 |
| 69 | NVGADIKKTMEGPVEGR | 1.00 | 5.65 | 1.06 | 1.00 |
| 70 | AHSTSPMRSVLLTLVAL | 1.00 | 4.78 | 1.00 | 1.00 |
| 71 | SPLQAELLPPLLEHLLL | 1.00 | 0.68 | 1.00 | 1.00 |
| IFN-g fold-change | | | | | |
| 12 | GRTGTYILIDMVLNRMA | 0.92 | 1.65 | 2.11 | 4.99 |
| 13 | PKAARPPVTPVLLEKKS | 0.67 | 0.66 | 0.95 | 4.15 |
| 65 | LAEHVHMSSGSFINISV | 0.40 | 1.12 | 1.25 | 2.03 |
| 66 | CTVIVMLTPLVEDGVKQ | 1.08 | 1.07 | 0.93 | 0.76 |
| 67 | WESGCTVIVMLTPLVED | 1.01 | 2.18 | 0.87 | 0.82 |
| 68 | SSEVQQVPSPVSSEPPK | 1.06 | 2.11 | 0.97 | 0.73 |
| 69 | NVGADIKKTMEGPVEGR | 0.94 | 2.16 | 0.98 | 1.12 |
| 70 | AHSTSPMRSVLLTLVAL | 1.01 | 1.84 | 0.84 | 0.94 |
| 71 | SPLQAELLPPLLEHLLL | 0.90 | 0.98 | 0.92 | 1.05 |

Conclusions

Oral gluten challenge does not enhance whole blood cytokine release in response to T1D autoantigen-derived peptides, as it does to gluten-derived peptides in Celiac disease. However, IP-10 and IL-2 both offer greater sensitivity than IFN-γ in whole blood cytokine release assays for gluten-reactive T cells in Celiac disease, and when applied to screening peptides derived from T1D autoantigens in patients with T1D and Celiac disease, identify amino acid sequences that are consistently immune-dominant. One 17mer peptide from preproinsulin, three from GAD65 and two from IA-2 stimulated elevated whole blood IP-10 release in four of four T1D subjects. Several other sequences commonly but less consistently and less potently stimulated IP-10 release in the T1D subjects assessed in this study. Hence, application of multiplex cytokine and chemokine measurement to epitope mapping in T1D reveals a hierarchy of epitopes not previously evident in the classical T1D-associated autoantigens preproinsulin, GAD65 and IA-2.

Example 2. Gluten Immunity and Islet Autoimmunity in Type-1 Diabetes

The objective of this study was to quantify and compare T cell responses to pancreatic islet autoantigens, immunodominant gluten peptides, and pathogen-derived recall antigens before and after oral gluten challenge in patients with both Type-1 diabetes (T1D) and celiac disease. CD4+ and CD8+ T cell depletions of whole blood samples were performed in order to determine the specific cell population of the T cell cytokine responses to the T1D peptide antigens being analyzed.

Depletion of human CD4+ and CD8+ T cells directly from whole blood, using CD4 and CD8 Dynabeads respectively (Dynabeads Human CD4, Life Technologies, #11145D; Dynabeads Human CD8, Life Technologies, #11145D), was done according to the manufacturer's protocol. Briefly, the Dynabeads were resuspended and the desired volume was transferred to a 15 Ml tube. The calculation of the volume of beads added to whole blood was $2\times10^6$ CD4 beads (25 μL) and $4\times10^6$ CD8 beads (50 μL) per Ml of whole blood. The beads were first washed with 3 Ml PBS, vortexed and placed on the magnet for 1 minute. Supernatant was discarded and beads were removed from the magnet. Whole blood was then added to the beads at the volume calculated for the concentration of beads in the tubes. The tubes containing whole blood and Dynabeads were then incubated 45 minutes at 4° C. on a continuous rocker.

Tubes were then placed into the magnet for 2 minutes. The whole blood supernatant was then transferred to a new tube for use in 24-hour Whole Blood Assay or for Flow Cytometric Analysis. Magnetic beads were discarded.

PBMC from whole blood, CD4+ T cell depleted, and CD8+ T cell depleted blood was first purified by ficoll density gradient centrifugation. Ficoll-Paque (15 Ml) was added to bottom chamber of the Sepmate tubes. Whole blood (6 Ml) or depleted blood (4 Ml) was diluted with an equal volume of D-PBS+2% FBS and layered on top of the ficoll cushion. Tubes were then centrifuged in a swinging bucket rotor at 500×g for 10 minutes at room temperature. The top layer was then transferred to a new 50 Ml tube and cells were washed by adjusting the total volume to 50 Ml with D-PBS+2% FBS. Cells were centrifuged at 300×g for 10 minutes at room temperature. Supernatant was discarded and depleted cells were resuspended in 2 Ml D-PBS+2% FBS. Cells from whole blood were resuspended in 6 Ml D-PBS+2% FBS. Cells were transferred to 1.0 Ml microcentrifuge snap cap tubes (1 Ml/tube) and centrifuged at 300×g for 5 minutes at room temperature. Supernatant was discarded and cells were resuspended in 100μ D-PBS+2% FBS. Fluorochrome labelled antibodies (10 μg/Ml) were added to each tube accordingly (Table 10).

TABLE 10

Flow Cytometry Antibodies for T Cell Phenotypic Analysis

| Cells | Antibody |
| --- | --- |
| Whole Blood PBMC Tube 1 | none |
| Whole Blood PBMC Tube 2 | Anti-CD3-FITC |
| Whole Blood PBMC Tube 3 | Anti-CD4-Pac Blue |
| Whole Blood PBMC Tube 4 | Anti-CD8-PE |
| Whole Blood PBMC Tube 5 | Anti-CD19-APC |
| Whole Blood PBMC Tube 6 | Anti-CD3-FITC, CD4-PacBlue, CD8-PE, CD19-APC |
| CD4 Depleted PBMC Tube 1 | none |
| CD4 Depleted PBMC Tube 2 | Anti-CD3-FITC, CD4-PacBlue, CD8-PE, CD19-APC |
| CD8 Depleted PBMC Tube 1 | none |
| CD8 Depleted PBMC Tube 2 | Anti-CD3-FITC, CD4-PacBlue, CD8-PE, CD19-APC |

Cells were incubated at 4° C. for 45 minutes in the dark. Volume was adjusted to 1 Ml with D-PBS+2% FBS and cells were centrifuged at 300×g for 5 minutes at room temperature. Supernatants were discarded and cells were resuspended in 100 μL D-PBS+2% FBS. Cells were analyzed with data being collected on an Amnis FlowCyte flow cytometer. Fluorescent compensation adjustments were made using single antibody stained cells from whole blood (Tubes 2-5; Table 10). Analysis was performed using the Amnis Ideas Application.

Whole blood samples from subjects were processed for CD4+ and CD8+ T cell depletions using Dynabeads magnetic beads (Table 11).

TABLE 11

| Subject | MHC | | | | | |
| --- | --- | --- | --- | --- | --- | --- |
| | Drb1-a | Dqa1-a | Dqb1-a | Drb1-b | Dqa1-b | Dqb1-b |
| T1D 1 | 0301 | 0501 | 0201 | 0401 | 0301 | 0302 |
| T1D 2 | 0301 | 0501 | 0201 | 0401 | 0303 | 0302 |
| T1D 3 | 0301 | 0501 | 0201 | 0401 | 0301 | 0302 |
| T1D 4 | 0301 | 0501 | 0201 | 0402 | 0301 | 0302 |
| T1D 5 | 0301 | | 0201 | 0401 | | 0302 |
| T1D 6 | 0301 | | 0201 | 0401 | | 0302 |
| Healthy Control 1 | 0402 | 0301 | 0302 | 1501 | 0102 | 0602 |
| Healthy Control 2 | 0301 | 0501 | 0201 | 1302 | 0102 | 0604 |
| Healthy Control 3 | 0801 | 0401 | 0402 | 1501 | 0102 | 0602 |
| Healthy Control 4 | 0102 | 0101 | 0501 | 0404 | 0301 | 0302 |

Flow cytometric analysis of the depleted samples indicated that the depletion of CD4+ and CD8+ T cells was nearly complete (Table 12). Analysis was done on CD3+ T cells residing in the live lymphocyte population (gate R1). The percentage of CD3+/CD4+ T cells in the normal PBMC population ranged from 56.9%-66.9% for the six subjects. The percentage of CD3+/CD8+ T cells in the live lymphocyte gate of PBMC was 28.2%-34-9%. With the removal of cells by magnetic bead isolation, the percentage of CD3+/CD4+ T cells dropped to 0.04%-0.5%. Detection of CD3+/CD8+ T cells in the depleted samples ranged from 0%-1.29%.

TABLE 12

| | % Cells Determined by Flow Cytometry Analysis | | | |
|---|---|---|---|---|
| Subject | % CD3+/CD4+ T Cells | | % CD3+/CD8+ T Cells | |
| ID # | PBMC | Depleted PBMC | PBMC | Depleted PBMC |
| T1D 1 | 60.50 | 0.27 | 30.20 | 0.01 |
| T1D 2 | 59.40 | 0.27 | 31.20 | 0.10 |
| T1D 3 | 57.90 | 0.19 | 30.80 | 1.29 |
| T1D 4 | 56.90 | 0.50 | 34.90 | 0.00 |
| T1D 5 | 66.90 | 0.04 | 28.30 | 0.02 |
| T1D 6 | 63.70 | 0.09 | 28.20 | 0.03 |

In all subjects, nearly complete depletion of CD4+ and CD8+ T cells occurred with >99% CD4+ T cell depletion and >98% CD8+ T cell depletion.

The depleted blood as well as the remaining undepleted whole blood was then utilized in whole blood cytokine release assays. T-cell cytokine responses were assessed for reactivity to pools of 17mer peptides encompassing all unique 12mer amino-acid sequences derived from pancreatic islet antigens commonly recognized by autoantibodies in T1D: insulin, glutamic decarboxylase-65 (GAD65), and insulinoma-associated antigen (IA)-2 as provided in Table 13A and Table 13B.

TABLE 13A

| Peptide | Concentration |
|---|---|
| 20150-01, | 20 ug/Ml |
| 20150-05-W1 | 20 ug/Ml |
| 20150-11-W1 | 20 ug/Ml |
| 20150-15, | 20 ug/Ml |
| 20150-19, | 20 ug/Ml |
| 20150-24, | 20 ug/Ml |
| L2P1, 049, | 20 ug/Ml |
| L2P1, 051, | 20 ug/Ml |
| L2P2, 065, | 20 ug/Ml |
| L3P1, 007, | 20 ug/Ml |
| L3P1, 046, | 20 ug/Ml |
| L3P2, 076, | 20 ug/Ml |
| L1P1, ProIns POOL | 4 ug/Ml |
| L2P1, GAD65 POOL | 4 ug/Ml |
| L2P2, GAD65 POOL | 4 ug/Ml |
| L3P1, IA2 POOL | 4 ug/Ml |
| L3P2, IA2 POOL | 4 ug/Ml |
| L3P3, IA2 POOL | 4 ug/Ml |
| NEX-01 | 25 Um |
| Nexgen POOL | 25 Um |
| CEFT | 1 ug/Ml |

TABLE 13B

| Peptide | Concentration | Sequence | SEQ ID NO: |
|---|---|---|---|
| 20150-01, | 20 ug/mL | FYTPKTRREAEDLQGSL | 46 |
| 20150-05-W1 | 20 ug/mL | REAEDLQVGQVELGGGP | 48 |
| 20150-11-W1 | 20 ug/mL | NQHLCGSHLVEALYLVC | 51 |
| 20150-15 | 20 ug/mL | LQGSLQPLALEGSLQKR | 72 |
| 20150-19 | 20 ug/mL | EDLQVGQVELGGGPGAG | 73 |
| 20150-24 | 20 ug/mL | PLLALLALWGPDPAAAF | 45 |
| L2P1, 049 | 20 ug/mL | H-FNQLSTGLDMVGLAADW-OH | 11 |
| L2P1, 051, | 20 ug/mL | H-NMFTYEIAPVFVLLEYV-OH | 9 |
| L2P2, 065, | 20 ug/mL | H-NVCFWYIPPSLRTLEDN-OH | 10 |
| L3P1, 007, | 20 ug/mL | H-SPLQAELLPPLLEHLLL-OH | 71 |
| L3P1, 046, | 20 ug/mL | H-PKAARPPVTPVLLEKKS-OH | 13 |
| L3P2, 076, | 20 ug/mL | H-GRTGTYILIDMVLNRMA-OH | 12 |
| L1P1, ProIns POOL | 4 ug/mL | | |
| L2P1, GAD65 POOL | 4 ug/mL | | |
| L2P2, GAD65 POOL | 4 ug/mL | | |
| L3P1, IA2 POOL | 4 ug/mL | | |
| L3P2, IA2 POOL | 4 ug/mL | | |
| L3P3, IA2 POOL | 4 ug/mL | | |
| NEX-01 | 25 uM | ZLQPFPCIPELPYPQP-NH2 | 74 |
| Nexgen POOL | 25 uM | | |
| CEFT | 1 ug/mL | | |

Fresh heparinized blood was incubated with peptide. Concentrations of individual islet-autoantigen peptides were 20 μg/mL and constituent peptides in islet-autoantigen pools were 4 ug/mL. Control MHC class II peptide mix CEFT was used at 1 μg/mL. Gliadin peptide pools were added to whole blood assays at 25 μM. Whole blood assays were incubated for 24 h at 37° C. in 5% CO2. Plasma was separated from blood after centrifugation at 500×g for 10 minutes at room temperature and then transferred to a corresponding well in a "mirror image" sterile 96-well plate. and frozen at −80° C. until use. Multiplex bead-based cytokine assays (MAGPix) were performed according to manufacturer's instructions on thawed plasma. Concentrations of interferon (IFN)-γ-induced protein-10 (IP-10), interleukin (IL)-2 and IFN-γ. Table 14 is a summary of the results for the whole blood cytokine assays which expresses the data in the number of subjects that are positive for ≥1.25 fold production of cytokine over cells incubated with medium only (background).

TABLE 14

| | Fold Change | | | | | | | | | Fold Change | | |
|---|---|---|---|---|---|---|---|---|---|---|---|---|
| T1D | Undepleted WB | | | CD4- Depleted | | | CD8- Depleted | | | Healthy | | |
| Subjects Peptide | IFNg | IL-2 | IP-10 | IFNg | IL-2 | IP-10 | IFNg | IL-2 | IP-10 | Subjects Peptide | IFNg | IL-2 | IP-10 |
| Medium [0.1%DMSO] | | | | | | | | | | Medium [0.1%DMSO] | | | |

TABLE 14-continued

| T1D Subjects Peptide | Undepleted WB IFNg | IL-2 | IP-10 | CD4-Depleted IFNg | IL-2 | IP-10 | CD8-Depleted IFNg | IL-2 | IP-10 | Healthy Subjects Peptide | Fold Change IFNg | IL-2 | IP-10 |
|---|---|---|---|---|---|---|---|---|---|---|---|---|---|
| 20150-01, 20 ug/mL | | | 4/6 | | | | | | 1/6 | 20150-01, 20 ug/mL | | | 2/4 |
| 20150-05-W1, 20 ug/mL | | | 4/6 | 1/6 | | 3/6 | 1/6 | 1/6 | 5/6 | 20150-05-W1, 20 ug/mL | | | 3/4 |
| 20150-11-W1, 20 ug/mL | | 1/6 | 2/6 | 1/6 | | | 1/6 | | 2/6 | 20150-11-W1, 20 ug/mL | | | 2/4 |
| 20150-15, 20 ug/mL | | | 1/6 | | | | 2/6 | 1/6 | | 20150-15, 20 ug/mL | | | |
| 20150-19, 20 ug/mL | | | 2/6 | | | | 3/6 | 1/6 | | 20150-19, 20 ug/mL | 1/4 | | 1/4 |
| 20150-24, 20 ug/mL | 4/6 | 4/6 | 6/6 | 1/6 | | 3/6 | 5/6 | 6/6 | 5/6 | 20150-24, 20 ug/mL | 1/4 | 1/4 | 4/4 |
| L2P1, 049, 20 ug/mL | | | 1/6 | | | 2/6 | | | 2/6 | L2P1, 049, 20 ug/mL | | | |
| L2P1, 051, 20 ug/mL | | 1/6 | 4/6 | 1/6 | | 3/6 | 2/6 | 2/6 | 5/6 | L2P1, 051, 20 ug/mL | | | 3/4 |
| L2P2, 065, 20 ug/mL | | | | | | | | | | L2P2, 065, 20 ug/mL | | | |
| L3P1, 007, 20 ug/mL | | | 1/6 | | | | | 1/6 | | L3P1, 007, 20 ug/mL | | | 2/4 |
| L3P1, 046, 20 ug/mL | | 1/6 | | | | | | | 2/6 | L3P1, 046, 20 ug/mL | | | 1/4 |
| L3P2, 076, 20 ug/mL | 4/6 | 5/6 | 6/6 | | | 3/6 | 5/6 | 6/6 | 5/6 | L3P2, 076, 20 ug/mL | 1/4 | 1/4 | 3/4 |
| NEX-01, 25 uM | | | | | | 1/6 | | | 1/6 | NEX-01, 25uM | | | 1/4 |
| L1P1, ProIns POOL, 4 ug/mL | 4/6 | 5/6 | 6/6 | 3/6 | | 2/6 | 6/6 | 6/6 | 5/6 | L1P1, ProIns POOL, 4 ug/mL | 2/4 | 1/4 | 4/4 |
| L2P1, GAD65 POOL, 4 ug/mL | 2/6 | 2/6 | 6/6 | 2/6 | | 1/6 | 5/6 | 6/6 | 3/6 | L2P1, GAD65 POOL, 4 ug/mL | 2/4 | 1/4 | 4/4 |
| L2P2, GAD65 POOL, 4 ug/mL | 2/6 | 4/6 | 6/6 | | | 1/6 | 5/6 | 5/6 | 4/6 | L2P2, GAD65 POOL, 4 ug/mL | 1/4 | 1/4 | 3/4 |
| L3P1, IA2 POOL, 4 ug/mL | 1/6 | 2/6 | 4/6 | | | 1/6 | 4/6 | 5/6 | 3/6 | L3P1, IA2 POOL, 4 ug/mL | 2/4 | 2/4 | 4/4 |
| L3P2, IA2 POOL, 4 ug/mL | 4/6 | 5/6 | 6/6 | 1/6 | | | 6/6 | 6/6 | 3/6 | L3P2, IA2 POOL, 4 ug/mL | 1/4 | 1/4 | 3/4 |
| L3P3, IA2 POOL, 4 ug/mL | | 2/6 | 6/6 | 1/6 | | 1/6 | 4/6 | 3/6 | 3/6 | L3P3, IA2 POOL, 4 ug/mL | 1/4 | | 4/4 |
| Nexgen POOL, 25 uM | | 1/6 | 6/6 | | | 2/6 | 2/6 | 2/6 | 5/6 | Nexgen POOL, 25 uM | | | 4/4 |
| CEFT 1 ug/mL [0.1% DMSO] | 3/6 | 3/6 | 6/6 | 2/6 | | 3/6 | 5/6 | 5/6 | 5/6 | CEFT 1 ug/mL [0.1% DMSO] | 2/4 | 2/4 | 4/4 |

=>50% of Subjects with >1.25 Fold Change in Cytokine over Background

T1D

The six T1D subjects showed a clear reactivity to the peptides being analyzed with a cytokine fold change over background greater than 1.25 (Table 14). The majority of the responses were seen with production of IP-10 in at least 1 subject for 15 of the 21 peptides and control peptides tested. Greater than 50% of the subjects tested showed significant IP-10 responses to 20150-01, 20150-05-W1, 20150-24, L2P1-051, L3P2-076, L1P1-Proinsulin Pool, L2P1-GAD65 Pool, L2P2-GAD65 Pool, L3P1-IA2 Pool, L3P2-IA2 Pool, L3P3-IA2 Pool and the Nexgen Pool and CEFT controls.

Greater the 50% of the subjects tested showed significant IFNg and IL-2 responses as well. These responses include peptides 20150-24, L3P2-076, L1P1-Proinsulin Pool, L2P2-GAD65 Pool, and L3P2-IA2 Pool.

Healthy Subjects

Comparing these responses to normal healthy subjects, there was a significant decrease in IFNg and IL-2 responses. There were no peptides with >50% of the healthy subjects exhibiting a >1.25 fold IFNg or IL-2 response. A slight increase was seen from 15 reactive peptides in at least 1 T1D subject to 18 reactive peptides in at least 1 healthy subject.

Overall there were 13 reactive peptides that were stimulatory for >50% of the T1D subjects and 12 reactive peptides that were stimulatory for >50% of the healthy subjects.

CD4+ T Cell Depleted PBMC

When CD4+ T cells were depleted from PBMC and then tested under the same conditions, all cytokine fold change responses were diminished. The IL-2 responses are completely eliminated for all T1D subjects and for all peptides tested. Although the IFNg responses were slightly increased in the number of reactive peptides, overall there were no peptides that stimulated a >1.25 fold IFNg response in >50% of the T1D subjects tested compared to PBMC. A slight decrease was observed in the number of reactive peptides (12 peptides instead of 15) eliciting an IP-10 response. Additionally, there were no peptides that stimulated IP-10 responses in >50% of the subjects tested compared to PBMC. The CD4+ T cell depletion did result in higher background levels (medium only) for IP-10.

CD8+ T Cell Depleted PBMC

PBMC depleted of CD8+ T cells exhibited increased cytokine production for IFNg, IL-2, but slightly decreased IP-10 responses.

IFNg responses with >1.25 fold change were observed in both the number of peptides that were stimulatory, but also in the number of subjects that were exhibiting that >1.25 fold change. Out of 21 peptides tested, 16 peptides stimulated IFNg production compared to 8 peptides for whole PBMC. A significant IFNg fold change was seen in >50% of the T1D subjects with 9 peptides compared to 4 peptides for whole PBMC.

Analysis of IL-2 production showed similar results. Out of 21 peptides tested, 16 peptides stimulated IL-2 production compared to 12 peptides for whole PBMC. Again, a significant IL-2 fold change was seen in >50% of the T1D subjects with reactivity to 8 peptides compared to 5 peptides for whole PBMC.

The IP-10 responses in the CD8+ T cell depleted PBMC showed only a slight increase in the reactive peptides (16 peptides compared to 15 reactive peptides for PBMC). The number of peptides that stimulated IP-10 reactivity from >50% of the subjects with the >1.25 fold change was decreased from 13 in normal PBMC to 8 in CD8+ T cell depleted PBMC. The CD8+ T cell depletion also resulted in higher background levels (medium only) for IP-10.

Example 3. Fine Mapping of Preproinsulin Epitope

Figure 1B:
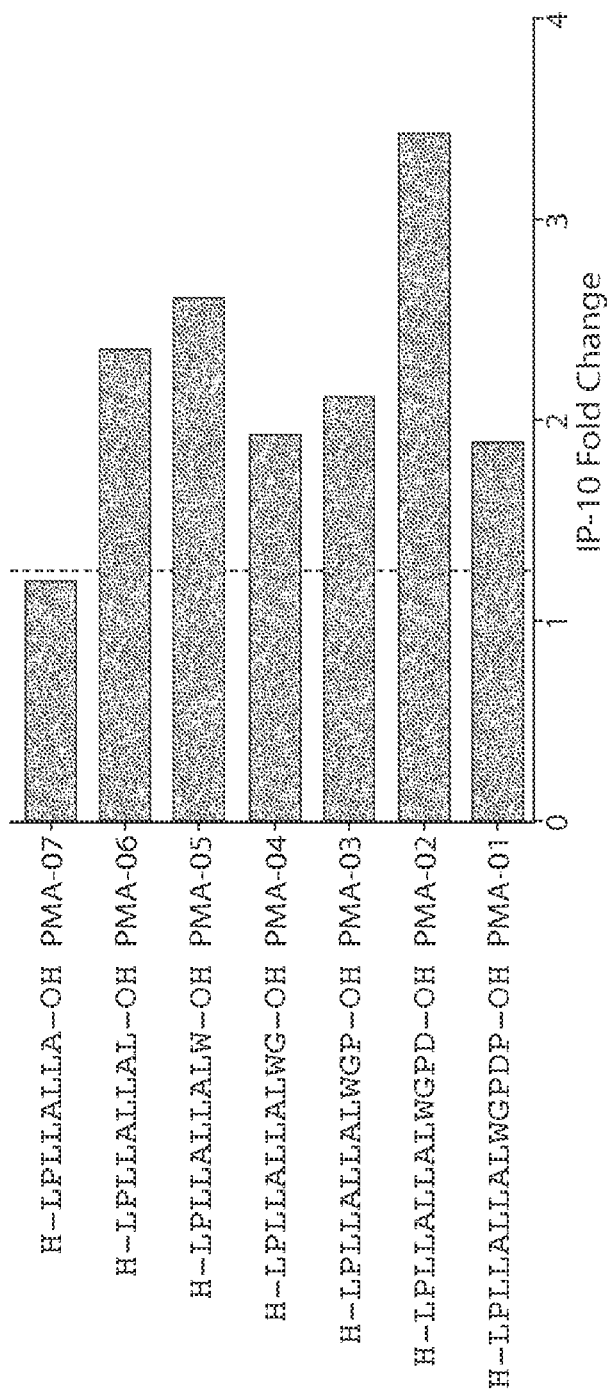
Figure 1C:
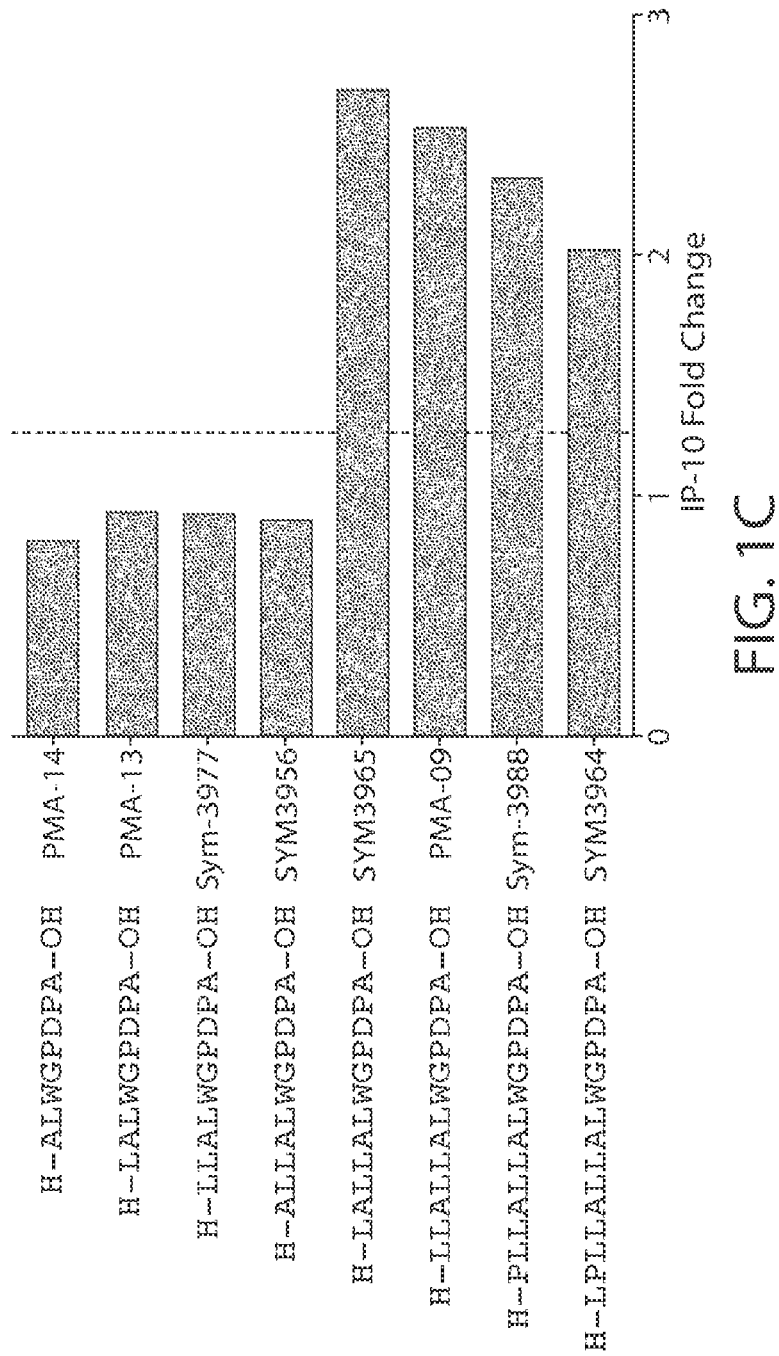

The leader sequence of the preproinsulin epitope was fine mapped with lys-substituted peptides and C- and N-terminal truncations. FIGS. 1A-1C shows graphs for the dominant 11mer epitope in preproinsulin p10-20: LLALLALWGPD (SEQ ID NO: 14). The length and observed bioactivity in the whole blood IP-10 release assay in 4 subjects with T1D is compatible with an epitope for CD4 T cells. However, the activity of the 9mer p8-16: LPLLALLAL (SEQ ID NO: 76) suggests this is an epitope for CD8 T cells and overlaps the CD4 epitope. Without wishing to be bound by any theory, a therapeutic and/or diagnostic peptide in accordance with the present disclosure may be selected to avoid CD8 activity but ensure that CD4 T cells were targeted. The data are the averages of 4 subjects whole blood IP-10 release measured as fold change over medium alone without peptide.

Whole blood was collected from 4 subjects with Type 1 Diabetes aged between 29 and 45-years old. Three subjects were HLA-DR3,4 and DQ2,8, and one was HLA-DR4,13 DQ6,8. In whole blood assays using fresh heparinized blood incubated with peptide (final concentration 10 μM) in phosphate buffered saline (PBS) and DMSO in 96-well round-bottom plates. Peptides (purity by LC-MS >80%) were truncations or lysine-substituted variants of a sequence in preproinsulin shown to be immunogenic in previous studies comparing peptides spanning this polypeptide. After 24 h at 37° C. in 5% CO2, plasma was separated and frozen –80° C. Multiplex magnetic bead-based cytokine immunoassays were performed on thawed plasma to measure the concentrations of interferon (IFN)-γ-induced protein-10 (IP-10), interleukin (IL)-2, and IFN-γ according to manufacturer's instructions (HCYTOMAG-60K, END Millipore Corp, Billerica, Mass.). Assay plates were run on the Luminex MAGPIX magnetic plate reader. The upper limit of quantitation is 10,000 pg/mL and the lower limit of detection is 3.2 pg/mL. The Fold Change of cytokine concentrations from incubations with individual peptides was calculated by dividing the cytokine concentration from the individual peptide incubations by the cytokine concentration of incubations with PBS and DMSO (NIL) on the same assay plates. Data represent mean fold-change for the 4 donors.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising a peptide, the peptide comprising the amino acid sequence GRTGTYILIDMVL-NRMA (SEQ ID NO: 12), or at least one T cell epitope contained within the amino acid sequence,
    wherein the peptide is no more than 50 amino acids in length, and
    wherein the peptide comprises a modification on the N-terminus and/or C-terminus.

2. The composition of claim 1, comprising at least two peptides, wherein
    a first peptide comprises the amino acid sequence GRT-GTYILIDMVLNRMA (SEQ ID NO: 12), or at least one T cell epitope contained within the amino acid sequence; and
    a second peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYV-VKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), PKAARPPVTPVLLEKKS (SEQ ID NO: 13), or at least one T cell epitope contained within the at least one amino acid sequence,
    wherein each of the peptides is independently no more than 50 amino acids in length.

3. The composition of claim 1, comprising at least three peptides, wherein a first peptide comprises the amino acid sequence GRT-GTYILIDMVLNRMA (SEQ ID NO: 12), or at least one T cell epitope contained within the amino acid sequence;
a second peptide comprises at least one amino acid sequence selected from PLLALLALWGPDP (SEQ ID NO: 1), PKTRREAEVGQ (SEQ ID NO: 2), RREAE-DLQGSL (SEQ ID NO: 3), RREAEDLEGSL (SEQ ID NO: 4), DLQVGQVELGGGP (SEQ ID NO: 5), DLQVGEVELGGGP (SEQ ID NO: 6), CGSHLVEALYLVC (SEQ ID NO: 7), MNILLEYV-VKS (SEQ ID NO: 8), NMFTYEIAPVFVLLEYV (SEQ ID NO: 9), NVCFWYIPPSLRTLEDN (SEQ ID NO: 10), FNQLSTGLDMVGLAADW (SEQ ID NO: 11), PKAARPPVTPVLLEKKS (SEQ ID NO: 13), or at least one T cell epitope contained within the at least one amino acid sequence; and
a third peptide comprises at least one amino acid sequence selected from PLLALLALWGPDP (SEQ ID NO: 1), PKTRREAEVGQ (SEQ ID NO: 2), RREAEDLQGSL (SEQ ID NO: 3), RREAEDLEGSL (SEQ ID NO: 4), DLQVGQVELGGGP (SEQ ID NO: 5), DLQV-GEVELGGGP (SEQ ID NO: 6), CGSHLVEALYLVC (SEQ ID NO: 7), MNILLEYVVKS (SEQ ID NO: 8), NMFTYEIAPVFVLLEYV (SEQ ID NO: 9), NVCF-WYIPPSLRTLEDN (SEQ ID NO: 10), FNQLSTGLD-MVGLAADW (SEQ ID NO: 11), PKAARPPVTPV-LLEKKS (SEQ ID NO: 13), or at least one T cell epitope contained within the at least one amino acid sequence,
wherein the second and third peptide differ from each other by one or more amino acids, and wherein each of the peptides is independently no more than 50 amino acids in length.

4. The composition of claim 1, wherein the at least one T cell epitope is not a CD8+ T cell epitope.

5. The composition of claim 1, wherein the peptide comprises an N-terminal pyroglutamate or acetyl group and/or a C-terminal amide group.

6. The composition of claim 5, wherein the peptide comprises an N-terminal pyroglutamate or acetyl group and a C-terminal amide group.

7. The composition of claim 1, wherein the peptide is no more than 30 amino acids in length.

8. The composition of claim 7, wherein the peptide is no more than 20 amino acids in length.

9. A composition comprising a polynucleotide encoding the peptide of the composition of claim 1, wherein the polynucleotide is in an expression vector.

10. An isolated antigen presenting cell comprising the composition of claim 1.

11. A kit comprising the composition of claim 1 and at least one binding partner to detect binding of one or more of the peptides in the composition to T cells.

12. A method for treating type 1 diabetes (T1D) in a subject, the method comprising:
   administering to a subject having or suspected of having T1D an effective amount of a composition of claim 1.

* * * * *

SEQUENCE LISTING

```
<160> NUMBER OF SEQ ID NOS: 105

<210> SEQ ID NO 1
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1

Pro Leu Leu Ala Leu Leu Ala Leu Trp Gly Pro Asp Pro
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 2

Pro Lys Thr Arg Arg Glu Ala Glu Val Gly Gln
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Polypeptide
```

```
<400> SEQUENCE: 3

Arg Arg Glu Ala Glu Asp Leu Gln Gly Ser Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 4

Arg Arg Glu Ala Glu Asp Leu Glu Gly Ser Leu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 5

Asp Leu Gln Val Gly Gln Val Glu Leu Gly Gly Gly Pro
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 6

Asp Leu Gln Val Gly Glu Val Glu Leu Gly Gly Gly Pro
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 7

Cys Gly Ser His Leu Val Glu Ala Leu Tyr Leu Val Cys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 8

Met Asn Ile Leu Leu Glu Tyr Val Val Lys Ser
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 9
```

Asn Met Phe Thr Tyr Glu Ile Ala Pro Val Phe Val Leu Leu Glu Tyr
1               5                   10                  15

Val

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 10

Asn Val Cys Phe Trp Tyr Ile Pro Pro Ser Leu Arg Thr Leu Glu Asp
1               5                   10                  15

Asn

<210> SEQ ID NO 11
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 11

Phe Asn Gln Leu Ser Thr Gly Leu Asp Met Val Gly Leu Ala Ala Asp
1               5                   10                  15

Trp

<210> SEQ ID NO 12
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 12

Gly Arg Thr Gly Thr Tyr Ile Leu Ile Asp Met Val Leu Asn Arg Met
1               5                   10                  15

Ala

<210> SEQ ID NO 13
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 13

Pro Lys Ala Ala Arg Pro Pro Val Thr Pro Val Leu Leu Glu Lys Lys
1               5                   10                  15

Ser

<210> SEQ ID NO 14
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 14

Leu Leu Ala Leu Leu Ala Leu Trp Gly Pro Asp
1               5                   10

```
<210> SEQ ID NO 15
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 15

Thr Pro Lys Thr Arg Arg Glu Ala Glu Asp Leu Gln Val Gly Gln Val
1               5                   10                  15

Glu Leu

<210> SEQ ID NO 16
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 16

Thr Pro Lys Thr Arg Arg Glu Ala Glu Asp Leu Gln Val Gly Gln Val
1               5                   10                  15

Glu Leu Gly Gly Gly Pro
            20

<210> SEQ ID NO 17
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 17

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 18

Met Arg Leu Leu Pro Leu Leu Ala Leu Leu Ala Leu Trp Gly Pro Asp
1               5                   10                  15

Pro Ala Ala Ala
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 19

Gly Glu Arg Gly Phe Phe Tyr Thr Pro Lys Thr Arg Arg Glu Ala Glu
1               5                   10                  15

Asp Leu Gln Val
            20
```

<210> SEQ ID NO 20
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 20

Thr Pro Lys Thr Arg Arg Glu Ala Glu Asp Leu Gln Val
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 21

Glu Asp Leu Gln Val Gly Gln Val Glu Leu Gly Gly Gly Pro Gly Ala
1               5                   10                  15

<210> SEQ ID NO 22
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 22

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 23
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 23

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 24
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 24

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Ala Arg
        35

```
<210> SEQ ID NO 25
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 25

His Leu Cys Gly Ser His Leu Val Glu Ala Leu Tyr Leu Val Cys Gly
1               5                   10                  15

Glu Arg Gly Phe Phe
            20

<210> SEQ ID NO 26
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 26

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 27

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 28
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 28

Phe Val Asn Gln His Leu Cys Gly Ser His Leu Val Glu Ala Leu Tyr
1               5                   10                  15

Leu Val Cys

<210> SEQ ID NO 29
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 29

Phe Val Asn Gln His Leu Cys Gly Ser His Leu Val Glu Ala Leu Tyr
1               5                   10                  15

Leu Val Cys Gly Glu Arg Gly
            20
```

<210> SEQ ID NO 30
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 30

Phe Val Asn Gln His Leu Cys Gly Ser His Leu Val Glu Ala Leu Tyr
1               5                   10                  15

Leu Val Cys Gly Glu Arg Gly Phe Phe Pro
            20                  25

<210> SEQ ID NO 31
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 31

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 32
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 32

Thr Asn Met Phe Thr Tyr Glu Ile Ala Pro Val Phe Val Leu Leu Glu
1               5                   10                  15

Tyr Val Thr Leu
            20

<210> SEQ ID NO 33
<211> LENGTH: 1240
<212> TYPE: DNA
<213> ORGANISM: Homo sapiens

<400> SEQUENCE: 33
cacattgttc tgatcatctg aagatcagct attagaagag aaagatcagt taagtccttt      60
ggacctgatc agcttgatac aagaactact gatttcaact tctttggctt aattctctcg    120
gaaacgatga atatacaag ttatatcttg gcttttcagc tctgcatcgt tttgggttct      180
cttggctgtt actgccagga cccatatgta aaagaagcag aaaaccttaa gaaatatttt    240
aatgcaggtc attcagatgt agcggataat ggaactcttt tcttaggcat tttgaagaat    300
tggaaagagg agagtgacag aaaaataatg cagagccaaa ttgtctcctt ttacttcaaa    360 cttttttaaaa actttaaaga tgaccagagc atccaaaaga gtgtggagac catcaaggaa    420
gacatgaatg tcaagttttt caatagcaac aaaaagaaac gagatgactt cgaaaagctg    480
actaattatt cggtaactga cttgaatgtc aacgcaaag caatacatga actcatccaa     540
gtgatggctg aactgtcgcc agcagctaaa cagggaagc gaaaaggag tcagatgctg     600 tttcgaggtc gaagagcatc ccagtaatgg ttgtcctgcc tgcaatattt gaattttaaa    660

```
tctaaatcta tttattaata tttaacatta tttatatggg gaatatattt ttagactcat    720
caatcaaata agtatttata atagcaactt ttgtgtaatg aaaatgaata tctattaata    780
tatgtattat ttataattcc tatatcctgt gactgtctca cttaatcctt tgttttctga    840
ctaattaggc aaggctatgt gattacaagg ctttatctca ggggccaact aggcagccaa    900
cctaagcaag atcccatggg ttgtgtgttt atttcacttg atgatacaat gaacacttat    960
aagtgaagtg atactatcca gttactgccg gtttgaaaat atgcctgcaa tctgagccag   1020
tgctttaatg gcatgtcaga cagaacttga atgtgtcagg tgaccctgat gaaaacatag   1080
catctcagga gatttcatgc ctggtgcttc caaatattgt tgacaactgt gactgtaccc   1140
aaatggaaag taactcattt gttaaaatta tcaatatcta atatatatga ataaagtgta   1200
agttcacaac aaaaaaaaaa aaaaaaaaaa aaaaaaaaaa                         1240
```

<210> SEQ ID NO 34
<211> LENGTH: 166
<212> TYPE: PRT
<213> ORGANISM: Homo sapiens

<400> SEQUENCE: 34

```
Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```

<210> SEQ ID NO 35
<211> LENGTH: 143
<212> TYPE: PRT
<213> ORGANISM: Homo sapiens

<400> SEQUENCE: 35

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
```

```
                50                  55                  60
Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Lys Thr Gly Lys
            115                 120                 125

Arg Lys Arg Ser Gln Met Leu Phe Arg Gly Arg Arg Ala Ser Gln
    130                 135                 140

<210> SEQ ID NO 36
<211> LENGTH: 1227
<212> TYPE: DNA
<213> ORGANISM: Homo sapiens

<400> SEQUENCE: 36
ctttgcagat aaatatggca cactagcccc acgttttctg agacattcct caattgctta      60
gacatattct gagcctacag cagaggaacc tccagtctca gcaccatgaa tcaaactgcc     120
attctgattt gctgccttat ctttctgact ctaagtggca ttcaaggagt acctctctct     180
agaactgtac gctgtacctg catcagcatt agtaatcaac ctgttaatcc aaggtctta     240
gaaaaacttg aaattattcc tgcaagccaa ttttgtccac gtgttgagat cattgctaca     300
atgaaaaaga agggtgagaa gagatgtctg aatccagaat cgaaggccat caagaattta     360
ctgaaagcag ttagcaagga aaggtctaaa agatctcctt aaaaccagag ggagcaaaa     420
tcgatgcagt gcttccaagg atggaccaca cagaggctgc ctctcccatc acttccctac     480
atggagtata tgtcaagcca taattgttct tagtttgcag ttacactaaa aggtgaccaa     540
tgatggtcac caaatcagct gctactactc ctgtaggaag gttaatgttc atcatcctaa     600
gctattcagt aataactcta ccctggcact ataatgtaag ctctactgag gtgctatgtt     660
cttagtggat gttctgaccc tgcttcaaat atttccctca cctttcccat cttccaaggg     720
tactaaggaa tctttctgct tggggtttta tcagaattct cagaatctca ataactaaa     780
aggtatgcaa tcaaatctgc tttttaaaga atgctcttta cttcatggac ttccactgcc     840
atcctcccaa ggggcccaaa ttctttcagt ggctacctac atacaattcc aaacacatac     900
aggaaggtag aaatatctga aaatgtatgt gtaagtattc ttatttaatg aaagactgta     960
caaagtagaa gtcttagatg tatatatttc ctatattgtt ttcagtgtac atggaataac    1020
atgtaattaa gtactatgta tcaatgagta acaggaaaat tttaaaaata cagatagata    1080
tatgctctgc atgttacata agataaaagt gctgaatggt tttcaaaata aaaatgaggt    1140
actctcctgg aaatattaag aaagactatc taaatgttga agatcaaaa ggttaataaa     1200
gtaattataa ctaagaaaaa aaaaaaa                                        1227

<210> SEQ ID NO 37
<211> LENGTH: 98
<212> TYPE: PRT
<213> ORGANISM: Homo sapiens

<400> SEQUENCE: 37

Met Asn Gln Thr Ala Ile Leu Ile Cys Cys Leu Ile Phe Leu Thr Leu
 1               5                  10                  15

Ser Gly Ile Gln Gly Val Pro Leu Ser Arg Thr Val Arg Cys Thr Cys
```

```
                    20                  25                  30

Ile Ser Ile Ser Asn Gln Pro Val Asn Pro Arg Ser Leu Glu Lys Leu
            35                  40                  45

Glu Ile Ile Pro Ala Ser Gln Phe Cys Pro Arg Val Glu Ile Ile Ala
        50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 38
<211> LENGTH: 77
<212> TYPE: PRT
<213> ORGANISM: Homo sapiens

<400> SEQUENCE: 38

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75

<210> SEQ ID NO 39
<211> LENGTH: 822
<212> TYPE: DNA
<213> ORGANISM: Homo sapiens

<400> SEQUENCE: 39
agttccctat cactctcttt aatcactact cacagtaacc tcaactcctg ccacaatgta     60
caggatgcaa ctcctgtctt gcattgcact aagtcttgca cttgtcacaa acagtgcacc    120
tacttcaagt tctacaaaga aaacacagct acaactggag catttactgc tggatttaca    180
gatgattttg aatggaatta taattacaa gaatcccaaa ctcaccagga tgctcacatt     240
taagttttac atgcccaaga aggccacaga actgaaacat cttcagtgtc tagaagaaga    300
actcaaacct ctggaggaag tgctaaattt agctcaaagc aaaaactttc acttaagacc    360
cagggactta atcagcaata tcaacgtaat agttctggaa ctaaagggat ctgaaacaac    420
attcatgtgt gaatatgctg atgagacagc aaccattgta gaatttctga acagatggat    480
taccttttgt caaagcatca tctcaacact gacttgataa ttaagtgctt cccacttaaa    540
acatatcagg ccttctattt atttaaatat ttaaatttta tatttattgt tgaatgtatg    600
gtttgctacc tattgtaact attattctta atcttaaaac tataaatatg gatctttat     660 gattcttttt gtaagcccta ggggctctaa aatggtttca cttatttatc ccaaaatatt    720
tattattatg ttgaatgtta aatatagtat ctatgtagat tggttagtaa aactatttaa    780
taaatttgat aaatataaaa aaaaaaaaaa aaaaaaaaa aa                        822

<210> SEQ ID NO 40
<211> LENGTH: 153
<212> TYPE: PRT
```

-continued

<213> ORGANISM: Homo sapiens

<400> SEQUENCE: 40

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 41
<211> LENGTH: 133
<212> TYPE: PRT
<213> ORGANISM: Homo sapiens

<400> SEQUENCE: 41

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 42
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)

<223> OTHER INFORMATION: Xaa is pyroglutamate
<220> FEATURE:
<221> NAME/KEY: MISC_FEATURE
<222> LOCATION: (16)..(16)
<223> OTHER INFORMATION: Modified by NH2

<400> SEQUENCE: 42

Xaa Pro Glu Gln Pro Ile Pro Glu Gln Pro Gln Pro Tyr Pro Gln Gln
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is pyroglutamate
<220> FEATURE:
<221> NAME/KEY: MISC_FEATURE
<222> LOCATION: (15)..(15)
<223> OTHER INFORMATION: Modified by NH2

<400> SEQUENCE: 43

Xaa Gln Pro Phe Pro Gln Pro Glu Gln Pro Phe Pro Trp Gln Pro
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is pyroglutamate
<220> FEATURE:
<221> NAME/KEY: MISC_FEATURE
<222> LOCATION: (16)..(16)
<223> OTHER INFORMATION: Modified by NH2

<400> SEQUENCE: 44

Xaa Leu Gln Pro Phe Pro Gln Pro Glu Leu Pro Tyr Pro Gln Pro Gln
1               5                   10                  15

<210> SEQ ID NO 45
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 45

Pro Leu Leu Ala Leu Leu Ala Leu Trp Gly Pro Asp Pro Ala Ala Ala
1               5                   10                  15

Phe

<210> SEQ ID NO 46
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 46

Phe Tyr Thr Pro Lys Thr Arg Arg Glu Ala Glu Asp Leu Gln Gly Ser

```
1               5                   10                  15
Leu

<210> SEQ ID NO 47
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 47

Met Arg Leu Leu Pro Leu Leu Ala Leu Leu Ala Leu Trp Gly Pro Asp
1               5                   10                  15

Pro

<210> SEQ ID NO 48
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 48

Arg Glu Ala Glu Asp Leu Gln Val Gly Gln Val Glu Leu Gly Gly Gly
1               5                   10                  15

Pro

<210> SEQ ID NO 49
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 49

Arg Arg Glu Ala Glu Asp Leu Glu Gly Ser Leu Gln Pro Leu Ala Leu
1               5                   10                  15

Glu

<210> SEQ ID NO 50
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 50

Glu Asp Leu Gln Val Gly Glu Val Glu Leu Gly Gly Gly Pro Gly Ala
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 51

Asn Gln His Leu Cys Gly Ser His Leu Val Glu Ala Leu Tyr Leu Val
1               5                   10                  15

Cys
```

<210> SEQ ID NO 52
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 52

Pro Lys Thr Arg Arg Glu Ala Glu Val Gly Gln Val Glu Leu Gly Gly
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 53

Cys Gly Ser His Leu Val Glu Ala Leu Tyr Leu Val Cys Gly Glu Arg
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 54

Met Ala Leu Trp Met Arg Leu Leu Pro Leu Leu Ala Leu Leu Ala Leu
1               5                   10                  15

Trp

<210> SEQ ID NO 55
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 55

Tyr Thr Pro Lys Thr Arg Arg Glu Ala Glu Asp Leu Gln Val Gly Gln
1               5                   10                  15

Val

<210> SEQ ID NO 56
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 56

Glu Ala Glu Val Gly Gln Val Glu Leu Gly Gly Gly Pro Gly Ala Gly
1               5                   10                  15

Ser

<210> SEQ ID NO 57
<211> LENGTH: 17
<212> TYPE: PRT

```
<213> ORGANISM: Artificial Sequence
<220> FEATURE:
<223> OTHER INFORMATION: Synthetic Polypeptide

<400> SEQUENCE: 57

Arg Gly Phe Phe Tyr Thr Pro Lys Thr Arg Arg Glu Ala Glu Val Gly
1               5                   10                  15

Glu

<210> SEQ ID NO 58
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 58

Pro Leu Ala Leu Glu Gly Ser Leu Gln Lys Arg Gly Ile Val Glu Gln
1               5                   10                  15

Cys

<210> SEQ ID NO 59
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 59

Arg Pro Thr Leu Ala Phe Leu Gln Asp Val Met Asn Ile Leu Leu Gln
1               5                   10                  15

Tyr

<210> SEQ ID NO 60
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 60

Lys Tyr Lys Ile Trp Met His Val Asp Ala Ala Trp Gly Gly Gly Leu
1               5                   10                  15

Leu

<210> SEQ ID NO 61
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 61

Phe Asp Arg Ser Thr Lys Val Ile Asp Phe His Tyr Pro Asn Glu Leu
1               5                   10                  15

Leu

<210> SEQ ID NO 62
<211> LENGTH: 17
<212> TYPE: PRT
<213> ORGANISM: Artificial Sequence
<220> FEATURE:
<223> OTHER INFORMATION: Synthetic Polypeptide
```

```
<400> SEQUENCE: 62

Lys Thr Gly Ile Val Ser Ser Lys Ile Ile Lys Leu Phe Phe Arg Leu
1               5                   10                  15

Gln

<210> SEQ ID NO 63
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 63

Ala Phe Leu Gln Asp Val Met Asn Ile Leu Leu Glu Tyr Val Val Lys
1               5                   10                  15

Ser

<210> SEQ ID NO 64
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 64

Met Asn Ile Leu Leu Glu Tyr Val Val Lys Ser Phe Asp Arg Ser Thr
1               5                   10                  15

Lys

<210> SEQ ID NO 65
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 65

Leu Ala Glu His Val His Met Ser Ser Gly Ser Phe Ile Asn Ile Ser
1               5                   10                  15

Val

<210> SEQ ID NO 66
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 66

Cys Thr Val Ile Val Met Leu Thr Pro Leu Val Glu Asp Gly Val Lys
1               5                   10                  15

Gln

<210> SEQ ID NO 67
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 67

Trp Glu Ser Gly Cys Thr Val Ile Val Met Leu Thr Pro Leu Val Glu
1               5                   10                  15
```

Asp

<210> SEQ ID NO 68
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 68

Ser Ser Glu Val Gln Gln Val Pro Ser Pro Val Ser Ser Glu Pro Pro
1               5                   10                  15

Lys

<210> SEQ ID NO 69
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 69

Asn Val Gly Ala Asp Ile Lys Lys Thr Met Glu Gly Pro Val Glu Gly
1               5                   10                  15

Arg

<210> SEQ ID NO 70
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 70

Ala His Ser Thr Ser Pro Met Arg Ser Val Leu Leu Thr Leu Val Ala
1               5                   10                  15

Leu

<210> SEQ ID NO 71
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 71

Ser Pro Leu Gln Ala Glu Leu Leu Pro Pro Leu Leu Glu His Leu Leu
1               5                   10                  15

Leu

<210> SEQ ID NO 72
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 72

Leu Gln Gly Ser Leu Gln Pro Leu Ala Leu Glu Gly Ser Leu Gln Lys
1               5                   10                  15

Arg

```
<210> SEQ ID NO 73
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (17)..(17)
<223> OTHER INFORMATION: Modified by NH2

<400> SEQUENCE: 73

Glu Asp Leu Gln Val Gly Gln Val Glu Leu Gly Gly Gly Pro Gly Ala
1               5                   10                  15

Gly

<210> SEQ ID NO 74
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 74

Glx Leu Gln Pro Phe Pro Gln Pro Glu Leu Pro Tyr Pro Gln Pro
1               5                   10                  15

<210> SEQ ID NO 75
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 75

Leu Pro Leu Leu Ala Leu Leu Ala
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 76

Leu Pro Leu Leu Ala Leu Leu Ala Leu
1               5

<210> SEQ ID NO 77
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 77

Leu Pro Leu Leu Ala Leu Leu Ala Leu Trp
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 78
```

```
Leu Pro Leu Leu Ala Leu Leu Ala Leu Trp Gly
1               5                   10
```

<210> SEQ ID NO 79
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 79

```
Leu Pro Leu Leu Ala Leu Leu Ala Leu Trp Gly Pro
1               5                   10
```

<210> SEQ ID NO 80
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 80

```
Leu Pro Leu Leu Ala Leu Leu Ala Leu Trp Gly Pro Asp
1               5                   10
```

<210> SEQ ID NO 81
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 81

```
Leu Pro Leu Leu Ala Leu Leu Ala Leu Trp Gly Pro Asp Pro
1               5                   10
```

<210> SEQ ID NO 82
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 82

```
Leu Pro Leu Leu Ala Leu Leu Ala Leu Trp Gly Pro Asp Pro Lys
1               5                   10                  15
```

<210> SEQ ID NO 83
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 83

```
Leu Pro Leu Leu Ala Leu Leu Ala Leu Trp Gly Pro Asp Lys Ala
1               5                   10                  15
```

<210> SEQ ID NO 84
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 84

Leu Pro Leu Leu Ala Leu Leu Ala Leu Trp Gly Pro Lys Pro Ala
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 85

Leu Pro Leu Leu Ala Leu Leu Ala Leu Trp Gly Lys Asp Pro Ala
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 86

Leu Pro Leu Leu Ala Leu Leu Ala Leu Trp Lys Pro Asp Pro Ala
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 87

Leu Pro Leu Leu Ala Leu Leu Ala Leu Lys Gly Pro Asp Pro Ala
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 88

Leu Pro Leu Leu Ala Leu Leu Ala Lys Trp Gly Pro Asp Pro Ala
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 89

Leu Pro Leu Leu Ala Leu Leu Lys Leu Trp Gly Pro Asp Pro Ala
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 90

Leu Pro Leu Leu Ala Leu Lys Ala Leu Trp Gly Pro Asp Pro Ala

```
<210> SEQ ID NO 91
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 91

Leu Pro Leu Leu Ala Lys Leu Ala Leu Trp Gly Pro Asp Pro Ala
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 92

Leu Pro Leu Leu Lys Leu Leu Ala Leu Trp Gly Pro Asp Pro Ala
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 93

Leu Pro Leu Lys Ala Leu Leu Ala Leu Trp Gly Pro Asp Pro Ala
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 94

Leu Pro Lys Leu Ala Leu Leu Ala Leu Trp Gly Pro Asp Pro Ala
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 95

Leu Lys Leu Leu Ala Leu Leu Ala Leu Trp Gly Pro Asp Pro Ala
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 96

Lys Pro Leu Leu Ala Leu Leu Ala Leu Trp Gly Pro Asp Pro Ala
1               5                   10                  15
```

```
<210> SEQ ID NO 97
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 97

Leu Pro Leu Leu Ala Leu Leu Ala Leu Trp Gly Pro Asp Pro Ala
1               5                   10                  15

<210> SEQ ID NO 98
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 98

Ala Leu Trp Gly Pro Asp Pro Ala
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 99

Leu Ala Leu Trp Gly Pro Asp Pro Ala
1               5

<210> SEQ ID NO 100
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 100

Leu Leu Ala Leu Trp Gly Pro Asp Pro Ala
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 101

Ala Leu Leu Ala Leu Trp Gly Pro Asp Pro Ala
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 102

Leu Ala Leu Leu Ala Leu Trp Gly Pro Asp Pro Ala
1               5                   10
```

```
<210> SEQ ID NO 103
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 103

Leu Leu Ala Leu Leu Ala Leu Trp Gly Pro Asp Pro Ala
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 104

Pro Leu Leu Ala Leu Leu Ala Leu Trp Gly Pro Asp Pro Ala
1               5                   10

<210> SEQ ID NO 105
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 105

Pro Leu Leu Ala Leu Leu Ala Leu Trp
1               5
```